United States Patent
Kim et al.

(10) Patent No.: US 11,114,622 B2
(45) Date of Patent: Sep. 7, 2021

(54) COMPOUND AND ORGANIC LIGHT-EMITTING DEVICE INCLUDING THE SAME

(71) Applicant: Samsung Display Co., Ltd., Yongin-si (KR)

(72) Inventors: Youngkook Kim, Yongin-si (KR); Sooyon Kim, Yongin-si (KR); Jongwoo Kim, Yongin-si (KR); Seokhwan Hwang, Yongin-si (KR); Jeonga Oh, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 247 days.

(21) Appl. No.: 15/152,540

(22) Filed: May 11, 2016

(65) Prior Publication Data

US 2017/0117482 A1    Apr. 27, 2017

(30) Foreign Application Priority Data

Oct. 22, 2015 (KR) .................. 10-2015-0147537

(51) Int. Cl.
*H01L 51/00* (2006.01)
*C07B 59/00* (2006.01)
(Continued)

(52) U.S. Cl.
CPC ........ *H01L 51/0061* (2013.01); *C07B 59/002* (2013.01); *C07D 223/18* (2013.01);
(Continued)

(58) Field of Classification Search
CPC ... H01L 51/5056–5064; H01L 51/0059–0061; H01L 51/00–56; C07D 223/16–30
See application file for complete search history.

(56) References Cited

U.S. PATENT DOCUMENTS

| 4,521,605 A | 6/1985 | Okazaki et al. |
| 5,635,308 A | 6/1997 | Inoue et al. |

(Continued)

FOREIGN PATENT DOCUMENTS

| JP | 08-12600 A | 1/1996 |
| JP | 10-59943 A | 3/1998 |

(Continued)

OTHER PUBLICATIONS

Koene, et al. "Asymmetric triaryldiamines as thermally stable hole transporting layers for organic light-emitting devices." Chemistry of materials 10.8 (1998): 2235-2250.*

(Continued)

*Primary Examiner* — William E McClain
(74) *Attorney, Agent, or Firm* — Lewis Roca Rothgerber Christie LLP

(57) ABSTRACT

An organic light-emitting device includes: a first electrode; a second electrode facing the first electrode; and an organic layer between the first electrode and the second electrode, the organic layer including an emission layer, wherein the organic layer includes a compound of Formula 1:

(Continued)

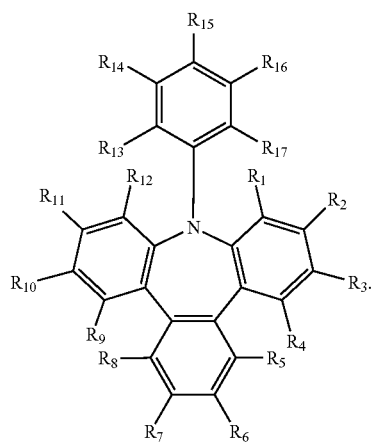

Formula 1

According to one or more embodiments of the present disclosure, due to the inclusion of the compound of Formula 1, characteristics of an organic light-emitting device may be improved.

13 Claims, 1 Drawing Sheet

(51) Int. Cl.
<table>
<tr><td>*C07D 223/18*</td><td>(2006.01)</td></tr>
<tr><td>*C07D 401/04*</td><td>(2006.01)</td></tr>
<tr><td>*C07D 401/12*</td><td>(2006.01)</td></tr>
<tr><td>*C07D 403/12*</td><td>(2006.01)</td></tr>
<tr><td>*C07D 405/04*</td><td>(2006.01)</td></tr>
<tr><td>*C07D 405/12*</td><td>(2006.01)</td></tr>
<tr><td>*C07D 409/04*</td><td>(2006.01)</td></tr>
<tr><td>*C07D 409/12*</td><td>(2006.01)</td></tr>
<tr><td>*C07D 471/04*</td><td>(2006.01)</td></tr>
<tr><td>*C07F 7/08*</td><td>(2006.01)</td></tr>
<tr><td>*H01L 27/32*</td><td>(2006.01)</td></tr>
<tr><td>*H01L 51/50*</td><td>(2006.01)</td></tr>
</table>

(52) U.S. Cl.
CPC .......... *C07D 401/04* (2013.01); *C07D 401/12* (2013.01); *C07D 403/12* (2013.01); *C07D 405/04* (2013.01); *C07D 405/12* (2013.01); *C07D 409/04* (2013.01); *C07D 409/12* (2013.01); *C07D 471/04* (2013.01); *C07F 7/0812* (2013.01); *H01L 27/3244* (2013.01); *H01L 51/006* (2013.01); *H01L 51/0059* (2013.01); *H01L 51/0067* (2013.01); *H01L 51/0072* (2013.01); *H01L 51/0073* (2013.01); *H01L 51/0094* (2013.01); *H01L 51/0052* (2013.01); *H01L 51/0056* (2013.01); *H01L 51/0058* (2013.01); *H01L 51/0074* (2013.01); *H01L 51/5056* (2013.01); *H01L 51/5064* (2013.01); *H01L 51/5072* (2013.01)

(56) References Cited

U.S. PATENT DOCUMENTS

<table>
<tr><td>5,929,235</td><td>A</td><td>7/1999</td><td>Sato</td></tr>
<tr><td>5,972,247</td><td>A</td><td>10/1999</td><td>Shi et al.</td></tr>
<tr><td>6,313,349</td><td>B1</td><td>11/2001</td><td>Sato</td></tr>
<tr><td>6,387,544</td><td>B1</td><td>5/2002</td><td>Thompson et al.</td></tr>
<tr><td>6,436,558</td><td>B1</td><td>8/2002</td><td>Sato et al.</td></tr>
<tr><td>6,465,115</td><td>B2</td><td>10/2002</td><td>Shi et al.</td></tr>
<tr><td>6,596,415</td><td>B2</td><td>7/2003</td><td>Shi et al.</td></tr>
<tr><td>6,660,410</td><td>B2</td><td>12/2003</td><td>Hosokawa</td></tr>
<tr><td>6,670,054</td><td>B1</td><td>12/2003</td><td>Hu et al.</td></tr>
<tr><td>6,979,414</td><td>B2</td><td>12/2005</td><td>Hosokawa</td></tr>
<tr><td>7,201,974</td><td>B2</td><td>4/2007</td><td>Hamada</td></tr>
<tr><td>2001/0046612</td><td>A1</td><td>11/2001</td><td>Lee et al.</td></tr>
<tr><td>2003/0065171</td><td>A1</td><td>4/2003</td><td>Sato et al.</td></tr>
<tr><td>2010/0171105</td><td>A1*</td><td>7/2010</td><td>Kim ............. H01L 27/322<br>257/40</td></tr>
<tr><td>2010/0295445</td><td>A1</td><td>11/2010</td><td>Kuma et al.</td></tr>
<tr><td>2012/0074395</td><td>A1</td><td>3/2012</td><td>Yabunouchi et al.</td></tr>
<tr><td>2013/0328027</td><td>A1*</td><td>12/2013</td><td>Sotoyama ......... H01L 51/5092<br>257/40</td></tr>
<tr><td>2014/0042412</td><td>A1*</td><td>2/2014</td><td>Ryu ............. H01L 51/0059<br>257/40</td></tr>
<tr><td>2015/0048324</td><td>A1</td><td>2/2015</td><td>Shin et al.</td></tr>
<tr><td>2015/0194610</td><td>A1*</td><td>7/2015</td><td>Hwang ............. H01L 51/0072<br>257/40</td></tr>
<tr><td>2016/0163998</td><td>A1*</td><td>6/2016</td><td>Saito ............. H01L 51/0072<br>257/40</td></tr>
</table>

FOREIGN PATENT DOCUMENTS

<table>
<tr><td>JP</td><td>10-219241 A</td><td></td><td>8/1998</td><td></td></tr>
<tr><td>JP</td><td>10310574 A</td><td>*</td><td>11/1998</td><td></td></tr>
<tr><td>JP</td><td>10-316875 A</td><td></td><td>12/1998</td><td></td></tr>
<tr><td>JP</td><td>10-324680 A</td><td></td><td>12/1998</td><td></td></tr>
<tr><td>JP</td><td>11-3782 A</td><td></td><td>1/1999</td><td></td></tr>
<tr><td>JP</td><td>2000113985 A</td><td>*</td><td>4/2000</td><td></td></tr>
<tr><td>JP</td><td>2000-268975 A</td><td></td><td>9/2000</td><td></td></tr>
<tr><td>JP</td><td>2006269836 A</td><td>*</td><td>10/2006</td><td></td></tr>
<tr><td>JP</td><td>4115555 B2</td><td></td><td>7/2008</td><td></td></tr>
<tr><td>JP</td><td>2014-160813 A</td><td></td><td>9/2014</td><td></td></tr>
<tr><td>KR</td><td>10-0346984 B1</td><td></td><td>7/2002</td><td></td></tr>
<tr><td>KR</td><td>10-2011-0008619 A</td><td></td><td>1/2011</td><td></td></tr>
<tr><td>KR</td><td>10-2011-0087214 A</td><td></td><td>8/2011</td><td></td></tr>
<tr><td>KR</td><td>10-2012-0022859 A</td><td></td><td>3/2012</td><td></td></tr>
<tr><td>KR</td><td>10-2012-0024624 A</td><td></td><td>3/2012</td><td></td></tr>
<tr><td>KR</td><td>10-2015-0019724 A</td><td></td><td>2/2015</td><td></td></tr>
<tr><td>KR</td><td>10-2015-0021861 A</td><td></td><td>3/2015</td><td></td></tr>
<tr><td>WO</td><td>WO 2011/010839 A1</td><td></td><td>1/2011</td><td></td></tr>
<tr><td>WO</td><td>WO-2012011756 A1</td><td>*</td><td>1/2012</td><td>.......... C07D 209/86</td></tr>
<tr><td>WO</td><td>WO-2015047018 A1</td><td>*</td><td>4/2015</td><td>.......... C07D 403/14</td></tr>
<tr><td>WO</td><td>WO-2016102039 A1</td><td>*</td><td>6/2016</td><td>.......... H01L 51/0072</td></tr>
</table>

OTHER PUBLICATIONS

Machine translation of JP-2006269836-A.*
Machine Translation of JP 2000/113985 A.*
Machine Translation of WO 2016/102039 A1.*
Machine Translation of WO-2015047018-A1.*
English Abstract for JP 10-330356, dated Dec. 15, 1998, which corresponds to JP 415555 B2 listed above.

* cited by examiner

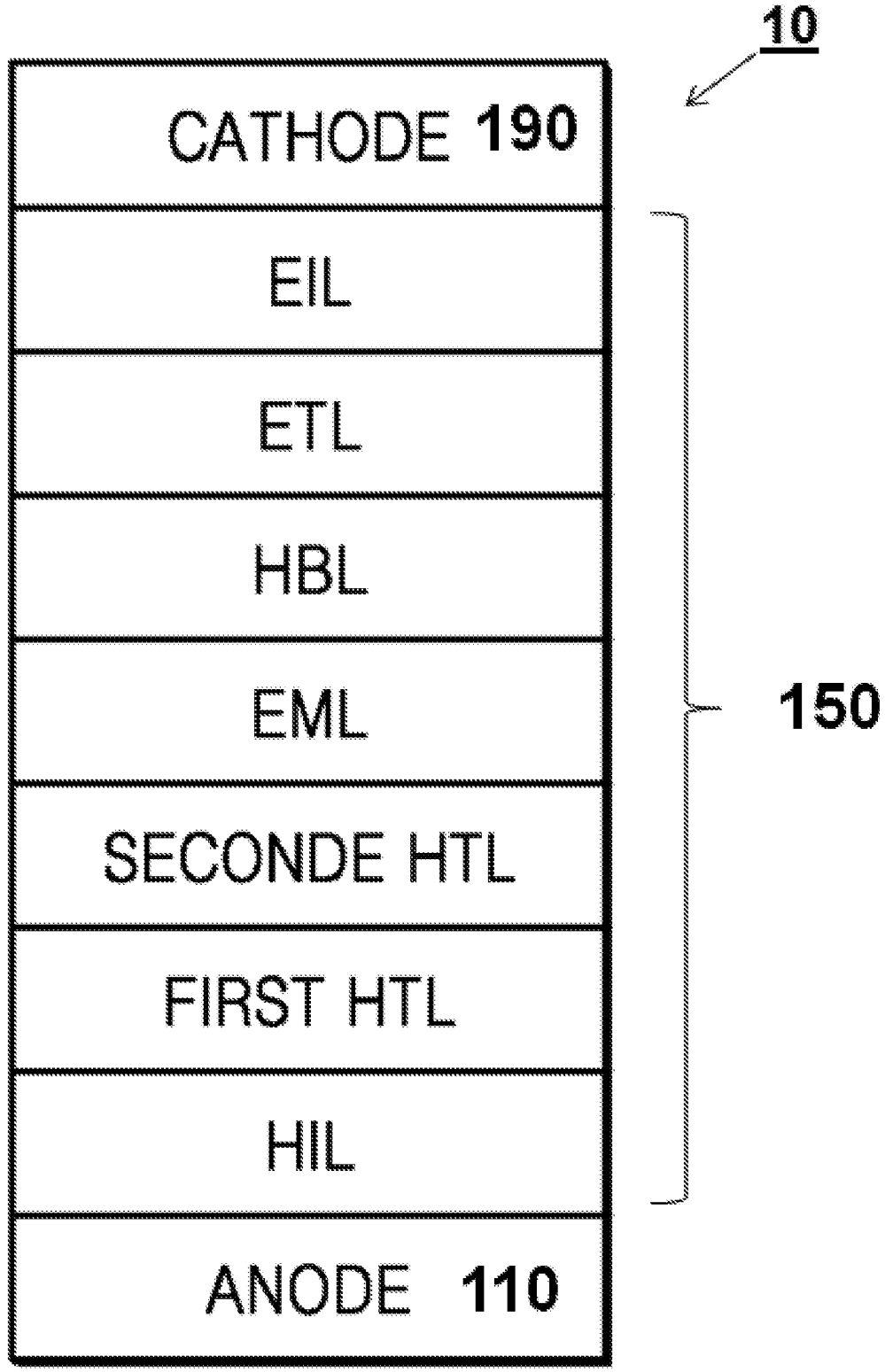

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0147537, filed on Oct. 22, 2015, in the Korean Intellectual Property Office, the entire disclosure of which is incorporated herein by reference.

BACKGROUND

1. Field

One or more aspects of embodiments of the present disclosure relate to a compound and an organic light-emitting device including the same.

2. Description of the Related Art

Organic light-emitting devices are self-emission devices that have wide viewing angles, high contrast ratios, short response times, and excellent brightness, driving voltage, and/or response speed characteristics, and can produce full-color images.

An organic light-emitting device may include a first electrode disposed (e.g., positioned) on a substrate, and a hole transport region, an emission layer, an electron transport region, and a second electrode, which are sequentially disposed on the first electrode. Holes provided from the first electrode, for example, may move toward the emission layer through the hole transport region, and electrons provided from the second electrode, for example, may move toward the emission layer through the electron transport region. Carriers, such as holes and electrons, may then recombine in the emission layer to produce excitons. These excitons transition from an excited state to a ground state, thereby generating light.

SUMMARY

One or more aspects of embodiments of the present disclosure are directed toward a material for forming a hole transport region and an organic light-emitting device having improved characteristics due to the inclusion of the material.

Additional aspects will be set forth in part in the description which follows and, in part, will be apparent from the description, or may be learned by practice of the presented embodiments.

According to one or more embodiments, a compound represented by Formula 1 is provided:

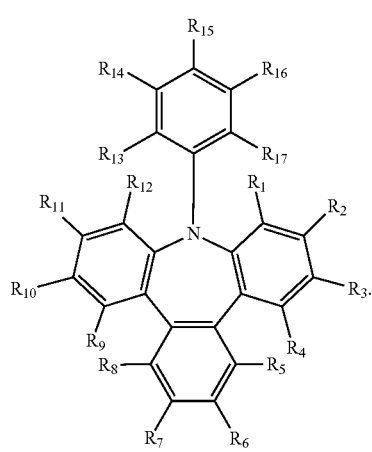

Formula 1

In Formula 1, $R_1$ to $R_{17}$ may each independently be selected from hydrogen, deuterium, halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

at least one of $R_1$ to $R_{17}$ includes a group represented by Formula 1-1:

Formula 1-1 where $Ar_1$ and $Ar_2$ in Formula 1-1 may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that each of $Ar_1$ and $Ar_2$ is not a substituted or unsubstituted dibenzoazepine or a substituted or unsubstituted tribenzoazepine;

X may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

m may be an integer selected from 0 to 5;

when m is 2 or more, 2 or more X(s) may be identical to or different from each other; and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group, substituted $C_6$-$C_{60}$ arylene group, substituted $C_1$-$C_{60}$ heteroarylene group, a substituted divalent non-aromatic condensed polycyclic group, and a substituted divalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and Si($Q_{13}$)($Q_{14}$)($Q_{15}$), wherein $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Another embodiment of the present disclosure provides an organic light-emitting device that includes: a first electrode; a second electrode facing the first electrode; and an organic layer between the first electrode and the second electrode, the organic layer including an emission layer, wherein the organic layer includes the compound of Formula 1.

Another embodiment of the present disclosure provides a display apparatus including the organic light-emitting device, wherein the first electrode of the organic light-emitting device is electrically coupled to a source electrode or a drain electrode of a thin film transistor.

BRIEF DESCRIPTION OF THE DRAWING

These and/or other aspects will become apparent and more readily appreciated from the following description of the embodiments, taken in conjunction with the drawing, which is a schematic view of an organic light-emitting device according to an embodiment of the present disclosure.

DETAILED DESCRIPTION

Reference will now be made in more detail to embodiments, examples of which are illustrated in the accompanying drawing, wherein like reference numerals refer to like elements throughout. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of," "one of," and "selected from," when preceding a list of elements, modify the entire list of elements and do not modify the individual elements of the list. Further, the use of "may" when describing embodiments of the present invention refers to "one or more embodiments of the present invention."

A compound according to an embodiment may be represented by Formula 1 below:

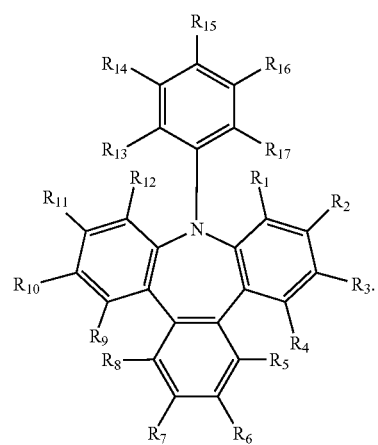

Formula 1

In Formula 1, $R_1$ to $R_{17}$ may each independently be selected from hydrogen, deuterium, halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

where at least one of $R_1$ to $R_{17}$ includes a group represented by Formula 1-1:

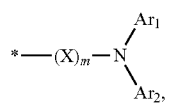

Formula 1-1 where $Ar_1$ and $Ar_2$ in Formula 1-1 may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that each of $Ar_1$ and $Ar_2$ is not a substituted or unsubstituted dibenzoazepine or a substituted or unsubstituted tribenzoazepine;

X may be selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

m may be an integer selected from 0 to 5;

when m is 2 or more, a plurality of X may be identical to or different from each other; and at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group, substituted $C_6$-$C_{60}$ arylene group, substituted $C_1$-$C_{60}$ heteroarylene group, a substituted divalent non-aromatic condensed polycyclic group, and a substituted divalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{16}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and Si($Q_{13}$)($Q_{14}$)($Q_{15}$), wherein $Q_{11}$ to $Q_{17}$ and $Q_{21}$ to $Q_{27}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Compounds including an azepine moiety, which is a nitrogen-containing 7-membered ring compound, can be used as a charge transport material for electrophotography or an organic light-emitting device. From among such compounds, ethylene-based compound including an azepine moiety, a hydrazone compound having a benzazepine skeleton, and/or a compound having two or more benzoazepine moieties may be used in a hole transport layer of an organic device.

Various compounds including azepine moieties may be used as phosphorescent hosts, fluorescent hosts, dopants and/or materials for an electron transport layer, and may also be included in a hole transport layer. For example, an azepine-containing arylamine compound has been used as material for a hole transport layer.

However, monoamine or diamine derivatives having two or more azepine groups may have low efficiency and relatively short lifespan, when they are used as a hole transport material. Due to these characteristics, such monoamine or diamine derivatives may not be commercially available. Accordingly, there are efforts to use other arylamine derivatives to develop a hole injection material that has low voltage, high efficiency, and a long lifespan.

Recently, to improve efficiency of an organic light-emitting device and to increase singlet exciton-generation efficiency by triplet-triplet fusion (TTF) (which effectively uses excitons generated in an emission layer), a first hole transport layer having a conventional triplet energy level and a second hole transport layer having a triplet energy level that is higher than the conventional triplet energy level has been described. For example, various compounds may be used for such second hole transport layer.

In embodiments of the present disclosure, a monoamine compound (e.g., a compound including one azepine moiety) is used as a hole transport material to improve characteristics of an organic light-emitting device.

Substituents of Formula 1 will now be described in more detail.

In various embodiments, two or more adjacent substituents selected from $R_{13}$ to $R_{17}$ in Formula 1 may be linked to each other to form a ring. Non-limiting examples of compound of Formula 1 in which two or more adjacent substituents selected from $R_{13}$ to $R_{17}$ are linked to each other to form a ring include Compounds 32, 36, 40-45, and 47.

In various embodiments, $Ar_1$ and $Ar_2$ in Formula 1-1 may be linked to each other to form a ring. Non-limiting examples of compound of Formula 1, in which $Ar_1$ and $Ar_2$ in Formula 1-1 are linked to each other to form a ring, include Compounds 58-60.

In various embodiments, m in Formula 1-1 may be an integer selected from 0 to 3.

In various embodiments, $R_3$ and $R_{10}$ in Formula 1 may each independently be a substituted or unsubstituted phenyl group.

In various embodiments, $R_1$, $R_4$ to $R_9$, $R_{12}$, $R_{13}$, and $R_{17}$ in Formula 1 and Formula 4 (illustrated below) may each independently be hydrogen or deuterium.

In various embodiments, X in Formula 1-1 may be a group represented by any one selected from Formulae 2a to 2f:

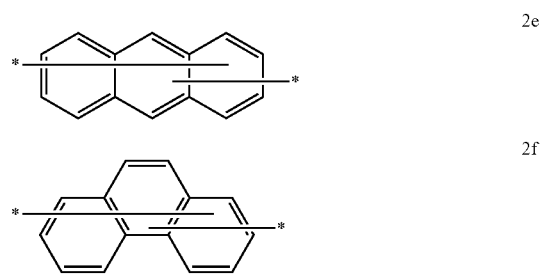

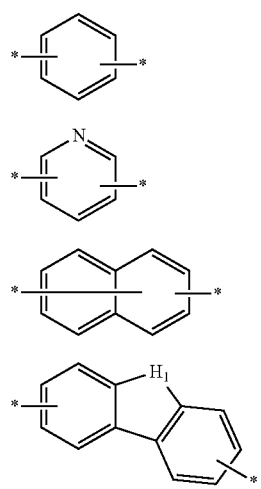

In Formulae 2a to 2f, $H_1$ may be selected from O, S, $NR_{21}$, and $CR_{22}R_{23}$, $R_{21}$ to $R_{23}$ may each independently be selected from hydrogen, deuterium, halogen, a substituted or unsubstituted C1-C20 alkyl group, a substituted or unsubstituted C6-C20 aryl group, a substituted or unsubstituted C1-C20 heteroaryl group, a substituted or unsubstituted monovalent non-aromatic condensed polycyclic group, and a substituted or unsubstituted monovalent non-aromatic condensed heteropolycyclic group; and * indicates a binding site.

In various embodiments, $Ar_1$ and $Ar_2$ in Formula 1-1 may each independently be a group represented by one selected from Formulae 3a to 3g:

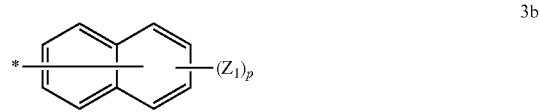

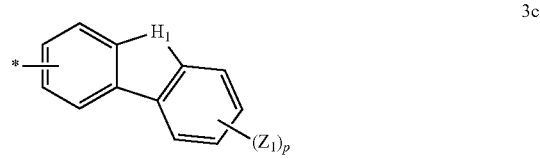

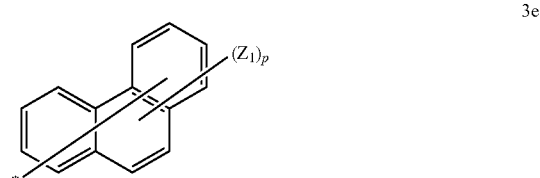

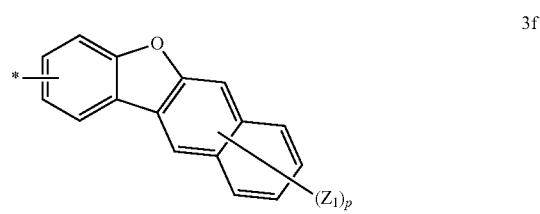

-continued

3g

In Formulae 3a to 3g, $H_1$ may be selected from O, S, $NR_{21}$, and $CR_{22}R_{23}$, $R_{21}$ to $R_{23}$ and $Z_1$ may each independently be selected from hydrogen, deuterium, halogen, a substituted or unsubstituted C1-C20 alkyl group, a substituted or unsubstituted C6-C20 aryl group, a substituted or unsubstituted C1-C20 heteroaryl group, a substituted or unsubstituted monovalent non-aromatic condensed polycyclic group, a substituted or unsubstituted monovalent non-aromatic condensed heteropolycyclic group, and $Si(Q_{13})(Q_{14})(Q_{15})$, where $Q_{13}$ to $Q_{15}$ are as defined herein;

p in Formula 3a may be an integer selected from 1 to 5, p in Formula 3b may be an integer selected from 1 to 7, p in Formulae 3c and 3d may be an integer selected from 1 to 4 and p in Formulae 3e to 3g may be an integer selected from 1 to 6, wherein when p is 2 or more, 2 or more $Z_1$(s) may each be identical to or different from each other; and

*indicates a binding site.

In some embodiments, when $H_1$ in Formula 3c is $CR_{22}R_{23}$, $R_{22}$ and $R_{23}$ may be linked to each other to form a ring.

In various embodiments, the compound of Formula 1 may be represented Formula 2:

Formula 2

In various embodiments, the compound of Formula 1 may be represented by Formula 3:

Formula 3

In various embodiments, the compound of Formula 1 may be represented by Formula 4:

Formula 4

In various embodiments, the compound of Formula 1 may be represented by Formula 5:

Formula 5

In various embodiments, the compound of Formula 1 may be represented by Formula 6:

Formula 6
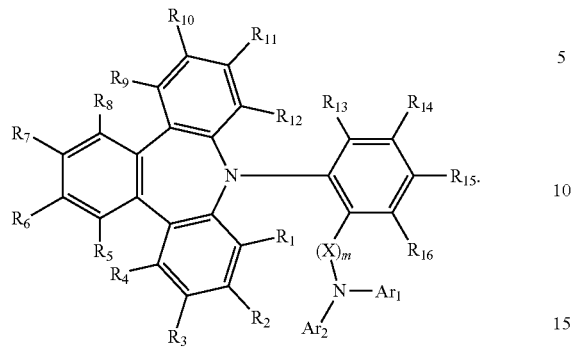
In various embodiments, the compound of Formula 1 may be one of the following Compounds 1 to 117:
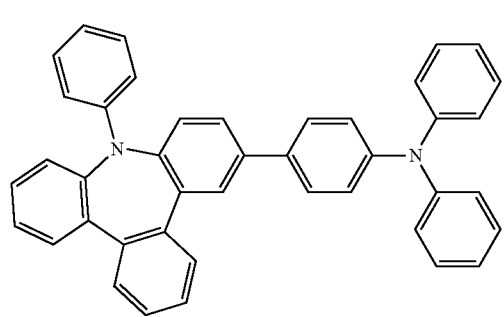
1
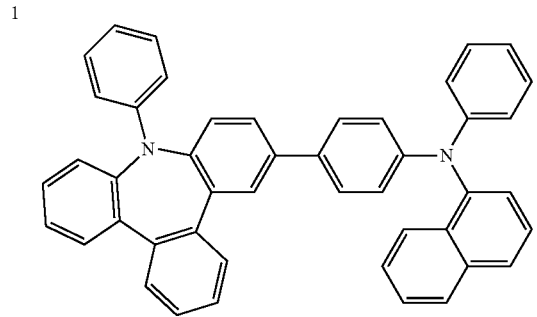
2
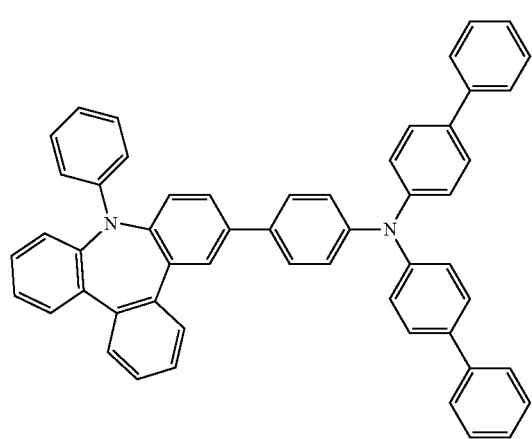
3
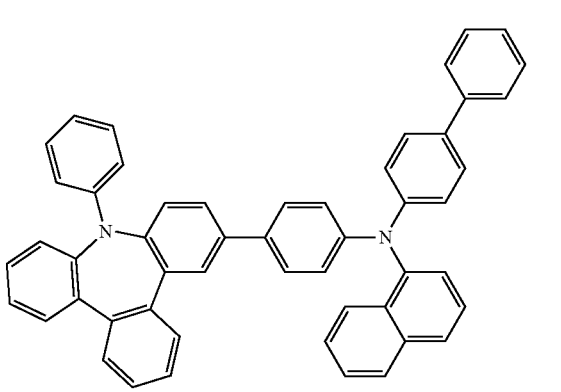
4

-continued
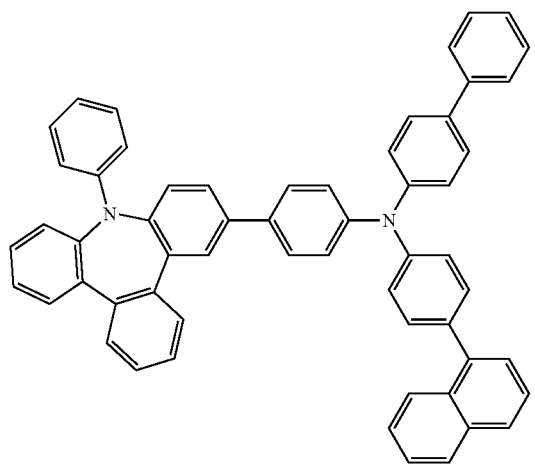
5
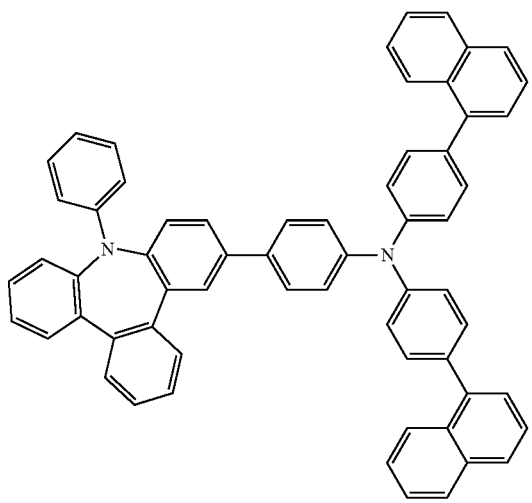
6
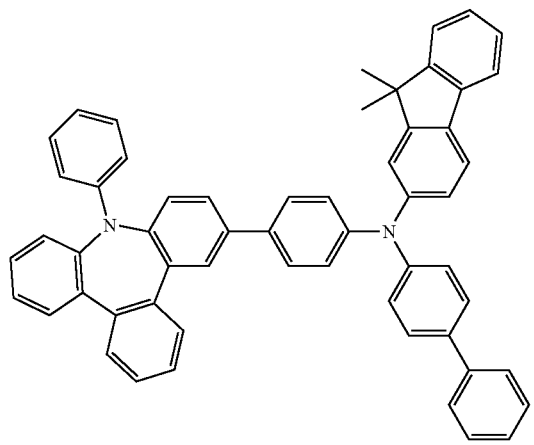
7
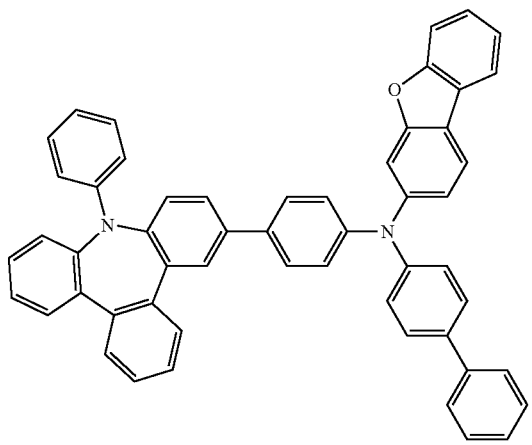
8
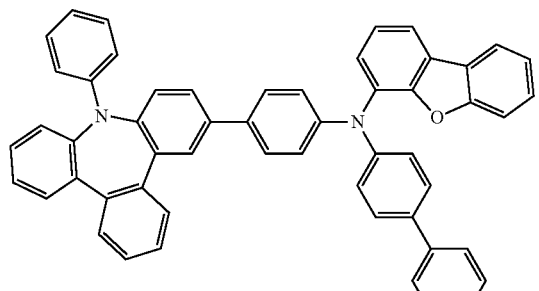
9
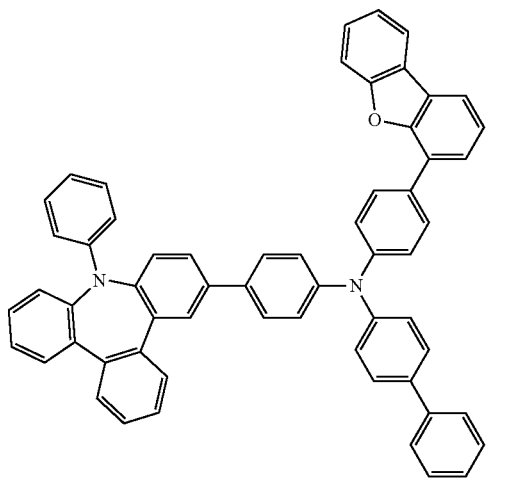
10

-continued
11
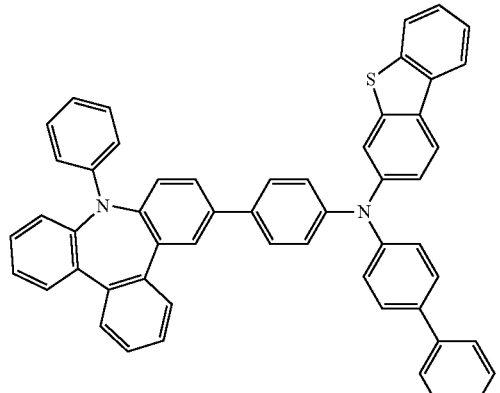
12
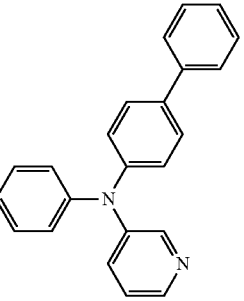
13
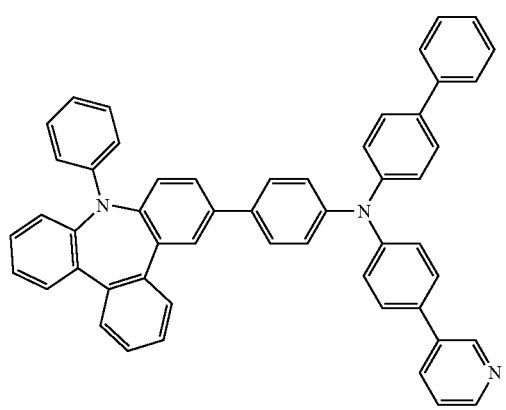
14
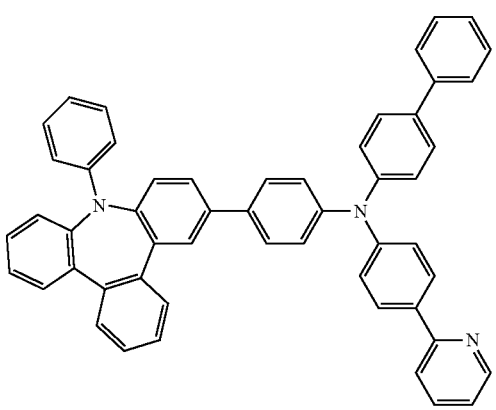
15
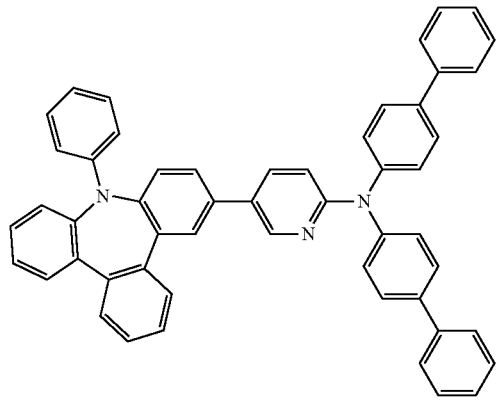
16
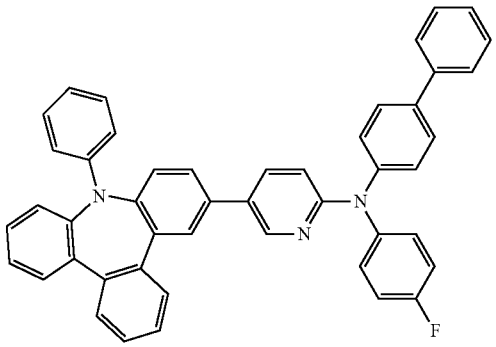
17
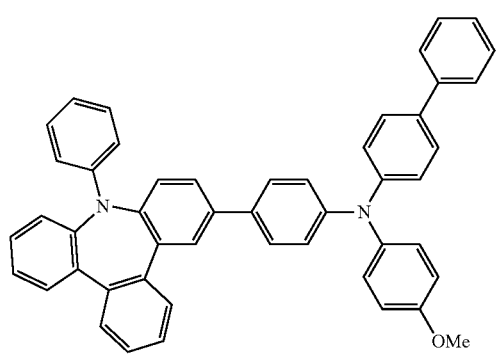
18
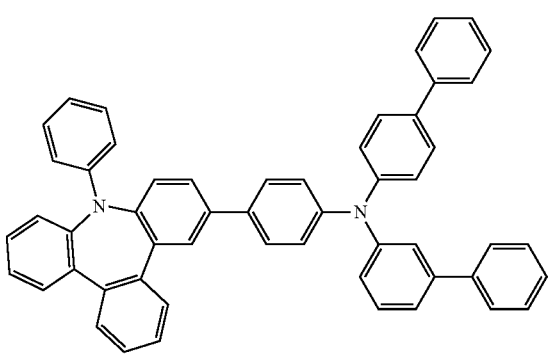

-continued
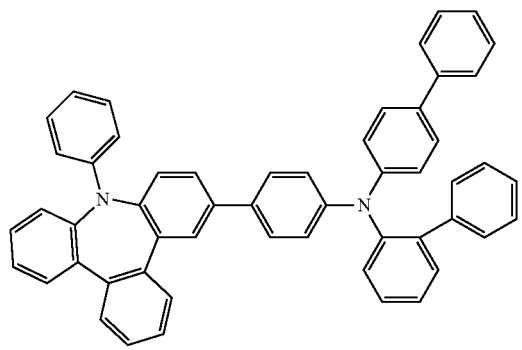
19
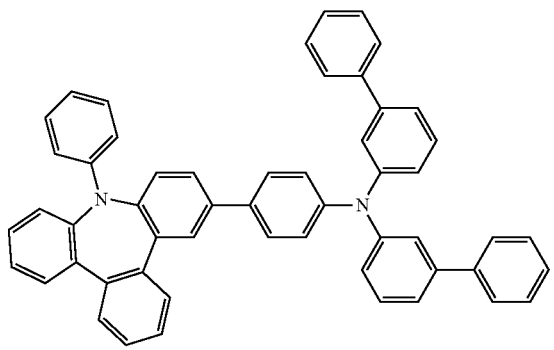
20
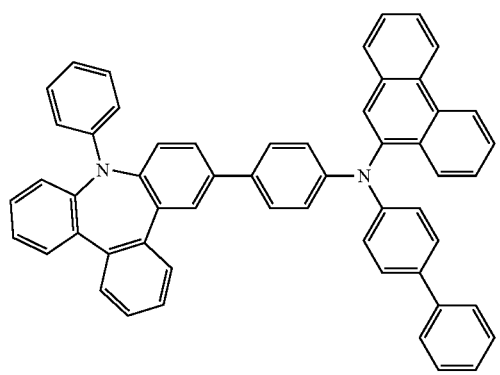
21
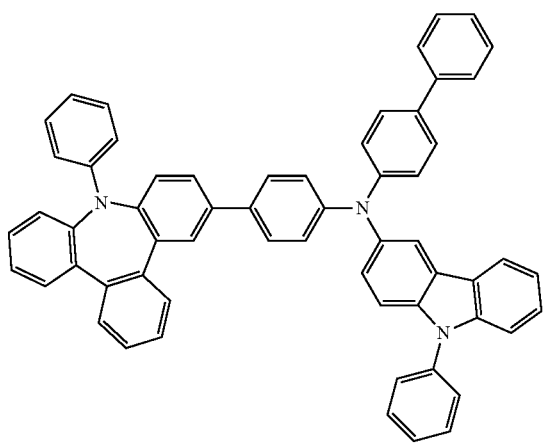
22
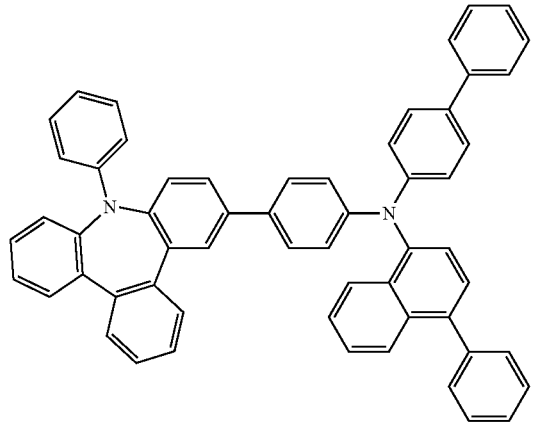
23
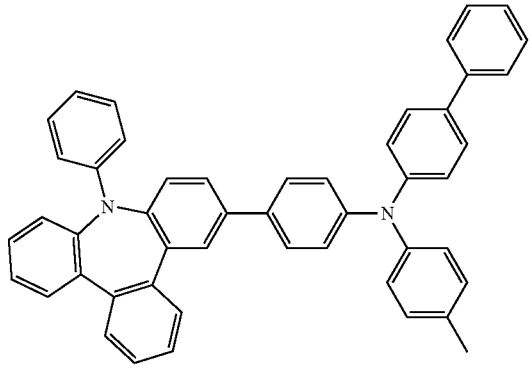
24

-continued
25
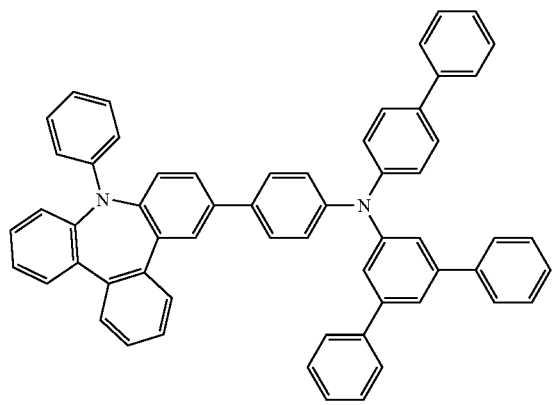
26
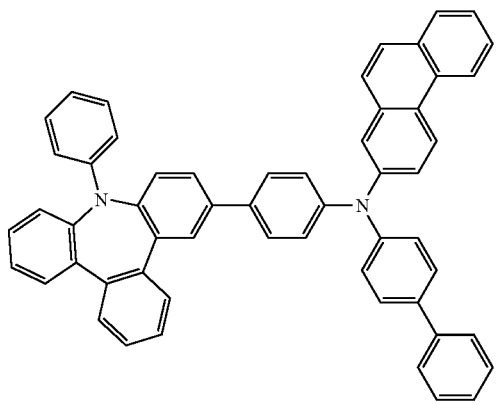
27
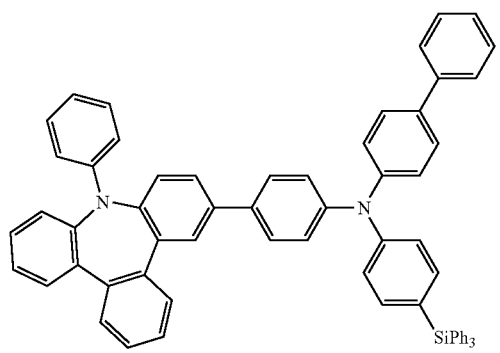
28
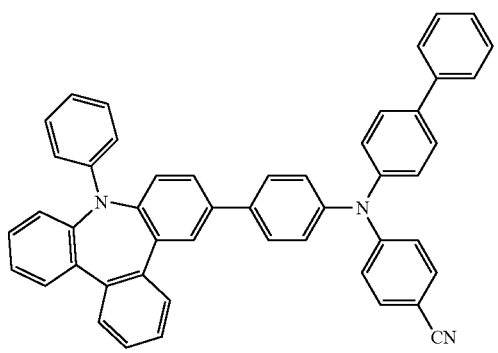
29
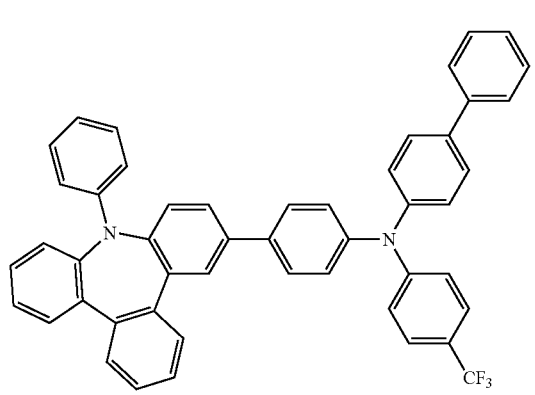
30
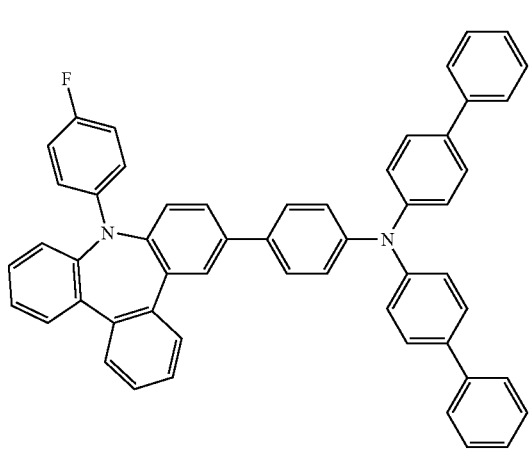
31
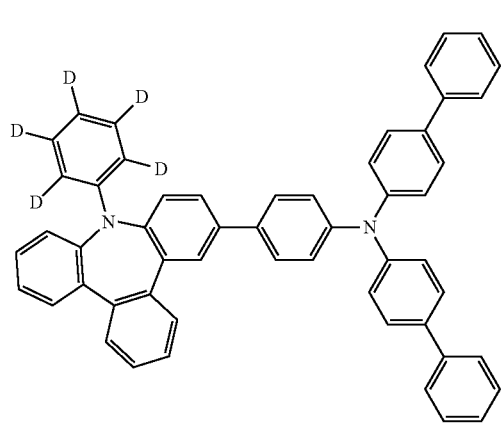
32
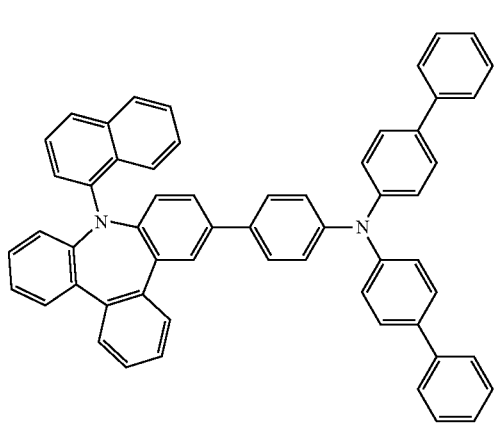

-continued
33
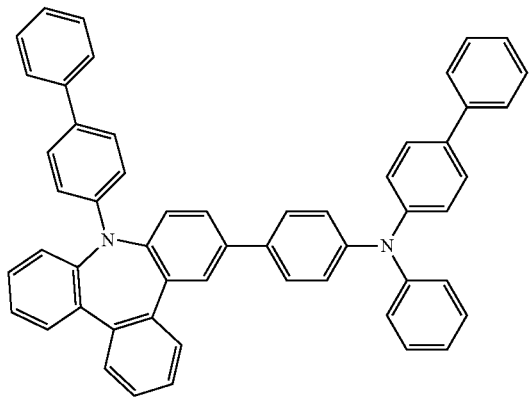
34
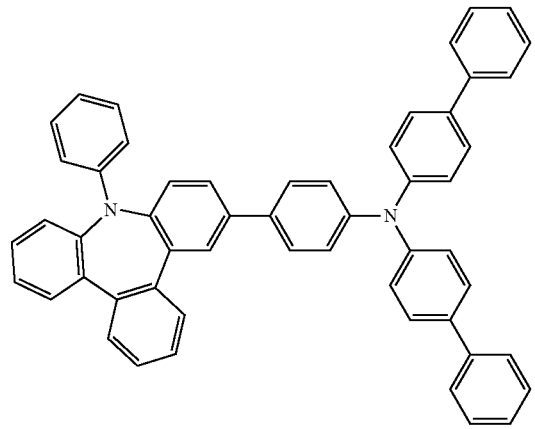
35
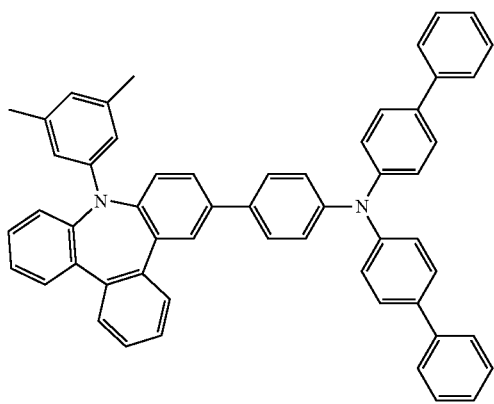
36
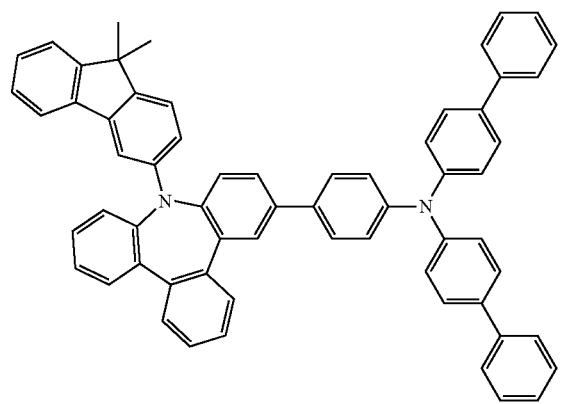
37
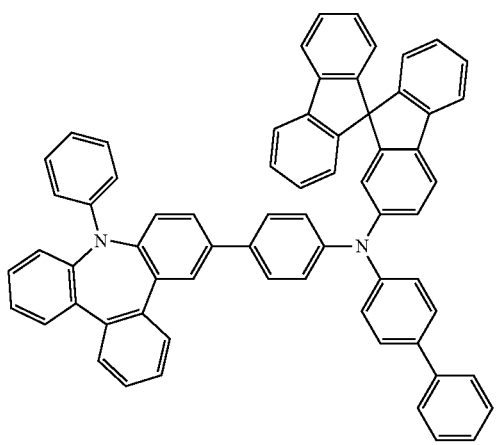
38
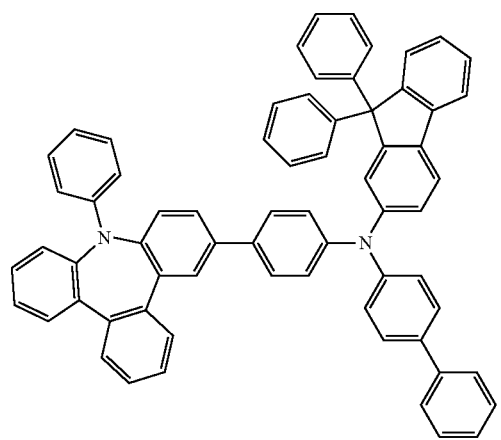

-continued
39
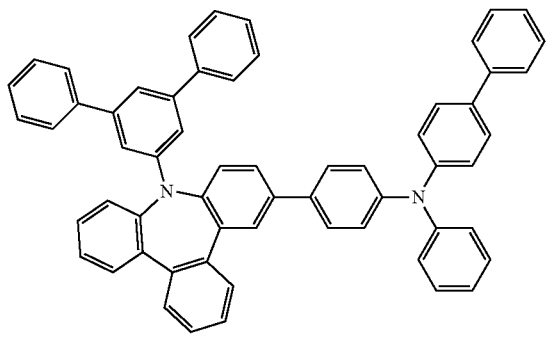
40
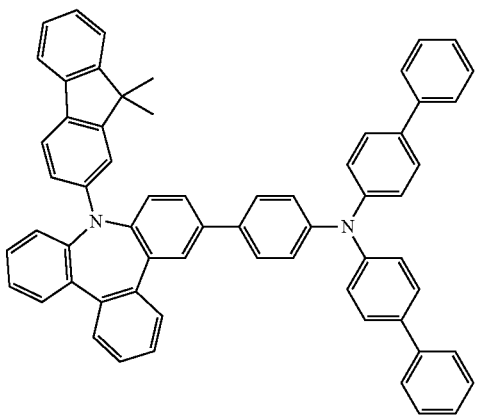
41
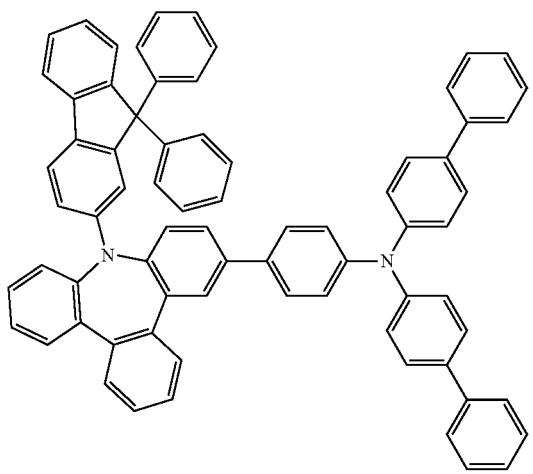
42
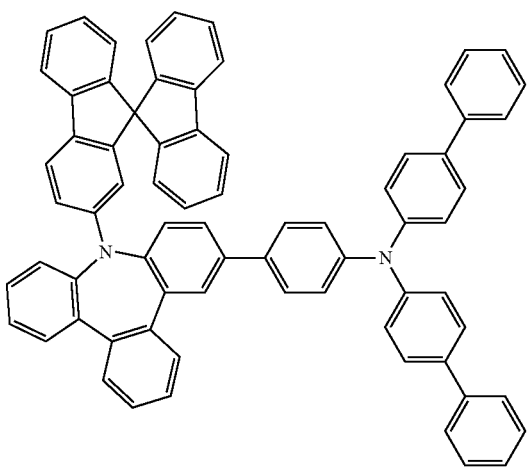
43
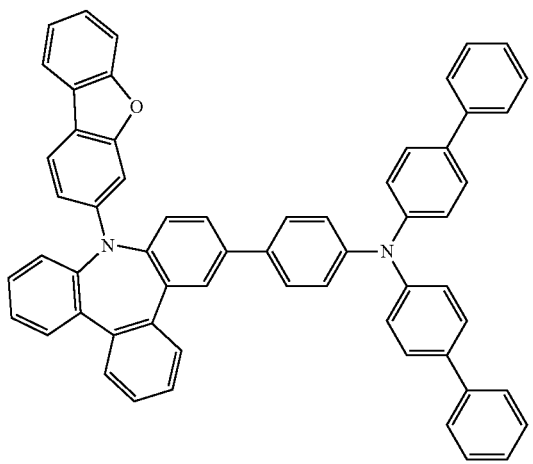
44
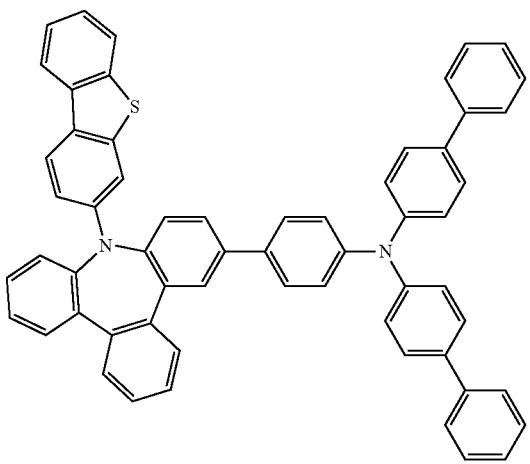

45
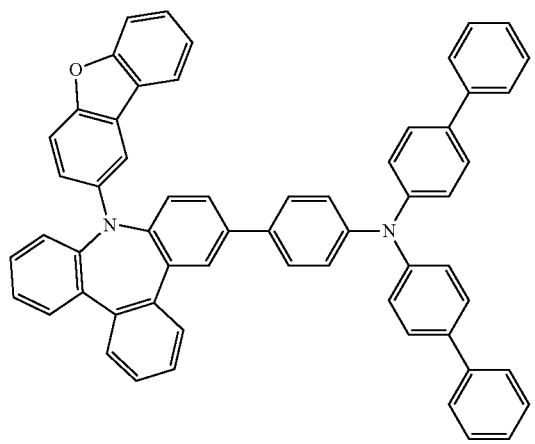
46
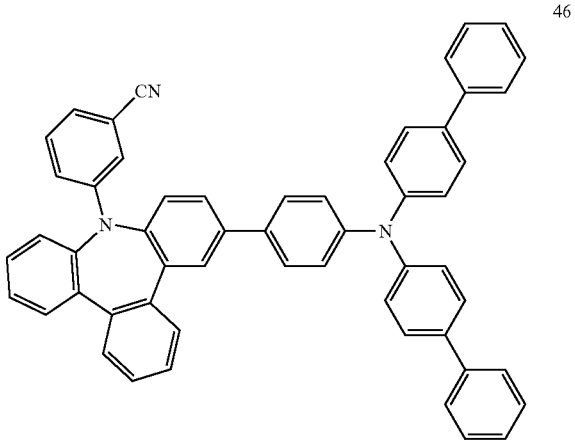
47
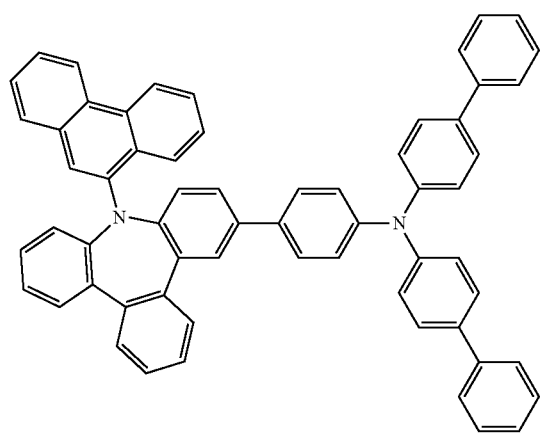
48
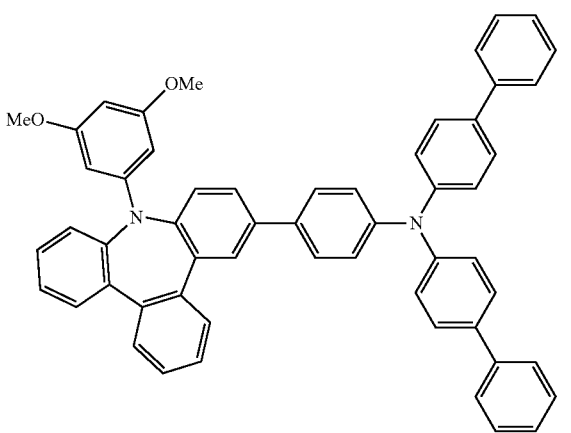
49
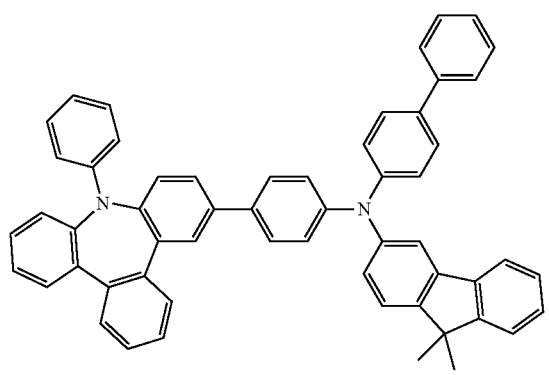
50
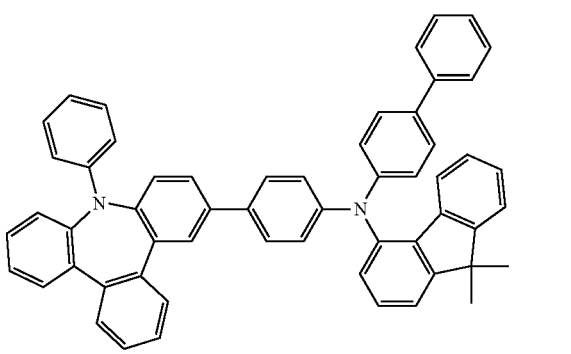
51
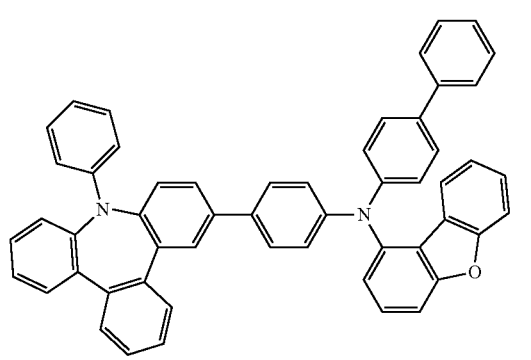
52
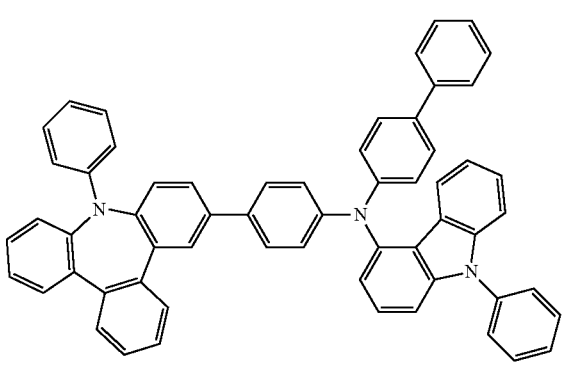

-continued
53
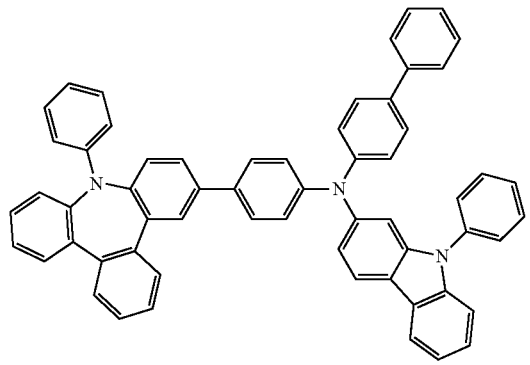
54
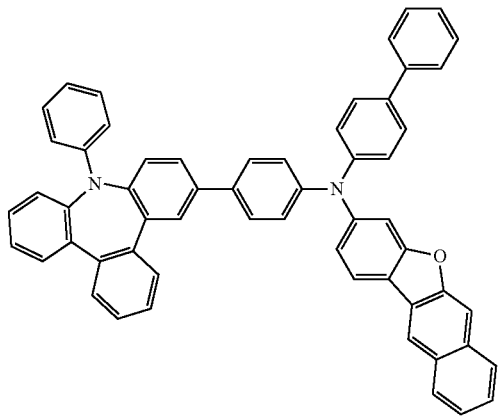
55
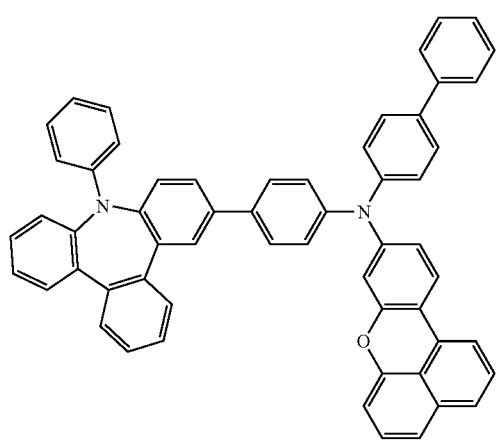
56
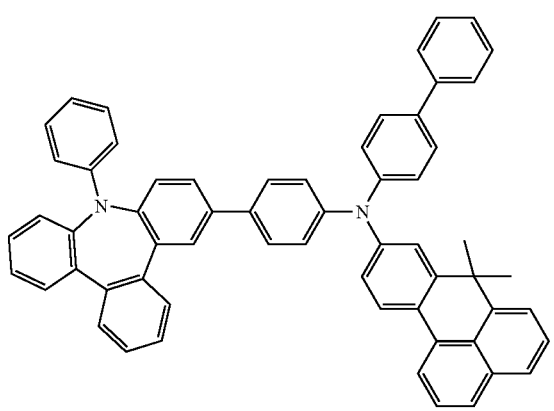
57
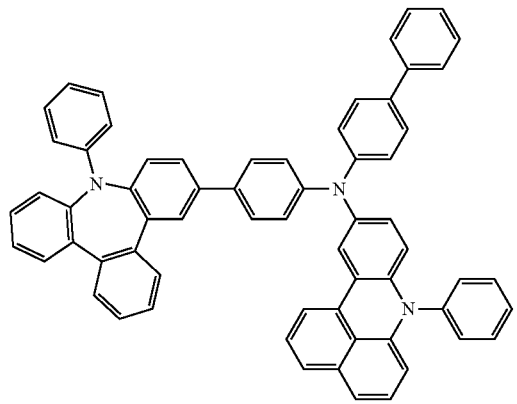
58
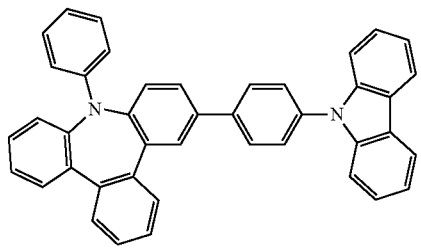
59
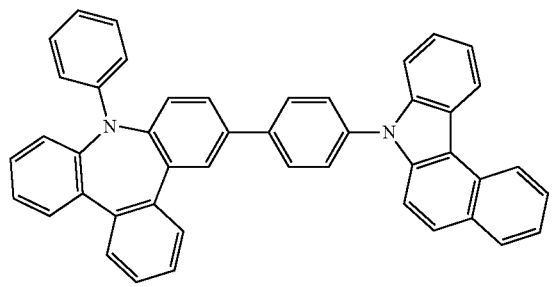
60
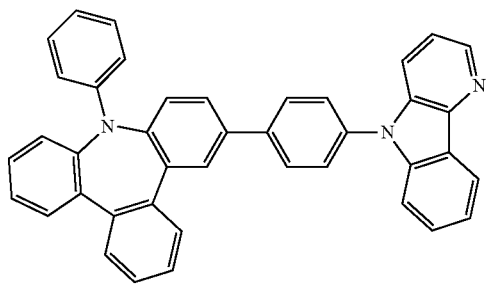

-continued
61 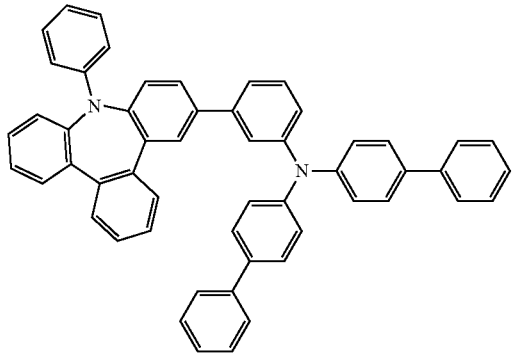
62 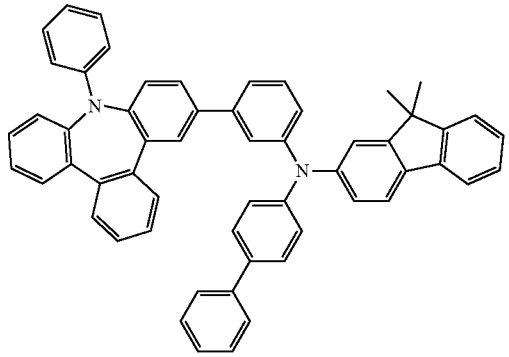
63 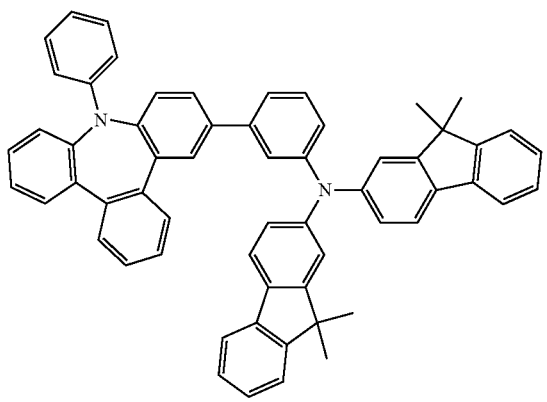
64 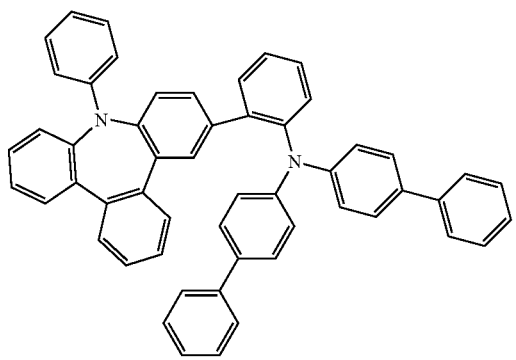
65 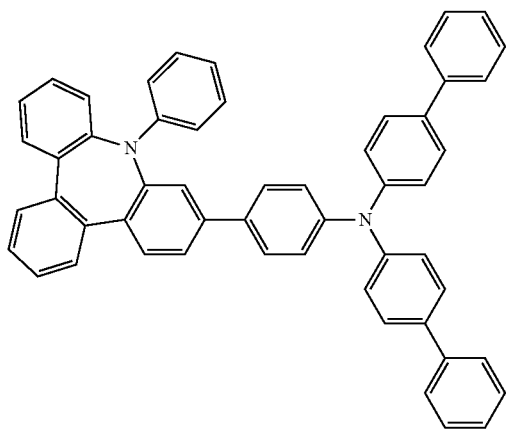
66 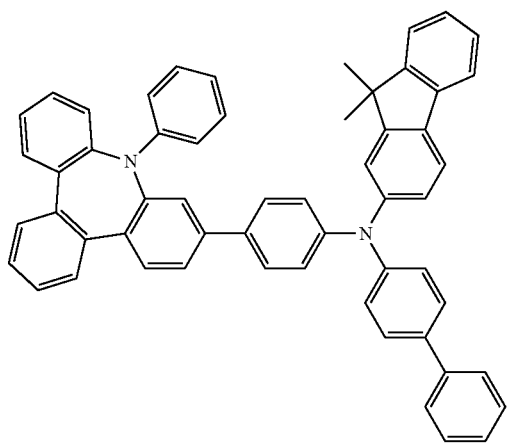
67 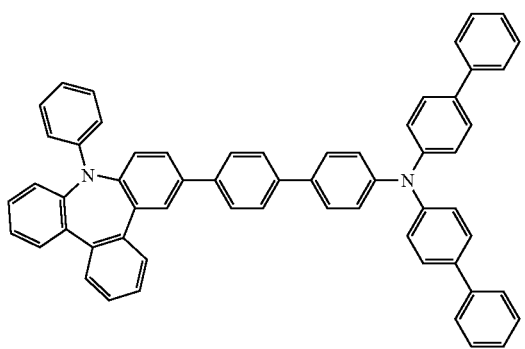
68 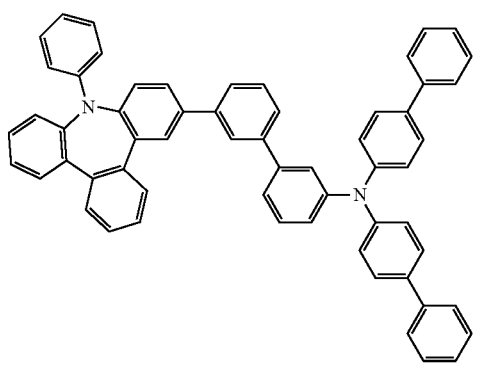

69
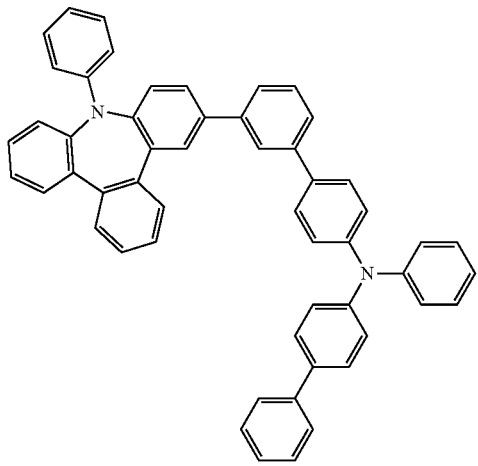
70
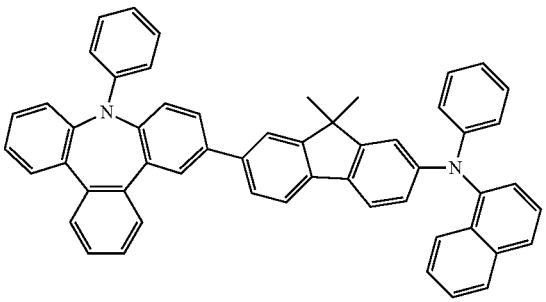
71
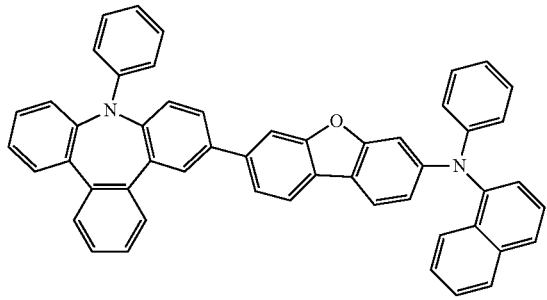
72
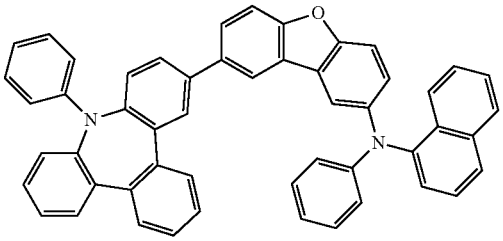
73
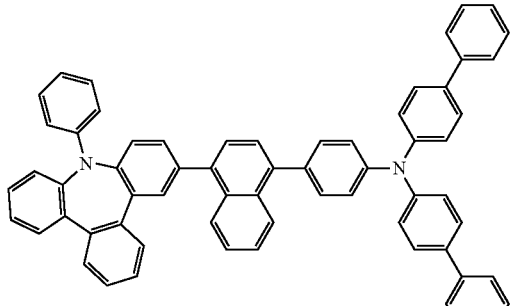
74
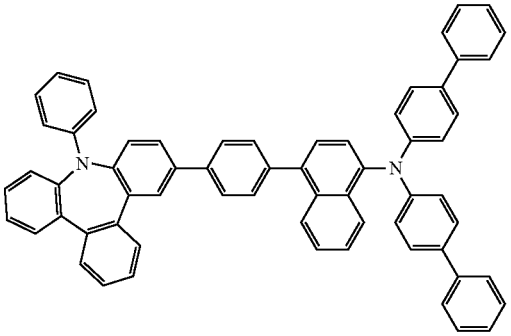
75
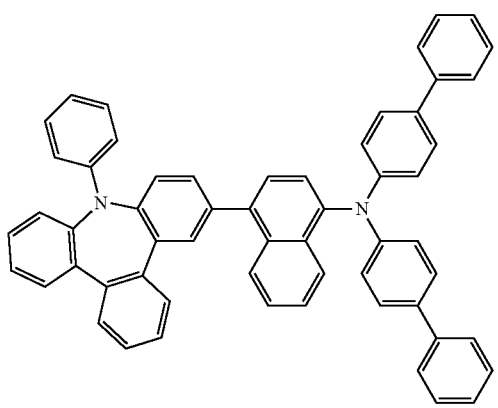
76
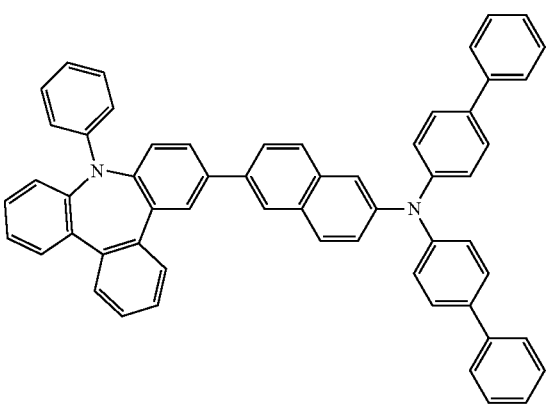

-continued
77
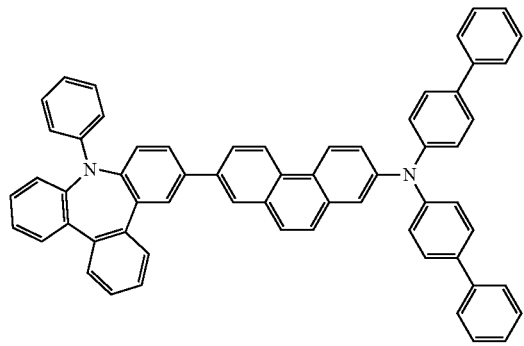
78
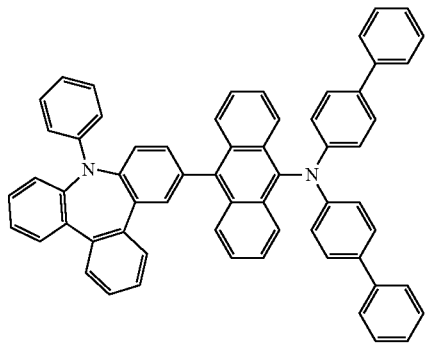
79
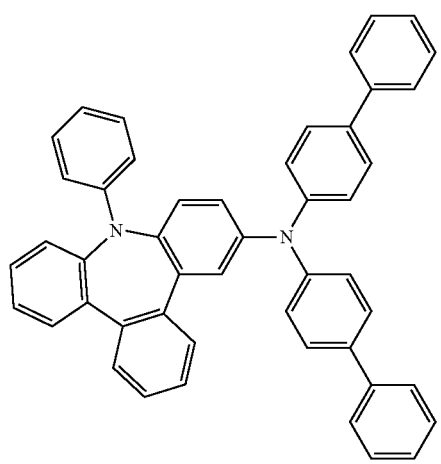
80
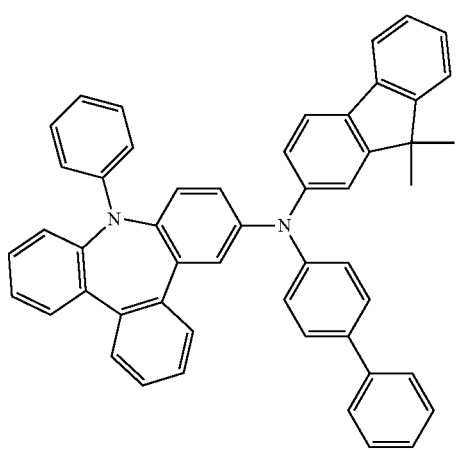
81
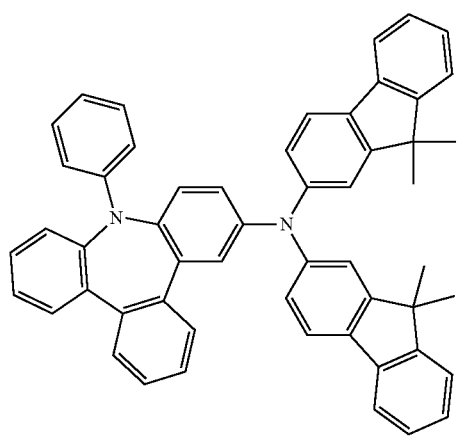
82
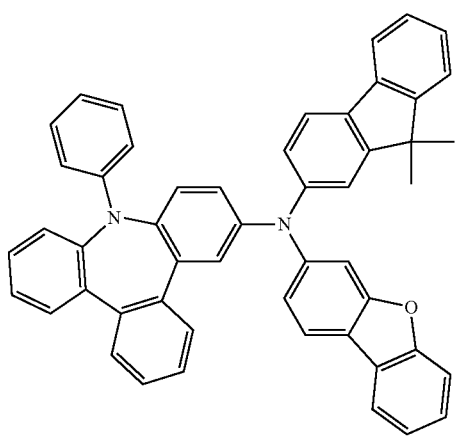

-continued
83
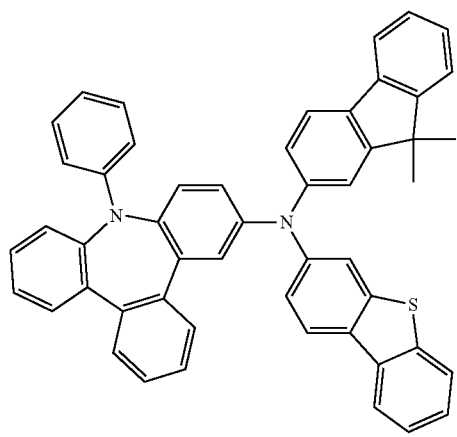
84
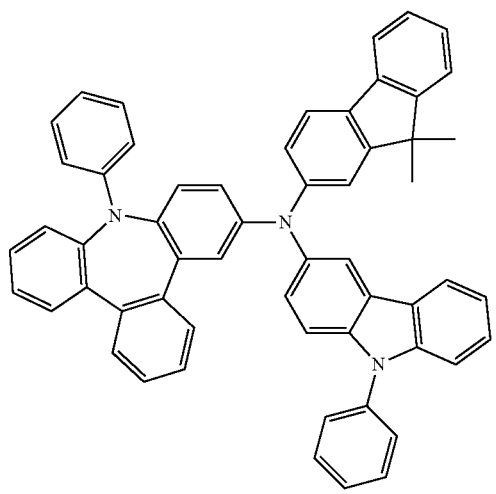
85
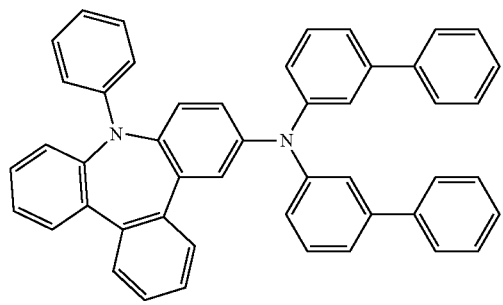
86
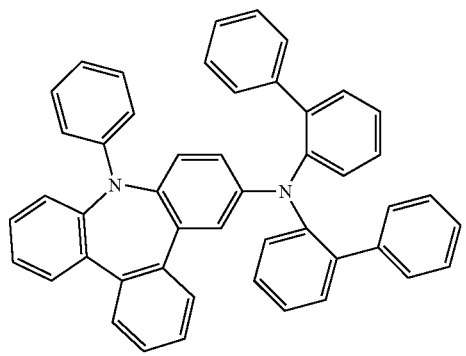
87
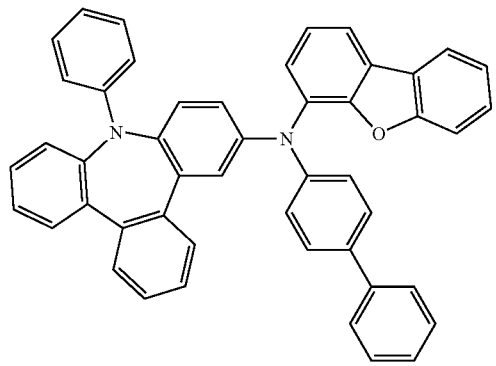
88
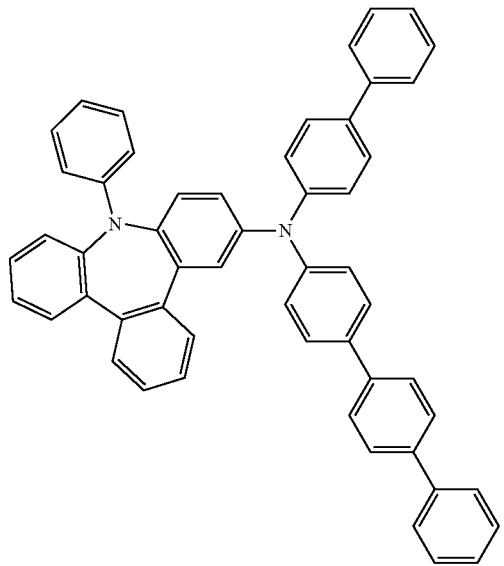

-continued
89
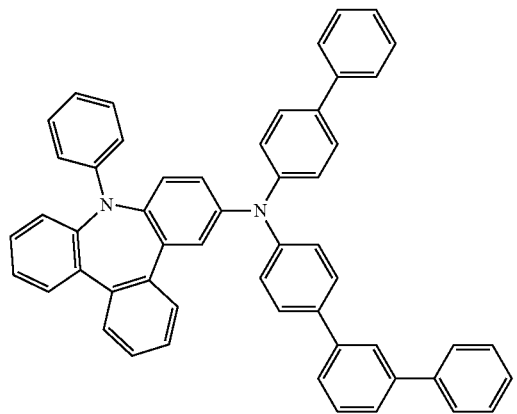
90
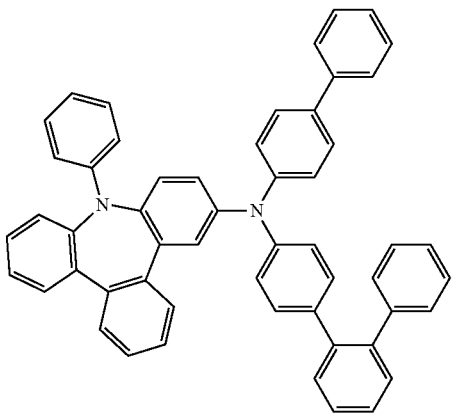
91
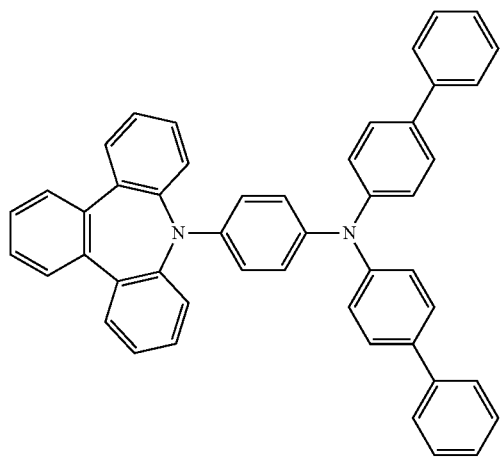
92
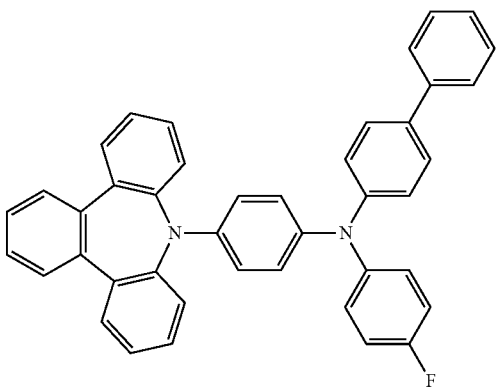
93
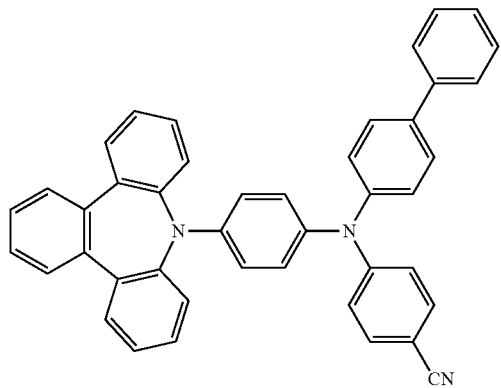
94
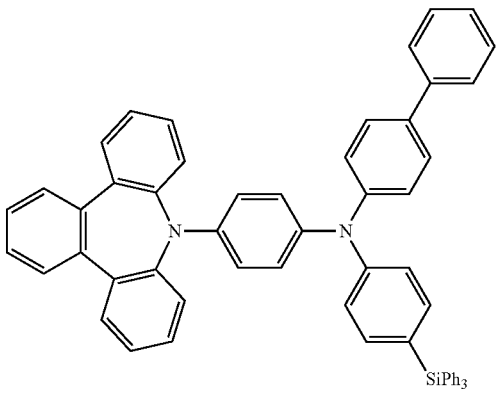

-continued
95
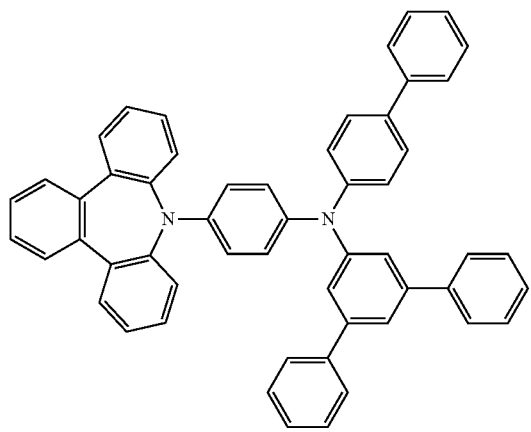
96
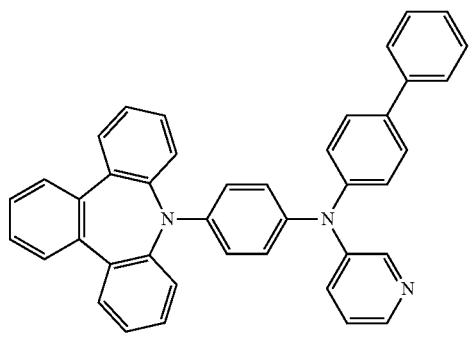
97
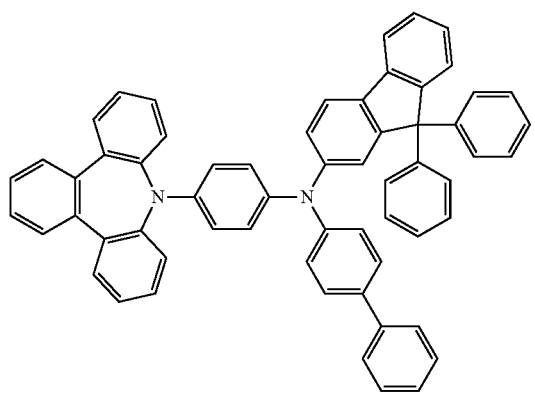
98
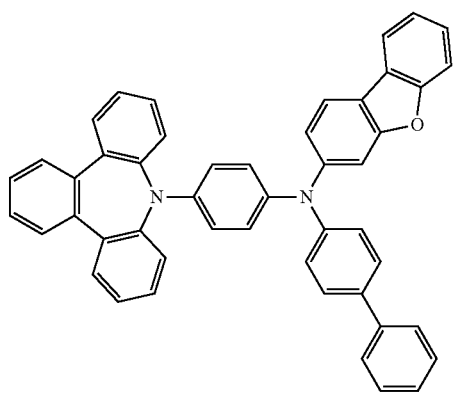
99
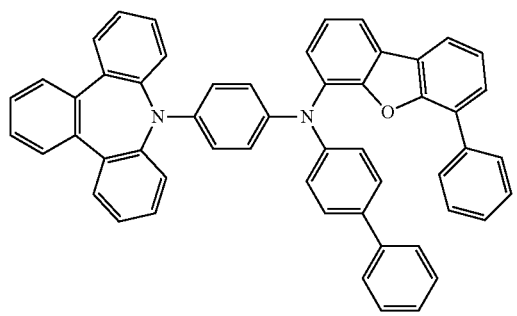
100
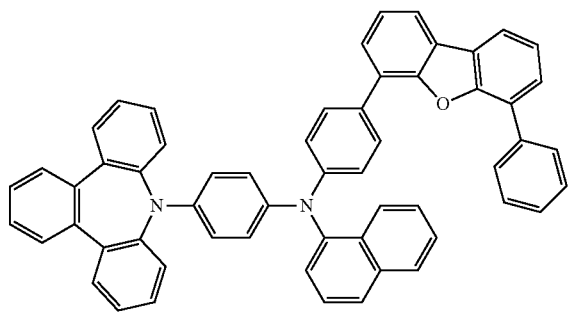
101
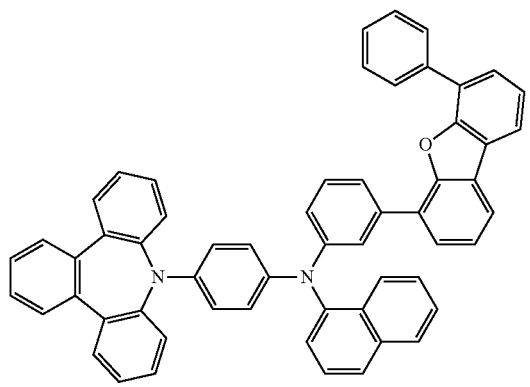
102
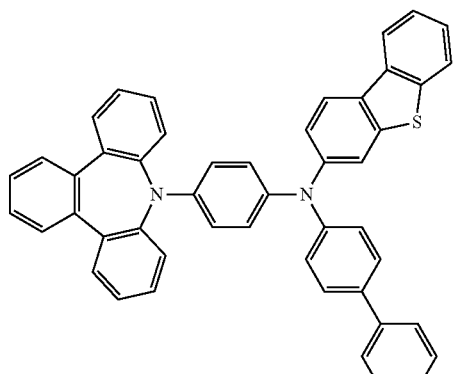

-continued
103
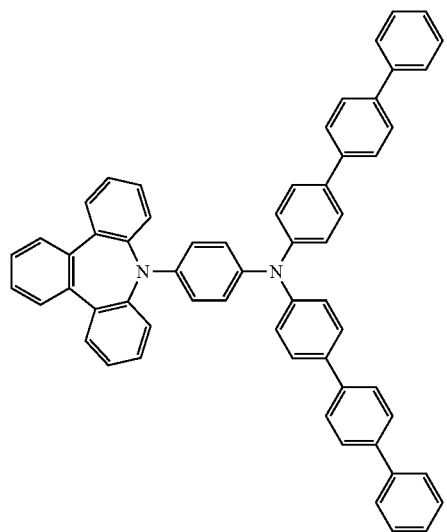
104
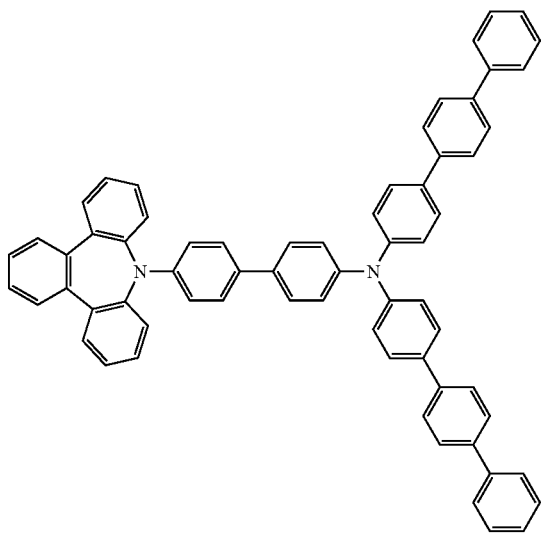
105
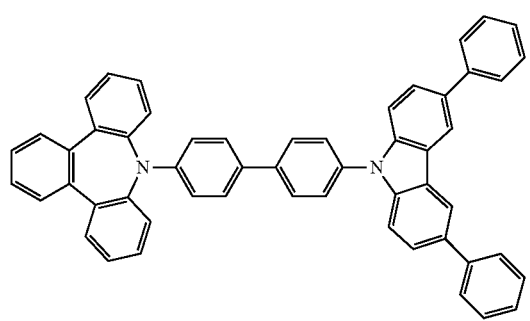
106
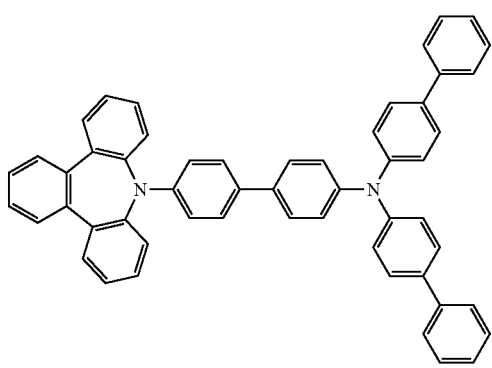
107
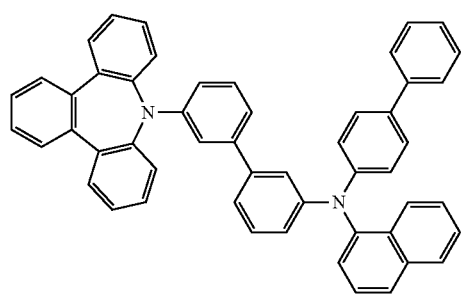
108
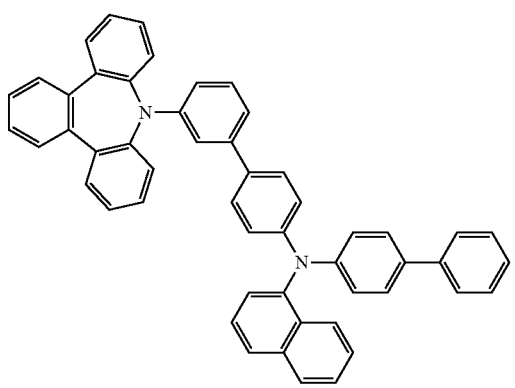

109
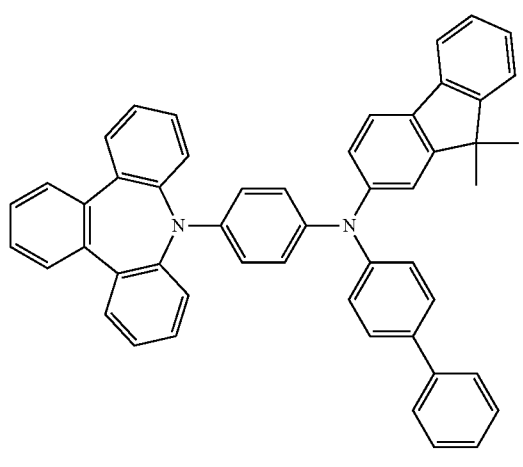
110
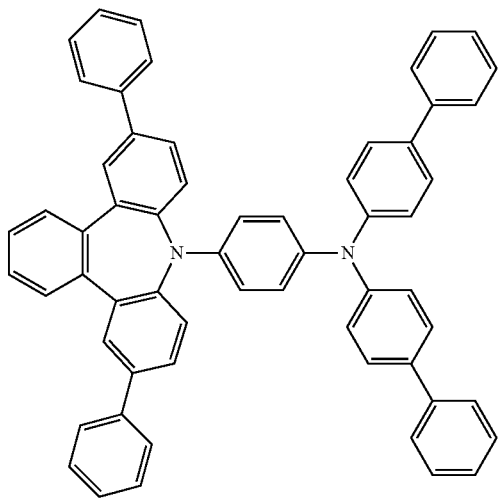
111
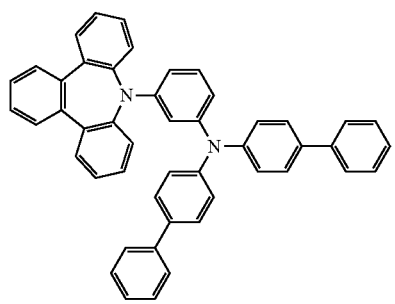
112
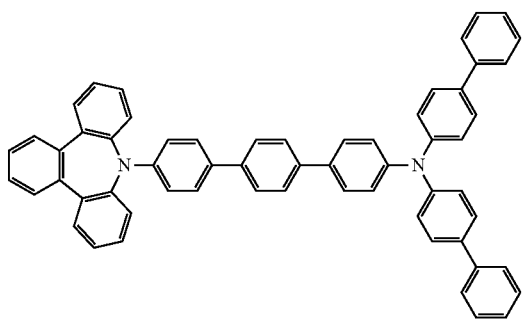
113
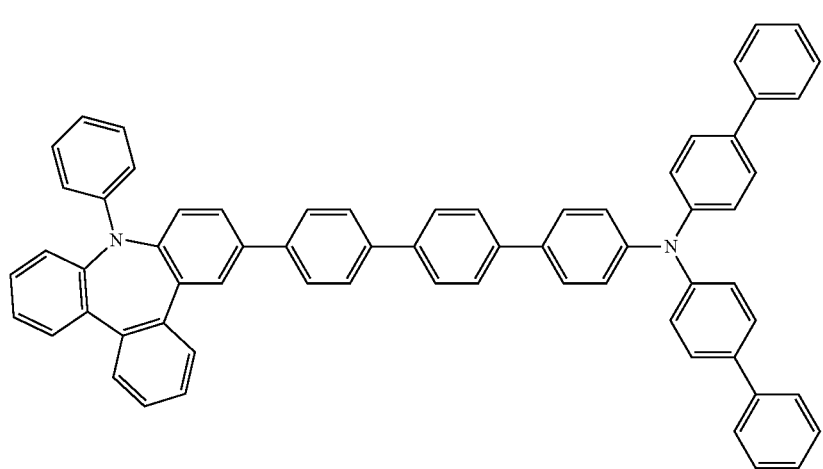

-continued
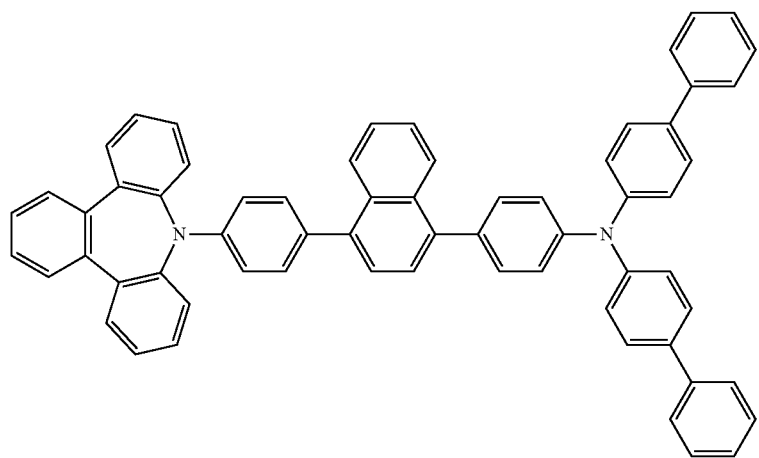
114
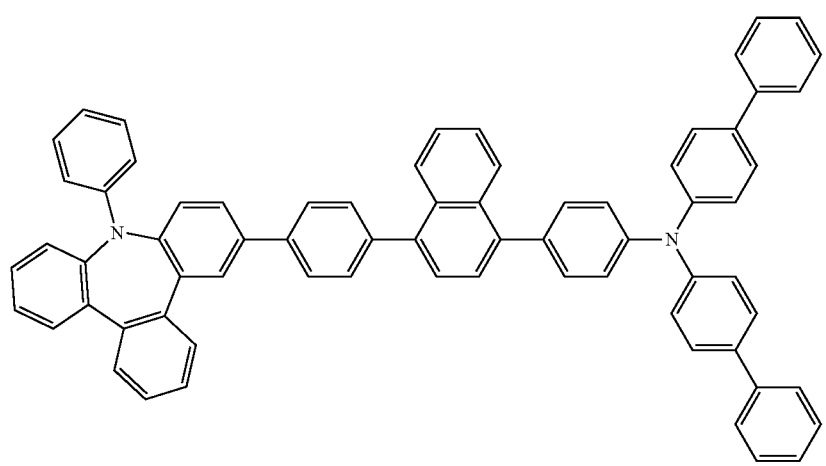
115
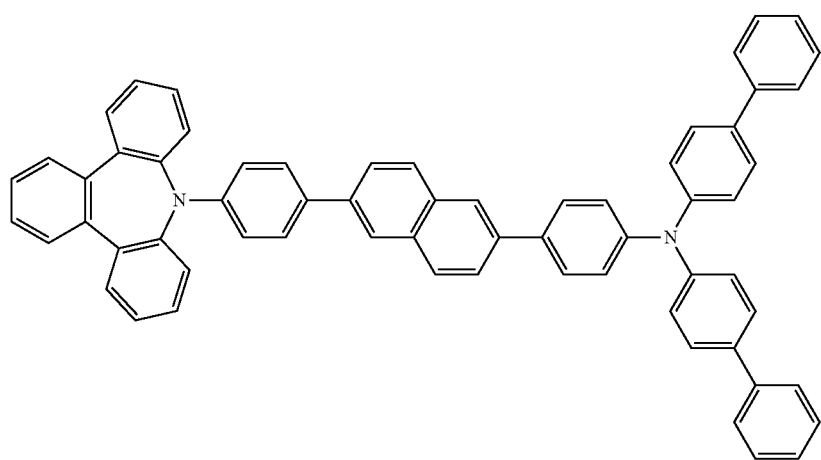
116

117

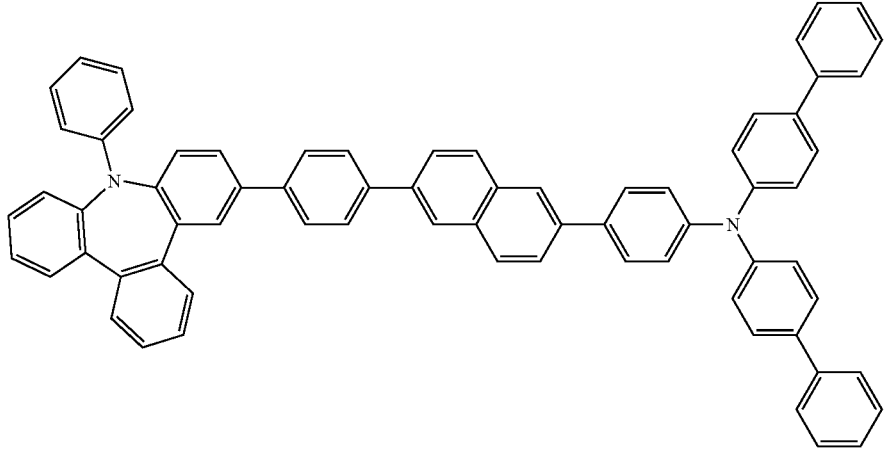

The term "organic layer" used herein may refer to a single layer and/or a plurality of layers disposed (e.g., positioned) between the first electrode and the second electrode of an organic light-emitting device. A material included in the "organic layer" is not limited to an organic material.

The drawing is a schematic view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described in connection with the drawing.

In the drawing, a substrate may be additionally disposed under the first electrode 110 or above the second electrode 190. The substrate may be a glass substrate and/or a transparent plastic substrate, each having excellent mechanical strength, thermal stability, transparency, surface smoothness, ease of handling, and/or water-resistance.

The first electrode 110 may be formed by depositing or sputtering a material for forming the first electrode 110 on the substrate. When the first electrode 110 is an anode, the material for forming the first electrode 110 may be selected from materials with a high work function so as to facilitate hole injection. The first electrode 110 may be a reflective electrode, a semi-transmissive electrode, or a transmissive electrode. The material for forming the first electrode 110 may be a transparent and highly conductive material, and non-limiting examples of such material include indium tin oxide (ITO), indium zinc oxide (IZO), tin oxide ($SnO_2$), and zinc oxide (ZnO). When the first electrode 110 is a semi-transmissive electrode or a reflective electrode, at least one of magnesium (Mg), aluminum (Al), aluminum-lithium (Al—Li), calcium (Ca), magnesium-indium (Mg—In), and magnesium-silver (Mg—Ag) may be used as a material for forming the first electrode 110.

The first electrode 110 may have a single-layer structure, or a multi-layer structure including two or more layers. For example, the first electrode 110 may have a three-layered structure of ITO/Ag/ITO, but the structure of the first electrode 110 is not limited thereto.

The organic layer 150 may be disposed on the first electrode 110, and the second electrode 190 may be disposed on the organic layer 150.

The organic layer 150 may include an emission layer and may further include a hole transport region disposed between the first electrode and the emission layer, and an electron transport region disposed between the emission layer and the second electrode.

In various embodiments, the hole transport region may include at least one selected from a hole transport layer (HTL), a hole injection layer (HIL), and an electron blocking layer; and an electron transport region may include at least one selected from a hole blocking layer (HBL), an electron transport layer (ETL), and an electron injection layer (EIL). However, it may be understood that embodiments of the present disclosure are not limited thereto.

The hole transport region may have a single-layered structure formed of a single material, a single-layered structure formed of a plurality of different materials, or a multi-layered structure having a plurality of layers formed of a plurality of different materials.

The hole transport layer may include a first hole transport layer and a second hole transport layer.

In some embodiments, the first hole transport layer may include the compound of Formula 1 according to an embodiment of the present disclosure.

For example, the hole transport region may have a single-layered structure formed of a plurality of different materials, or a structure of hole injection layer/hole transport layer, a structure of hole injection layer/first hole transport layer/second hole transport layer, a structure of hole injection layer/first hole transport layer/second hole transport layer/electron blocking layer, or a structure of hole injection layer/hole transport layer/electron blocking layer, wherein the layers of each structure are sequentially stacked from the first electrode 110 in this stated order, but the structure of the hole transport region is not limited thereto.

When the hole transport region includes a hole injection layer, the hole injection layer may be formed on the first electrode 110 by using one or more suitable methods such as vacuum deposition, spin coating, casting, a Langmuir-Blodgett (LB) method, ink-jet printing, laser-printing, and/or laser-induced thermal imaging.

When a hole injection layer is formed by vacuum deposition, for example, the vacuum deposition may be performed at a deposition temperature of about 100 to about 500° C., at a vacuum degree of about $10^{-8}$ to about $10^{-3}$ torr, and at a deposition rate of about 0.01 to about 100 Å/sec, by taking into account a compound for forming the hole injection layer to be deposited, and the structure of the hole injection layer to be formed.

When a hole injection layer is formed by spin coating, for example, the spin coating may be performed at a coating rate of about 2,000 rpm to about 5,000 rpm, and at a temperature of about 80° C. to 200° C., by taking into account a compound for forming the hole injection layer to be deposited, and the structure of the hole injection layer to be formed.

When the hole transport region includes a hole transport layer, the hole transport layer may be formed on the first electrode 110 or the hole injection layer by using one or more suitable methods such as vacuum deposition, spin coating, casting, a LB method, ink-jet printing, laser-printing, and/or laser-induced thermal imaging. When the hole transport layer is formed by vacuum deposition and/or spin coating, deposition and coating conditions for the hole transport layer may be the same as (or substantially similar to) the deposition and coating conditions for the hole injection layer.

In various embodiments, the first hole transport layer may include a compound represented by Formula 201A:

Formula 201A

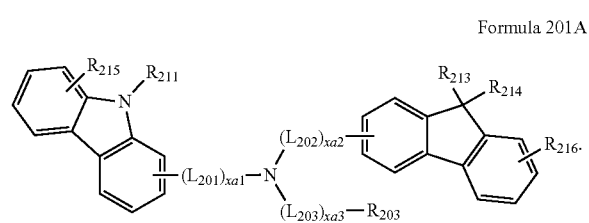

In Formula 201A, $L_{201}$ to $L_{203}$ may each independently be selected from the group consisting of:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may each independently be 0 or 1;

$R_{203}$ and $R_{211}$ may each independently be selected from the group consisting of:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may each independently be selected from the group consisting of:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and $R_{215}$ and $R_{216}$ may each independently be selected from the group consisting of:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

In various embodiments, $R_{211}$ in Formula 201A may be a substituted or an unsubstituted phenyl group, or a substituted or an unsubstituted pyridyl group.

In various embodiments, $R_{213}$ and $R_{214}$ in Formula 201A may each independently be a methyl group or a phenyl group.

In various embodiments, the compound of Formula 201A may be one of the following Compounds HT1 to HT33:

HT1

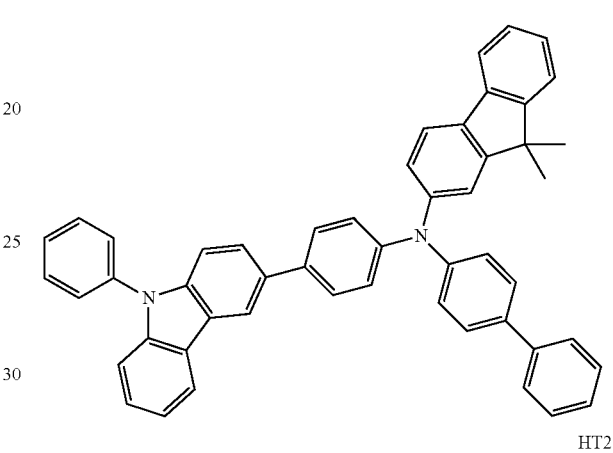

HT2

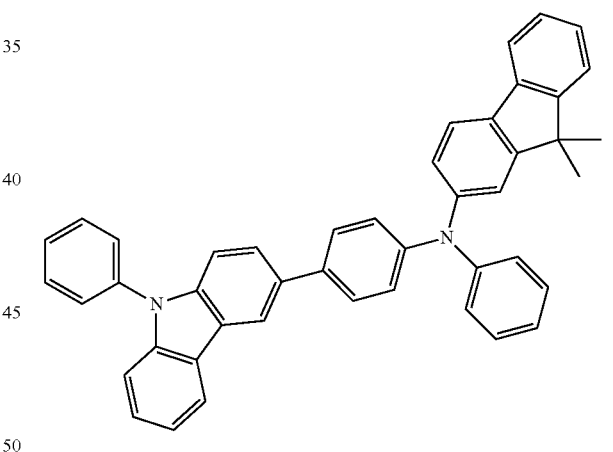

HT3

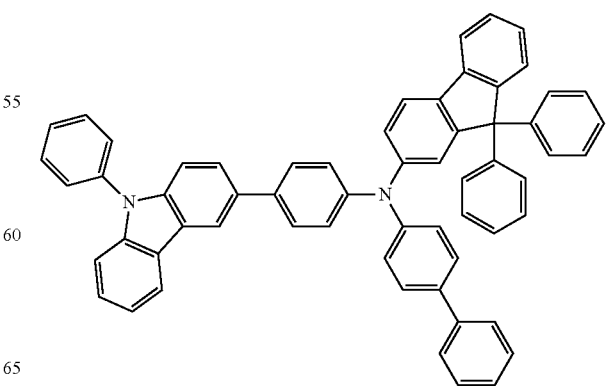

HT4
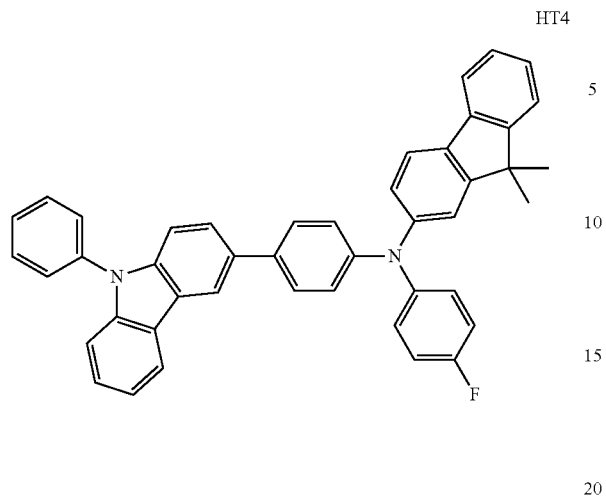
HT5
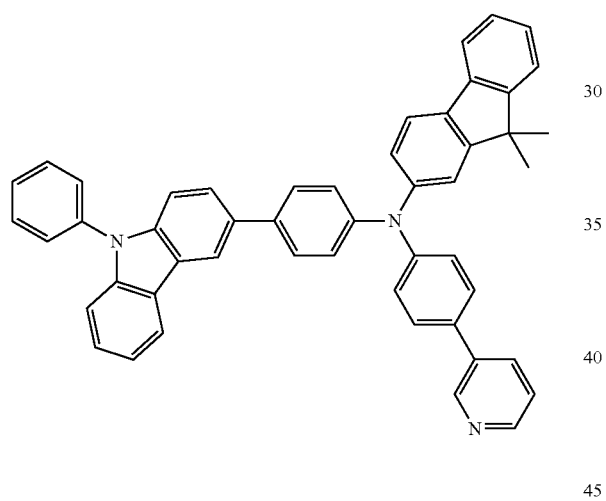
HT6
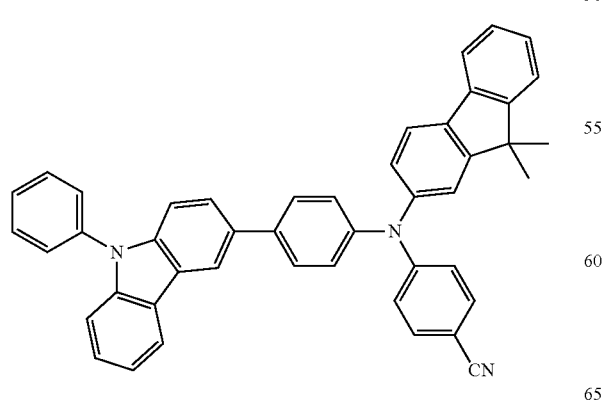
HT7
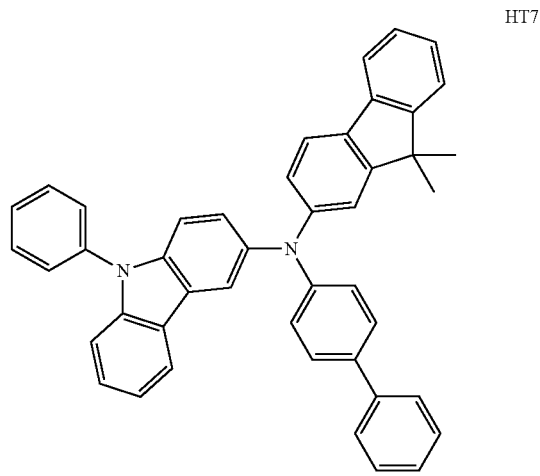
HT8
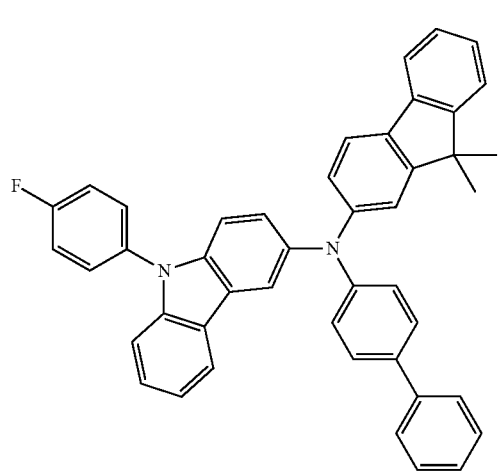
HT9
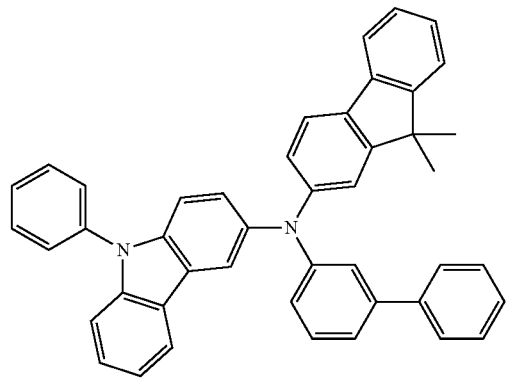

HT10
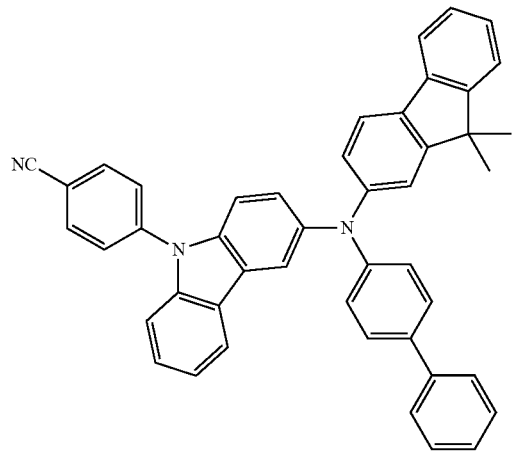
HT13
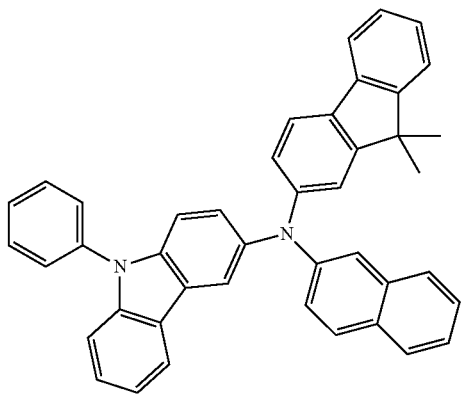
HT11
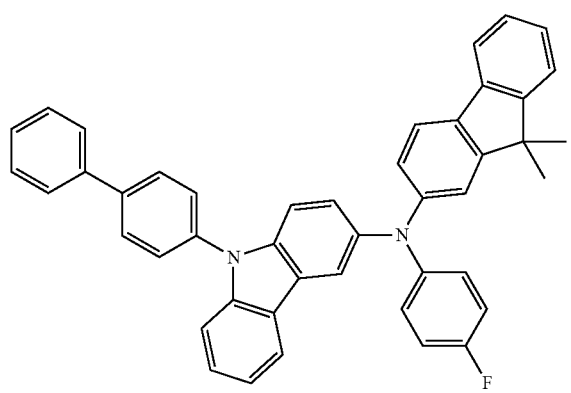
HT14
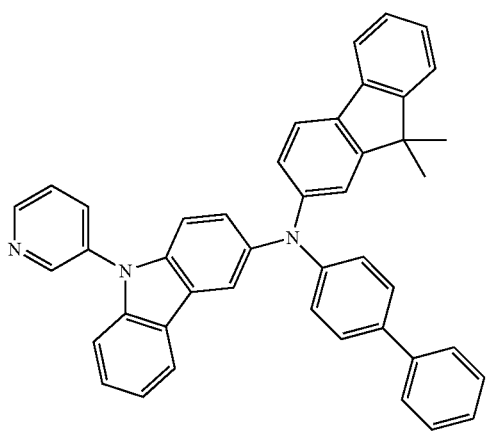
HT12
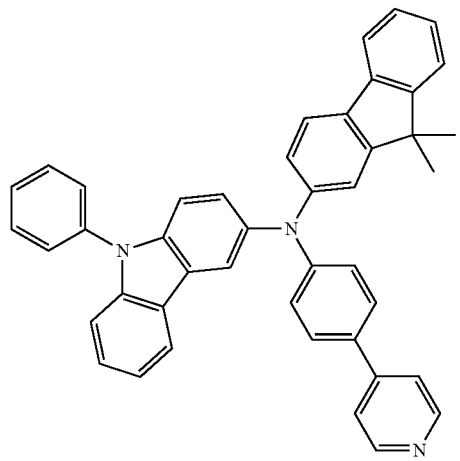
HT15
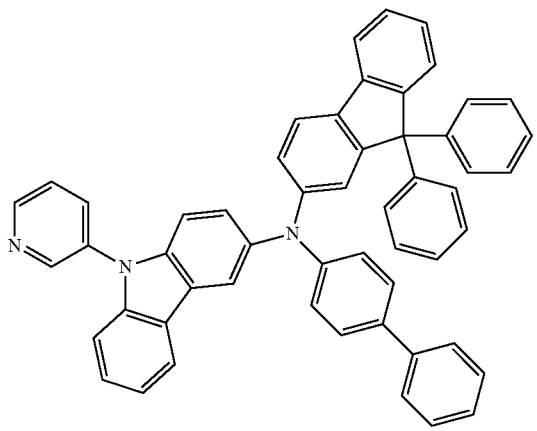

-continued
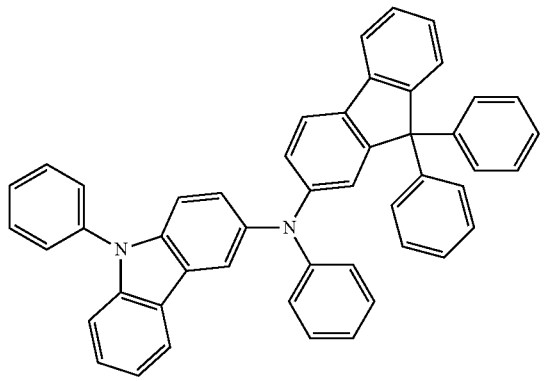
HT16
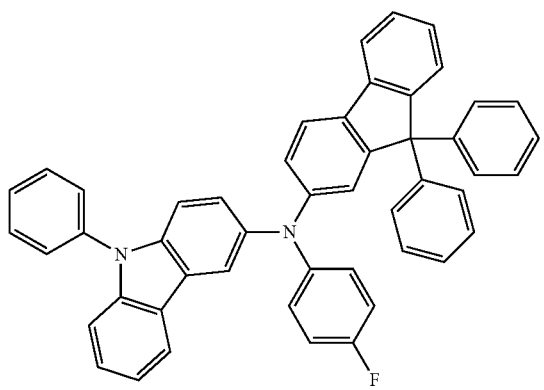
HT17
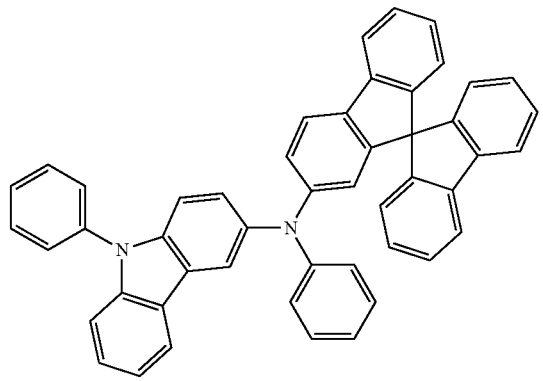
HT18
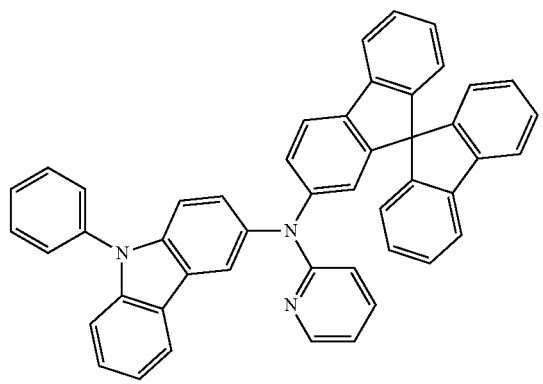
HT19
-continued
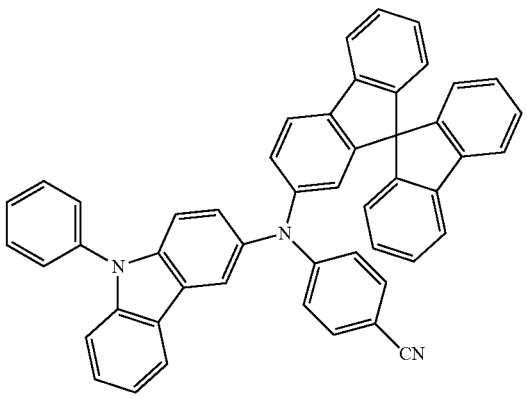
HT20
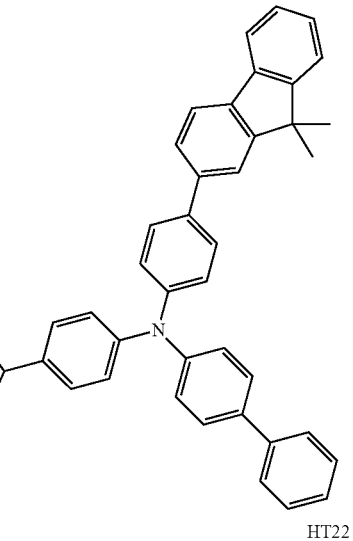
HT21
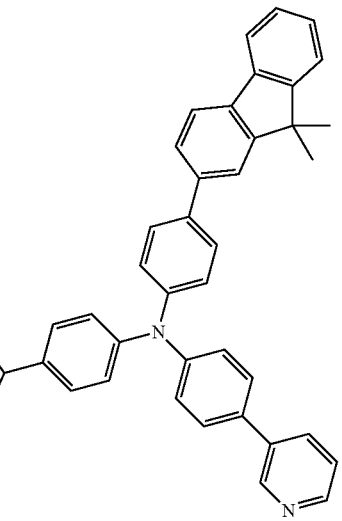
HT22

HT23
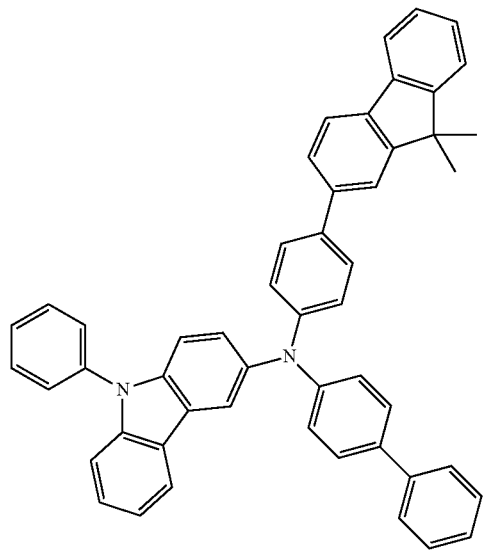
HT24
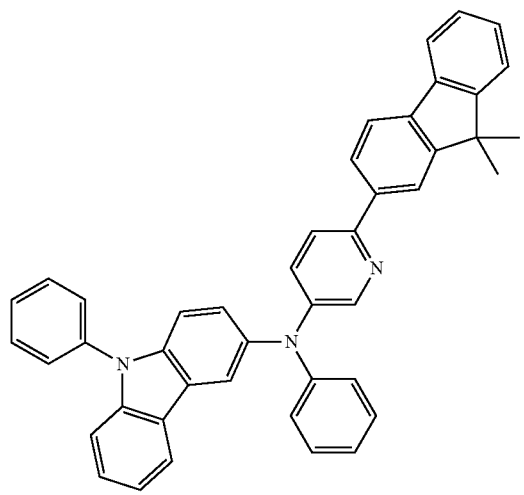
HT25
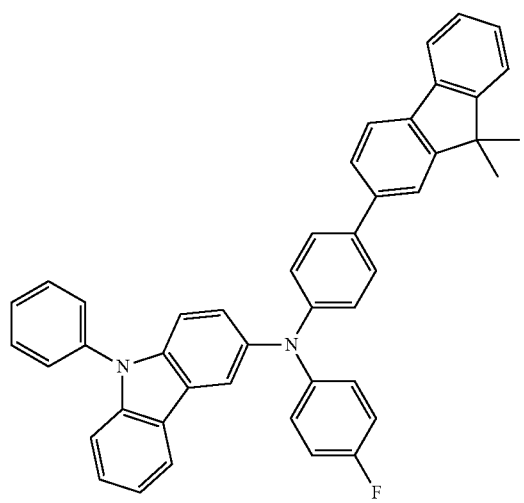
HT26
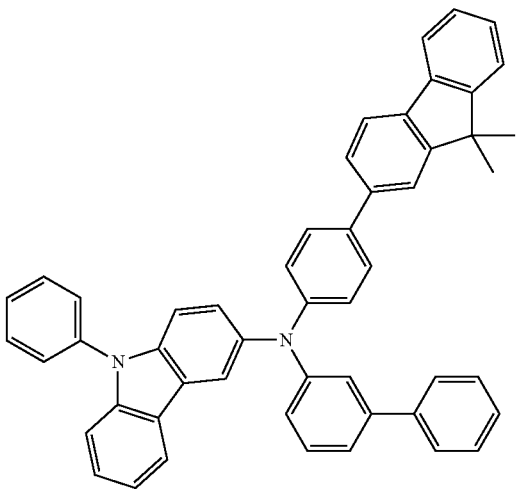
HT27
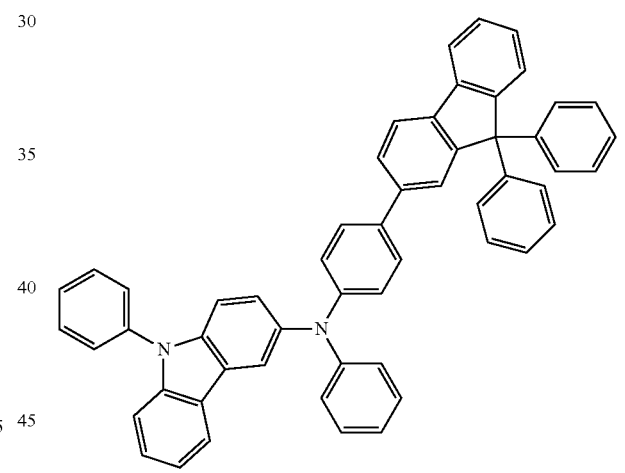
HT28
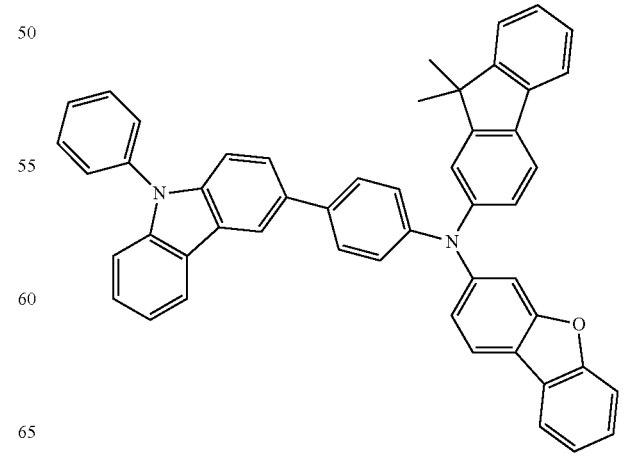

HT29

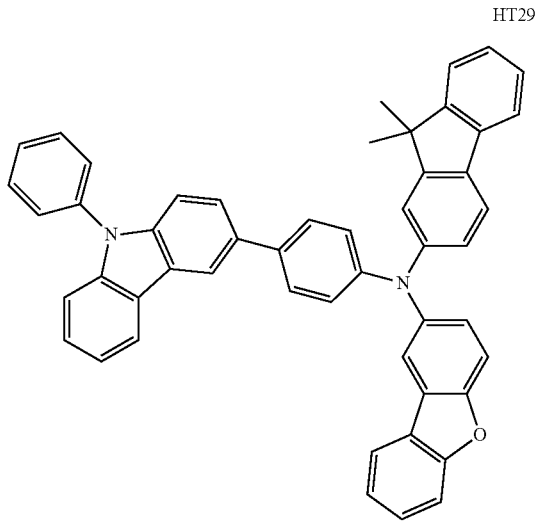

HT30

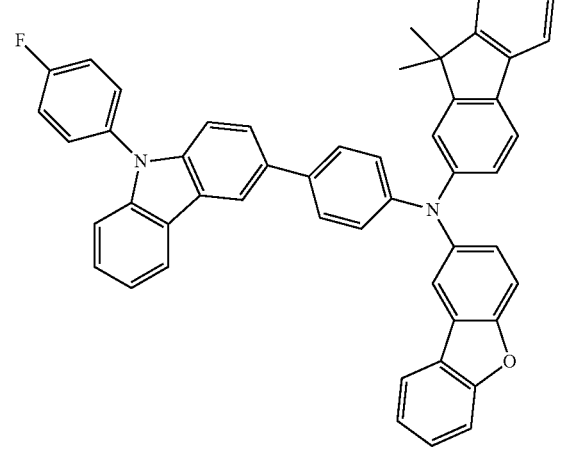

HT31

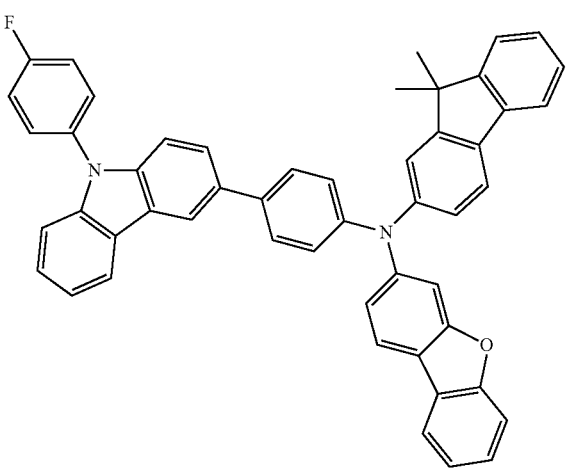

HT32

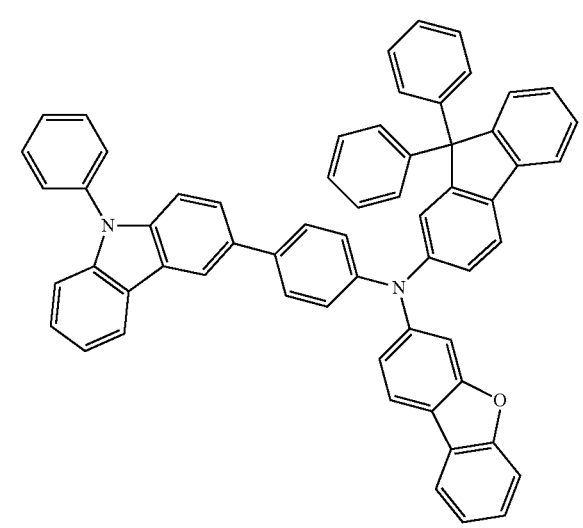

HT33

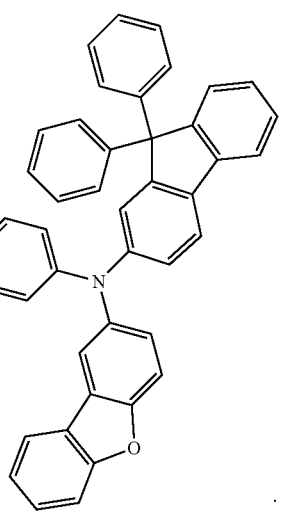

In various embodiments, the second hole transport region may include the compound of Formula 1 according to an embodiment of the present disclosure.

A thickness of the hole transport region may be in a range of about 100 Å to about 10,000 Å, for example, about 100 Å to about 2,000 Å. When the hole transport region includes a hole injection layer and a hole transport layer, the thickness of the hole injection layer may be in a range of about 100 Å to about 10,000 Å, for example, about 100 Å to about 1,000 Å, and the thickness of the hole transport layer (that is, the sum of the thicknesses of the first hole transport layer and the second hole transport layer) may be in a range of about 50 Å to about 2,000 Å, for example, about 100 Å to about 1,500 Å. When the thicknesses of the hole transport region, the hole injection layer, and the hole transport layer are within any of these ranges, satisfactory (or suitable) hole transporting characteristics may be obtained without a substantial increase in driving voltage.

The hole transport region may further include, in addition to the materials described above, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant include quinone derivatives (such as tetracyanoquinonedimethane (TCNQ) and/or 2,3,5,6-tetrafluoro-tetracyano-1,4-benzoquinonedimethane (F4-TCNQ)); metal oxides (such as tungsten oxide and/or molybdenum oxide), and Compound HT-D1 illustrated below.

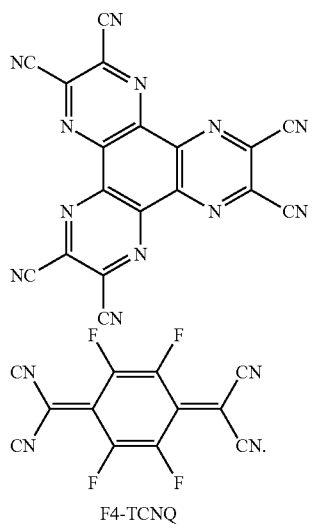

Compound HT-D1

F4-TCNQ

The hole transport region may further include a buffer layer and/or an electron blocking layer, in addition to a hole injection layer and/or a hole transport layer. Since the buffer layer may compensate for an optical resonance distance according to a wavelength of light emitted from the emission layer, light-emission efficiency of the formed organic light-emitting device may be improved. For use as a material included in the buffer layer, any of materials that are included in the hole transport region may be used. The electron blocking layer may function to prevent or reduce the injection of electrons from the electron transport region.

An emission layer may be formed on the first electrode 110 or the hole transport region by using one or more suitable methods such as vacuum deposition, spin coating, casting, a LB method, ink-jet printing, laser-printing, and/or laser-induced thermal imaging. When an emission layer is formed by vacuum deposition and/or spin coating, deposition and coating conditions for the emission layer may be the same as (or substantially similar to) those for the hole injection layer.

When the organic light-emitting device 10 is a full color organic light-emitting device, the emission layer may be patterned into a red emission layer, a green emission layer, and/or a blue emission layer, according to a sub pixel. In various embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

For example, the host may include at least one selected from TPBi, TBADN, ADN (herein also referred to as "DNA"), CBP, CDBP, and TCP:

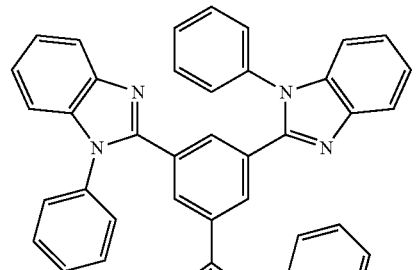

TPBi

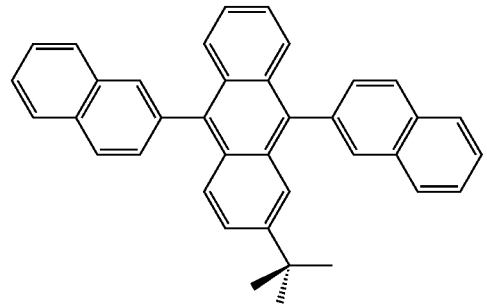

TBADN

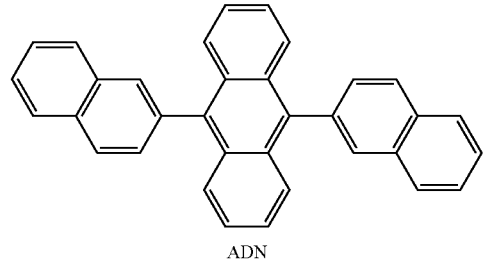

ADN

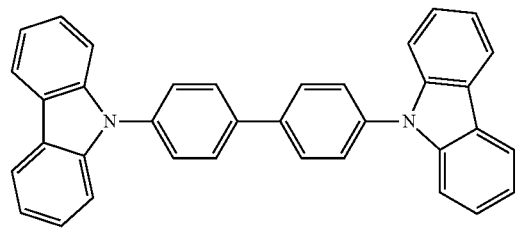

CBP

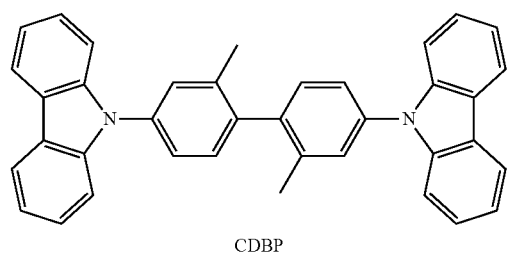

CDBP

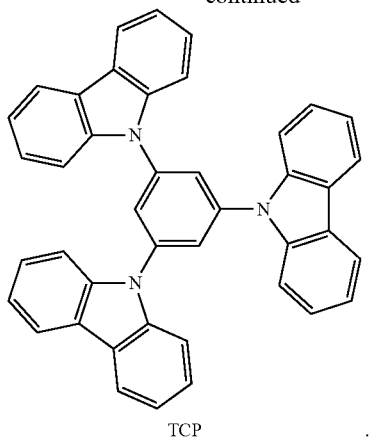

TCP

In various embodiments, the host may include a compound represented by Formula 301 below.

$$Ar_{301}\text{-}[(L_{301})_{xb1}\text{-}R_{301}]_{xb2}.$$  Formula 301

In Formula 301, $Ar_{301}$ may be selected from the group consisting of:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{301}$)($Q_{302}$)($Q_{303}$) (where $Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{301}$ may be selected from the group consisting of:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

$R_{301}$ may be selected from the group consisting of:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and xb2 may be selected from 1, 2, 3, and 4.

For example, in Formula 301, $L_{301}$ may be selected from the group consisting of a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from the group consisting of:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments of the present disclosure are not limited thereto.

For example, the host may include a compound represented by Formula 301A below:

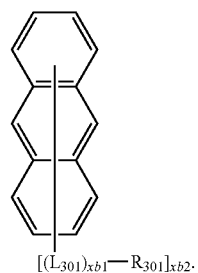

Formula 301A $[(L_{301})_{xb1}\!-\!R_{301}]_{xb2}$.

Descriptions of substituents of Formula 301A may be understood by referring to the descriptions thereof provided herein.

The compound represented by Formula 301 may include one of Compounds H1 to H42, but is not limited thereto:

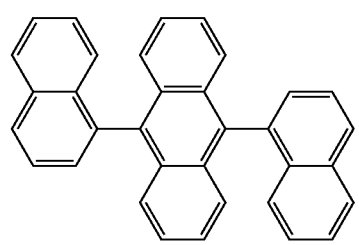

H1

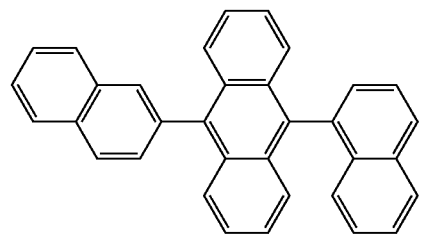

H2

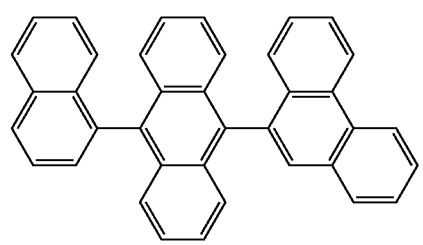

H3

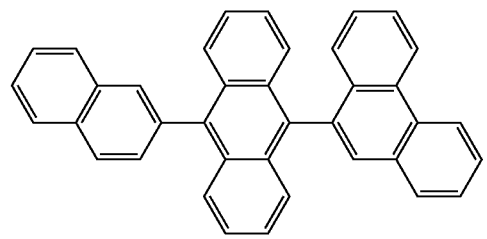

H4

H5
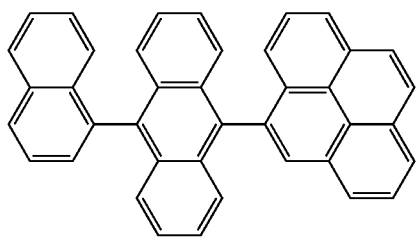
H6
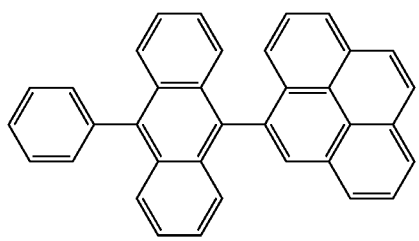
H7
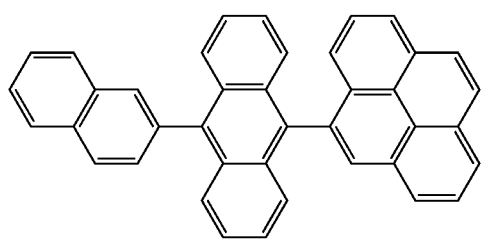
H8
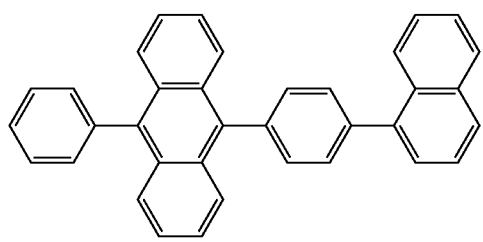
H9
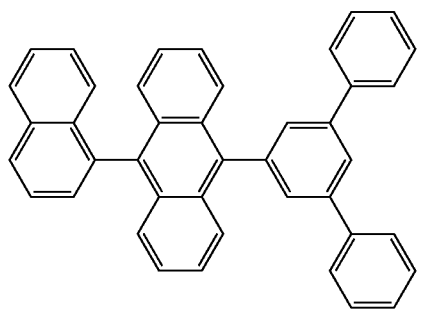
H10
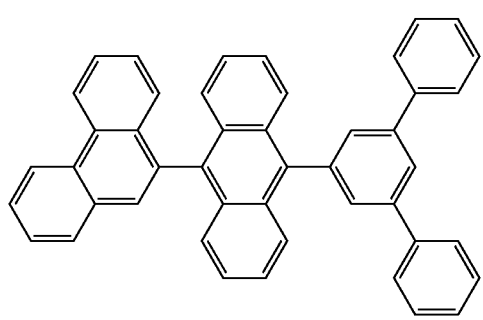
H11
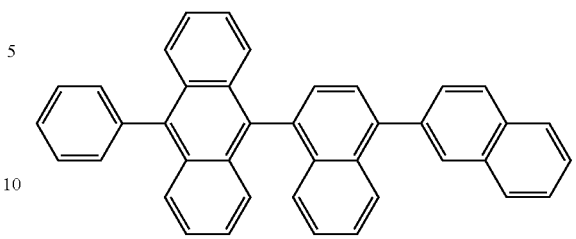
H12
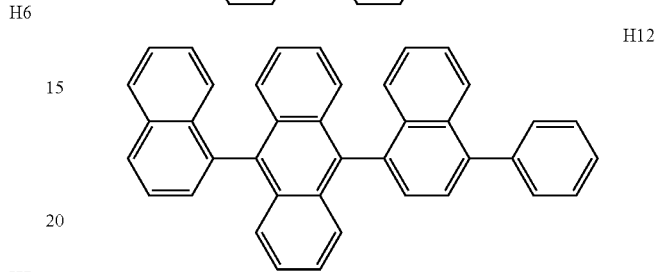
H13
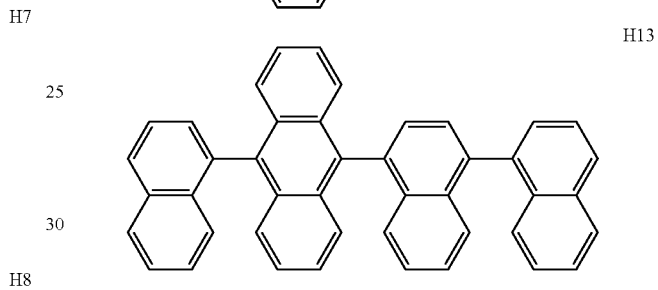
H14
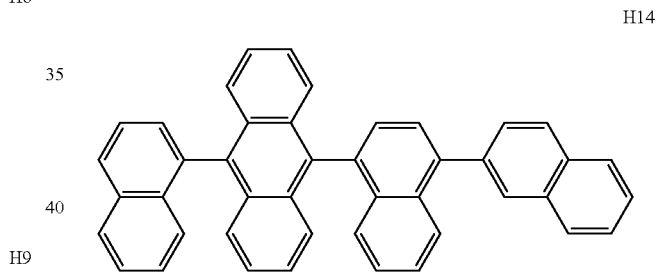
H15
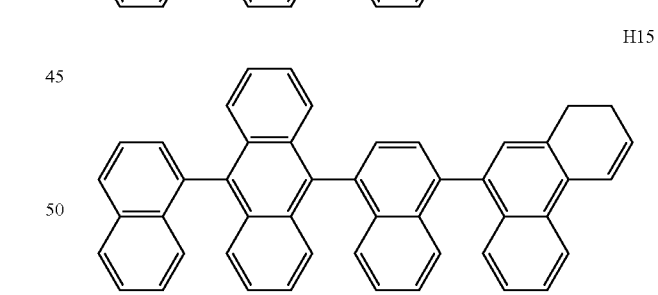
H16
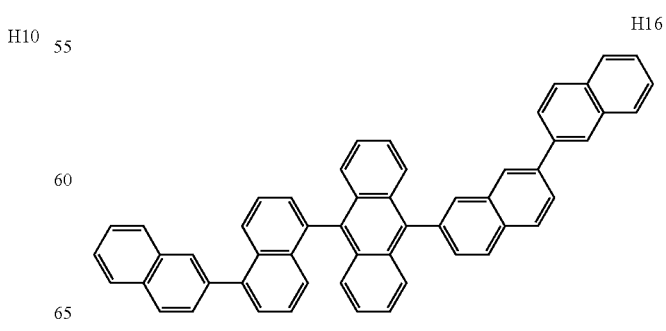

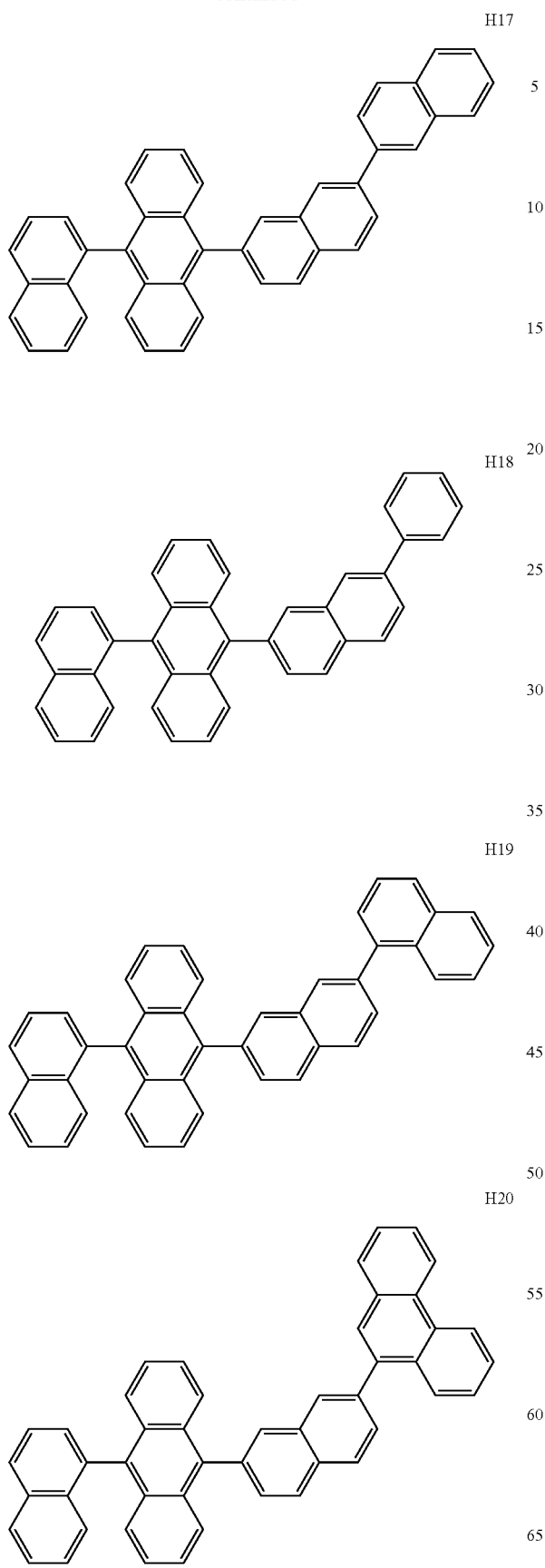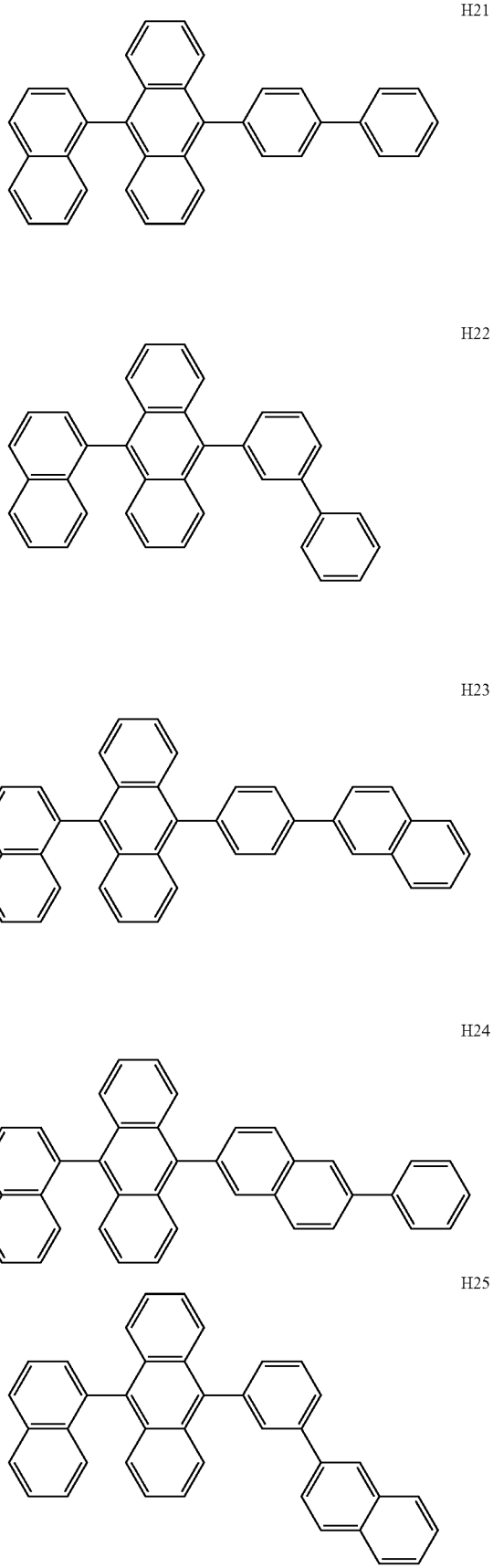

H26
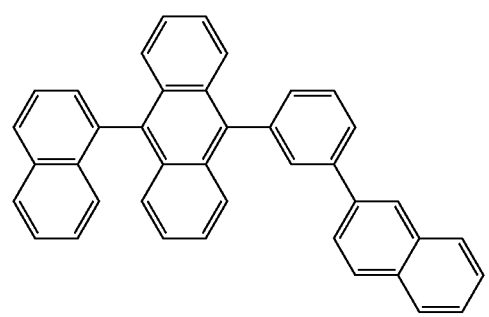
H27
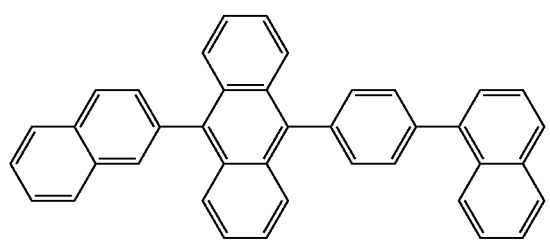
H28
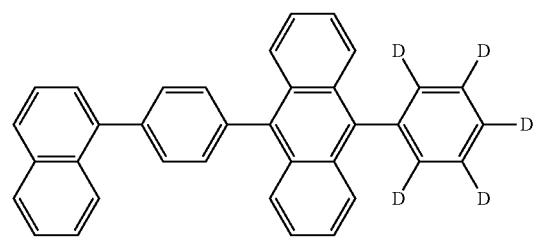
H29
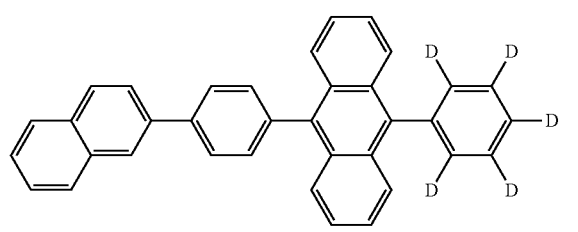
H30
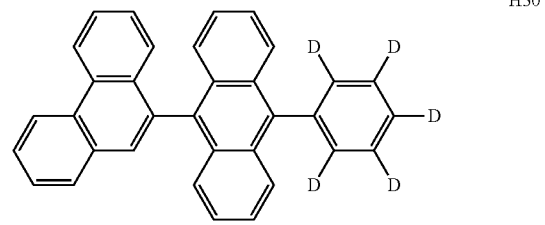
H31
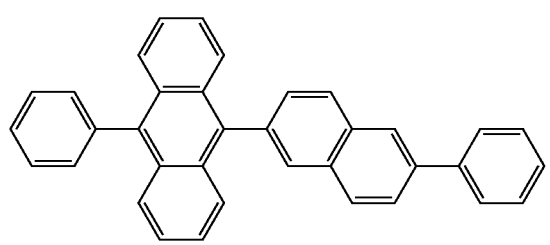
H32
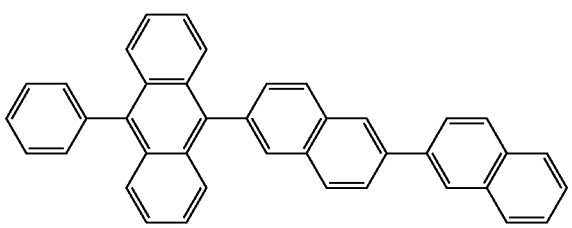
H33
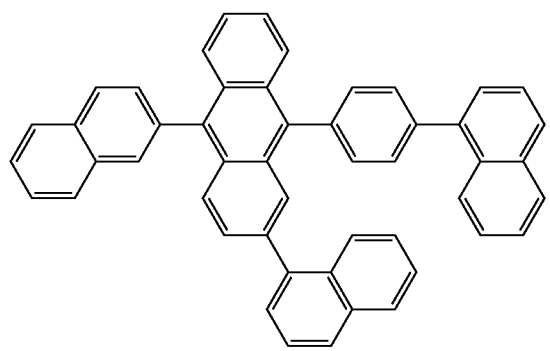
H34
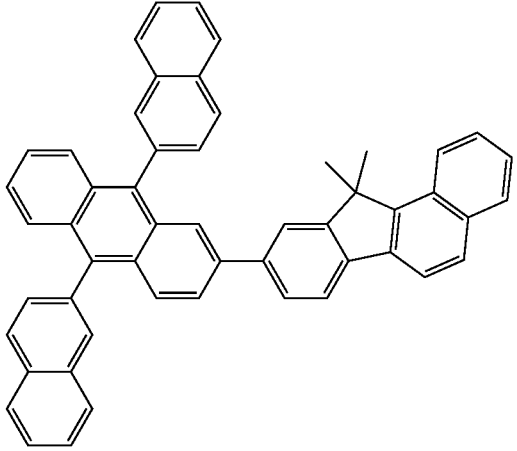
H35
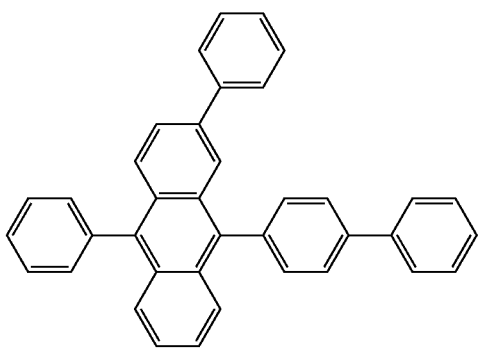

75
-continued
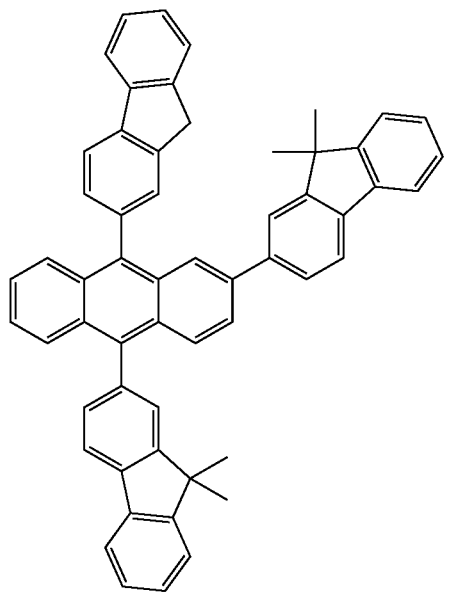
H37
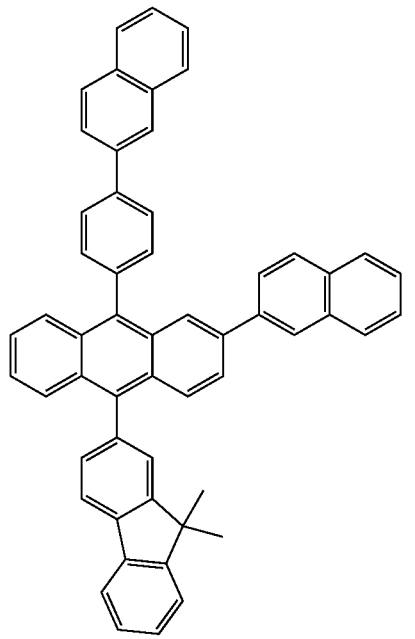
H38
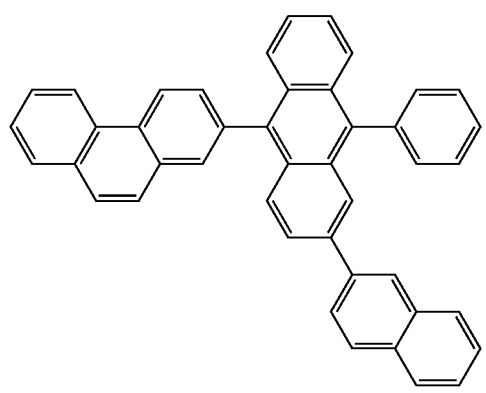
76
-continued
H36
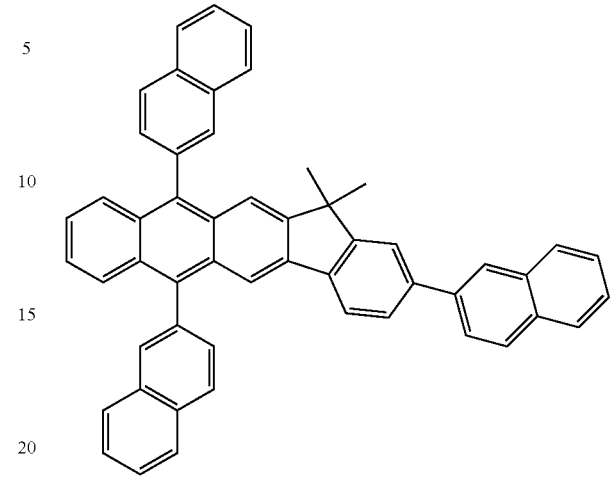
H39
H40
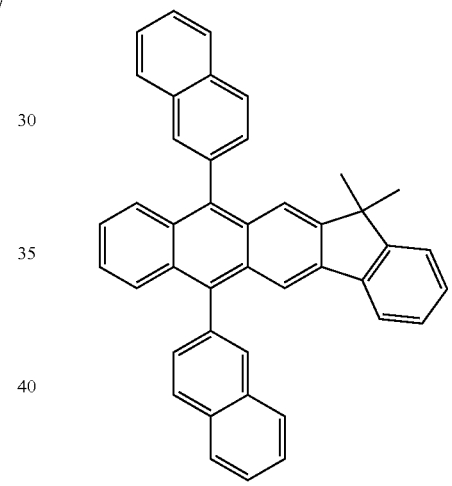
H41
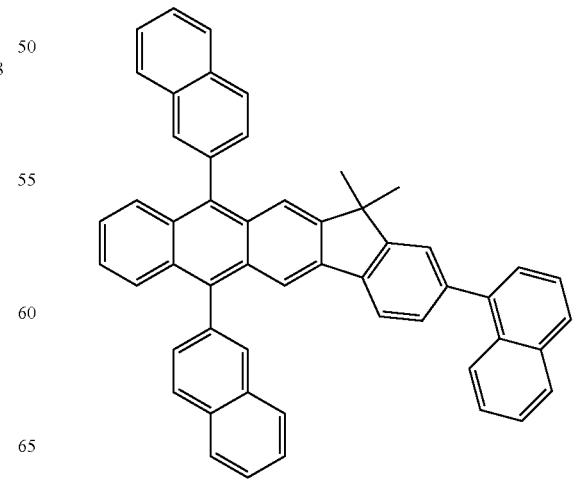

H42
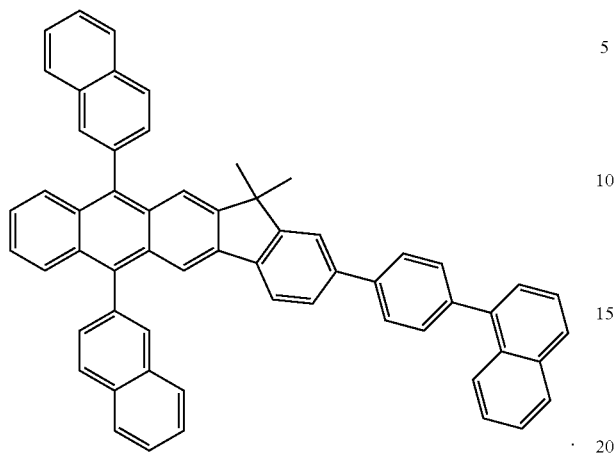
In various embodiments, the host may include one of Compounds H43 to H49 below, but is not limited thereto:
H43
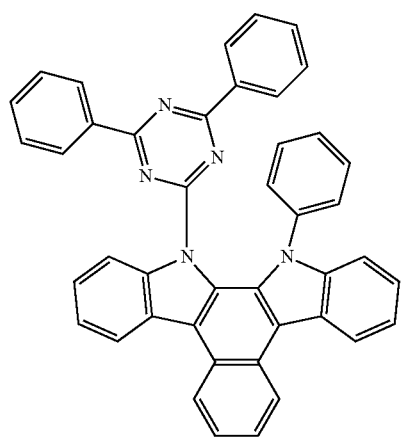
H44
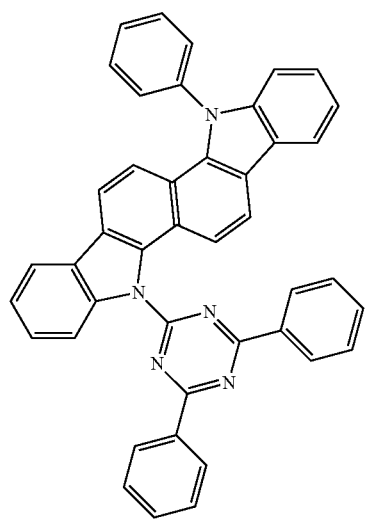
H45
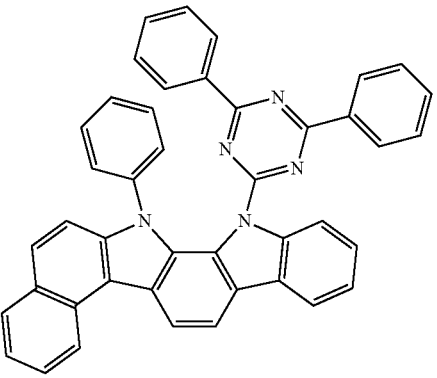
H46
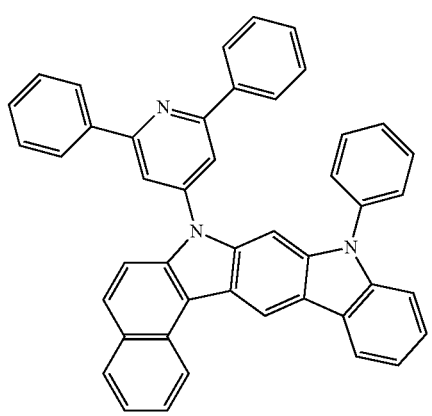
H47
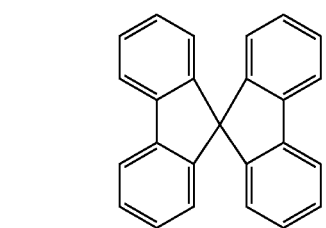
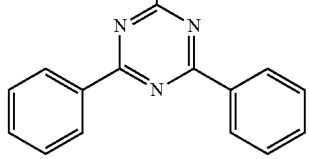
H48
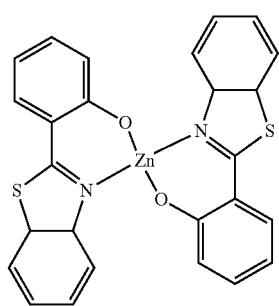

H49

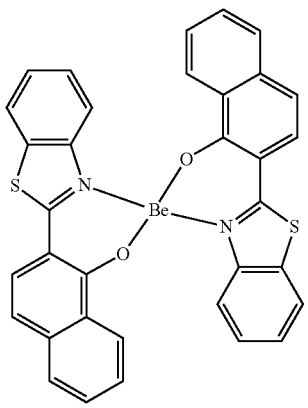

The dopant may be at least one selected from a suitable fluorescent dopant and a suitable phosphorescent dopant.

The phosphorescent dopant may include an organometallic complex represented by Formula 401 below:

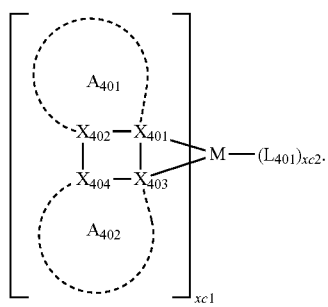

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be nitrogen or carbon;

$A_{401}$ and $A_{402}$ rings may each independently be selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene; and at least one substituent of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{401})(Q_{402})$, —$Si(Q_{403})(Q_{404})(Q_{405})$, and —$B(Q_{406})(Q_{407})$, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_1$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$) and —B($Q_{416}$)($Q_{417}$), and —N($Q_{411}$)($Q_{422}$), —Si($Q_{423}$)($Q_{424}$)($Q_{425}$), and —B($Q_{426}$)($Q_{427}$), wherein $Q_{401}$ to $Q_{407}$, $Q_{411}$ to $Q_{417}$ and $Q_{421}$ to $Q_{427}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group;

$L_{401}$ may be an organic ligand;

xc1 may be 1, 2, or 3; and xc2 may be 0, 1, 2, or 3.

For example, in Formula 401, $L_{401}$ may be a monovalent, divalent, or trivalent organic ligand. For example, $L_{401}$ may be selected from a halogen ligand (e.g., Cl and/or F), a diketone ligand (e.g., acetylacetonate, 1,3-diphenyl-1,3-propanedionate, 2,2,6,6-tetramethyl-3,5-heptanedionate, and/or hexafluoroacetonate), a carboxylic acid ligand (e.g., picolinate, dimethyl-3-pyrazolecarboxylate, and/or benzoate), a carbon monooxide ligand, an isonitrile ligand, a cyano ligand, and a phosphorous ligand (e.g., phosphine and/or phosphite), but is not limited thereto.

When $A_{401}$ in Formula 401 has two or more substituents, the two or more substituents of $A_{401}$ may be linked to form a saturated or unsaturated ring.

When $A_{402}$ in Formula 401 has two or more substituents, the two or more substituents of $A_{402}$ may be linked to form a saturated or unsaturated ring.

When xc1 in Formula 401 is two or more, a plurality of ligands

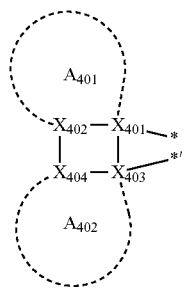

in Formula 401 may be identical to or different from each other. When xc1 in Formula 401 is two or more, $A_{401}$ and $A_{402}$ of one ligand may each independently be respectively connected to $A_{401}$ and $A_{402}$ of other neighboring ligands, either directly (e.g., via a bond such as a single bond) or with a linker (e.g., a $C_1$-$C_5$ alkylene group, —N(R')— (wherein R' may be a $C_1$-$C_{10}$ alkyl group or a $C_6$-$C_{20}$ aryl group), and/or —C(=O)—) therebetween.

The phosphorescent dopant may include one of Compounds PD1 to PD74 below, but is not limited thereto:

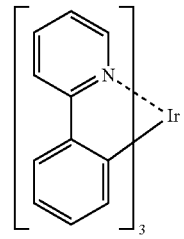

PD1

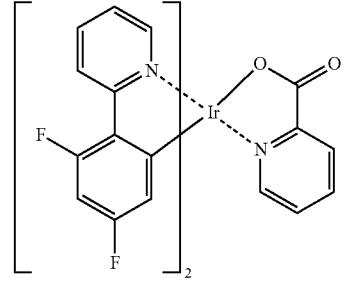

PD2

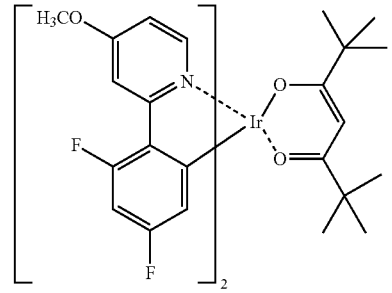

PD3

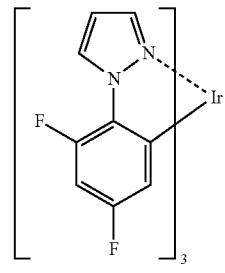

PD4

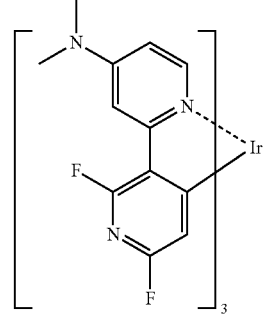

PD5

PD6 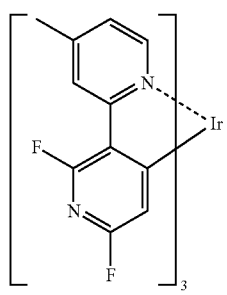
PD7 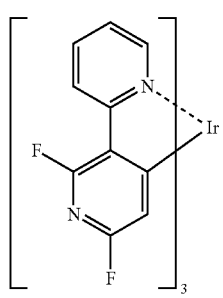
PD8 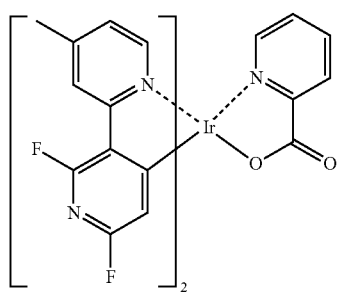
PD9 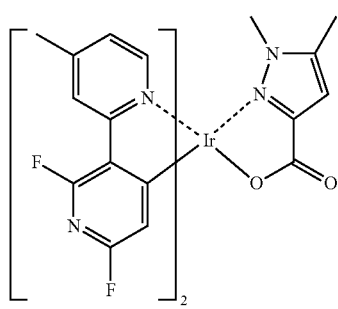
PD10 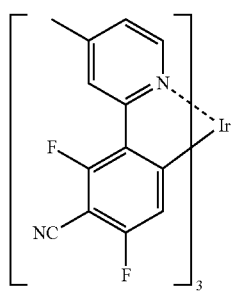
PD11 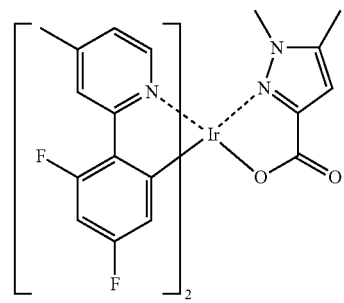
PD12 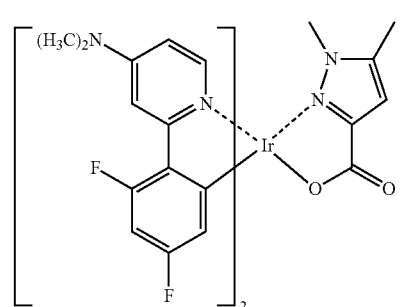
PD13 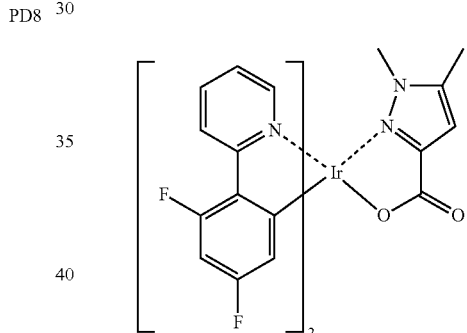
PD14 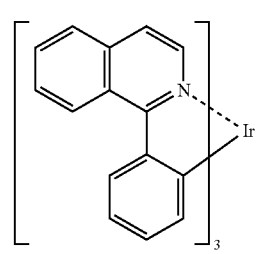
PD15 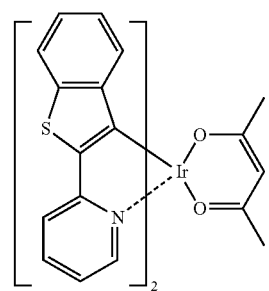

PD16 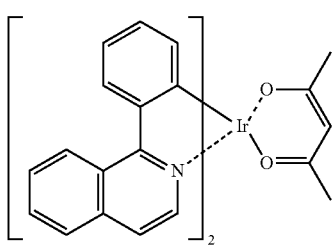
PD17 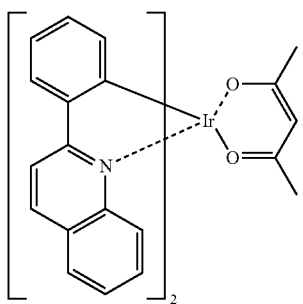
PD18 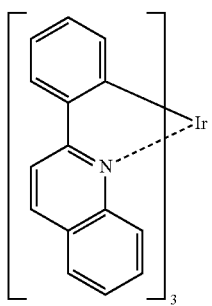
PD19 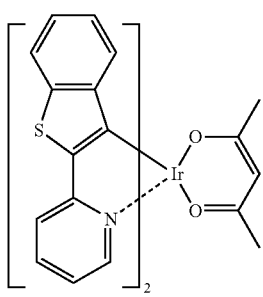
PD20 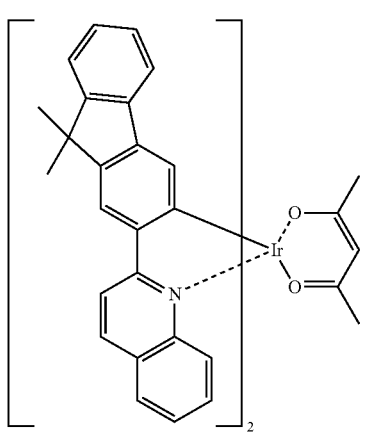
PD21 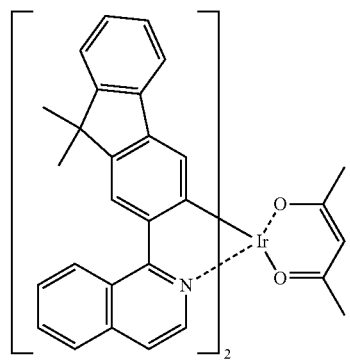
PD22 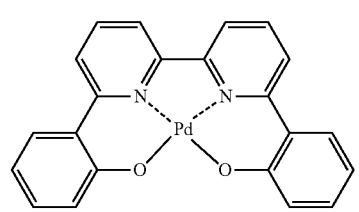
PD23 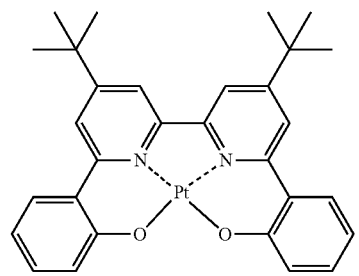
PD24 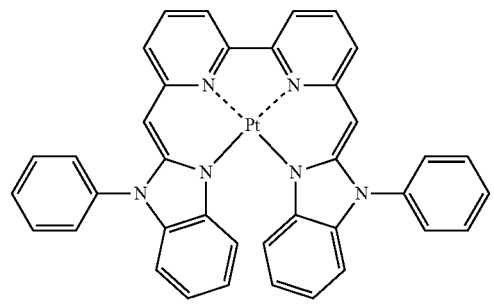
PD25 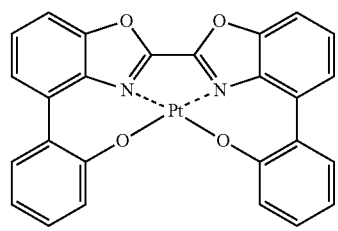
PD26 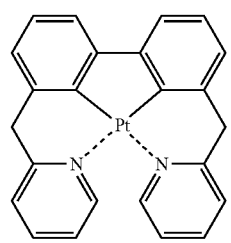

-continued
PD27 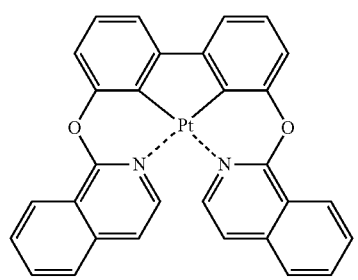
PD28 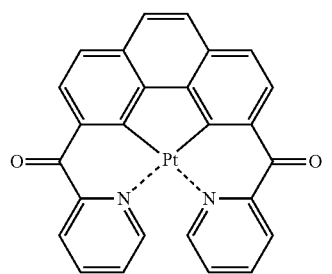
PD29 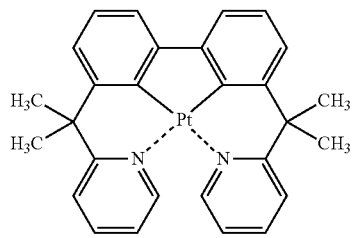
PD30 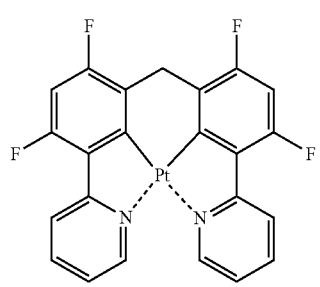
PD31 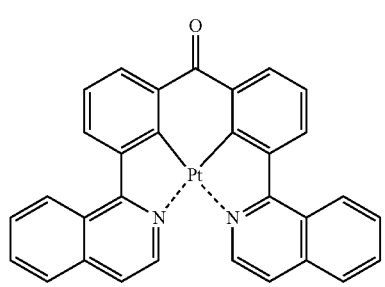
PD32 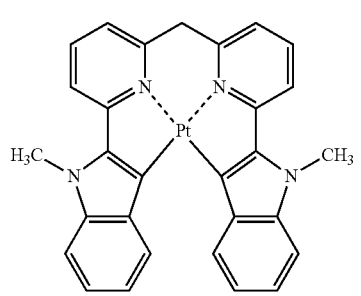
-continued
PD33 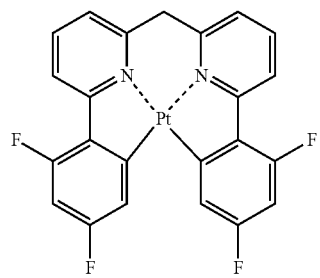
PD34 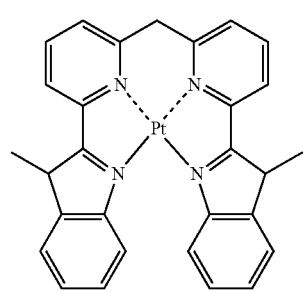
PD35 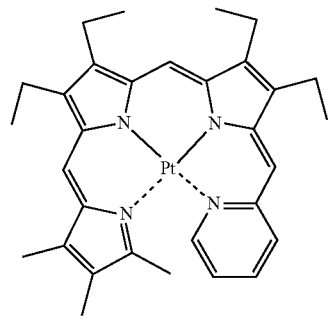
PD36 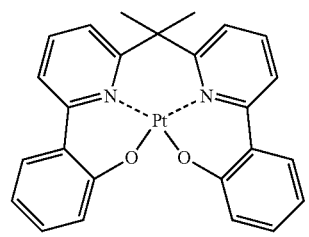
PD37 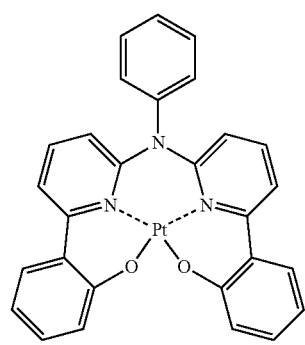

PD38
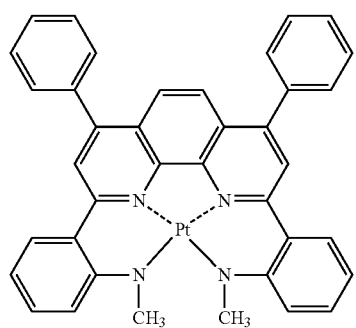
PD39
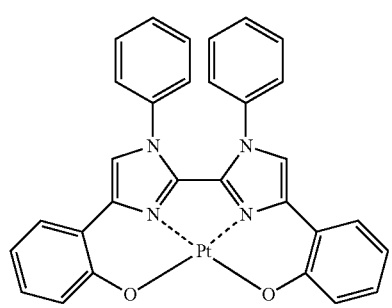
PD40
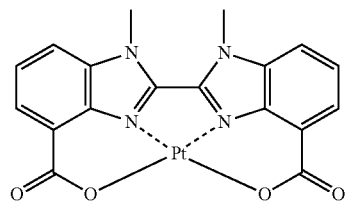
PD41
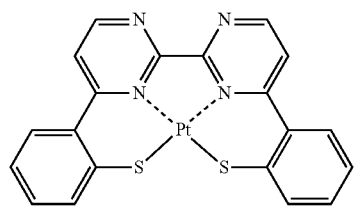
PD42
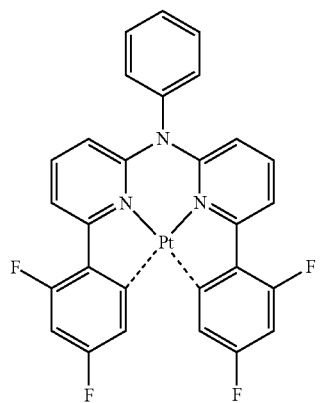
PD43
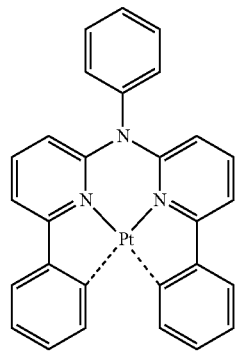
PD44
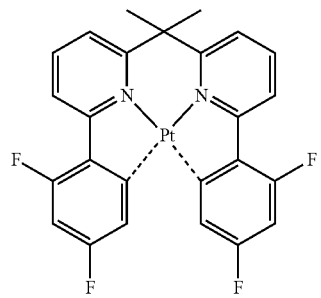
PD45
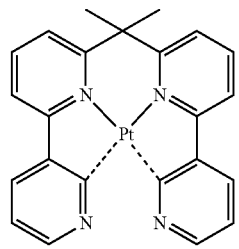
PD46
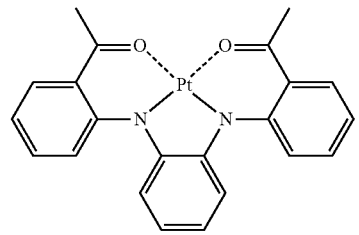
PD47
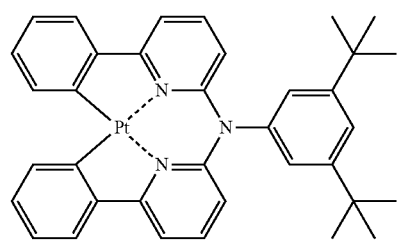
PD48
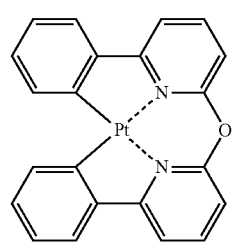

PD49 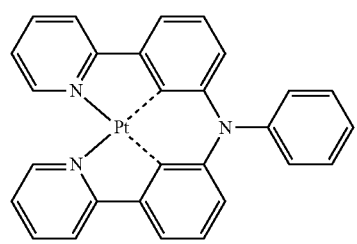
PD50 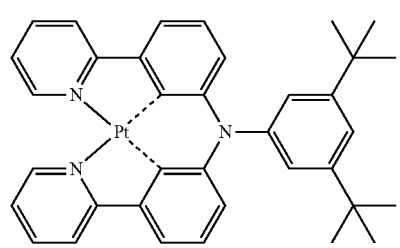
PD51 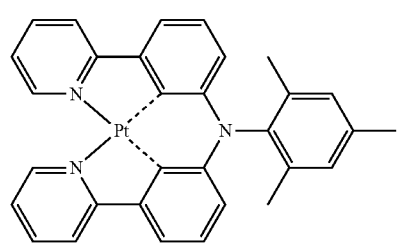
PD52 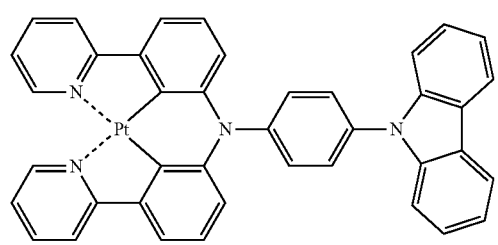
PD53 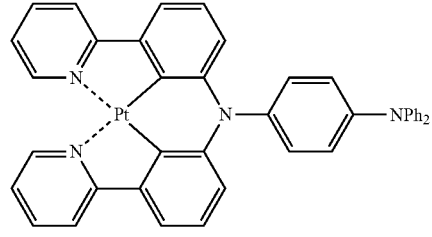
PD54 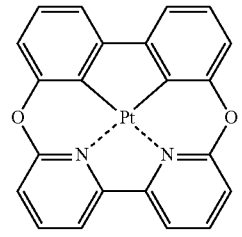
PD55 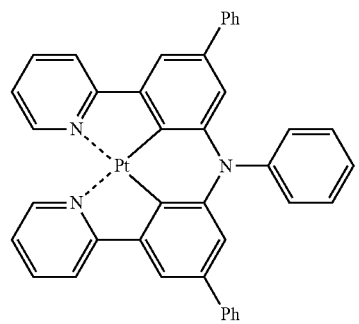
PD56 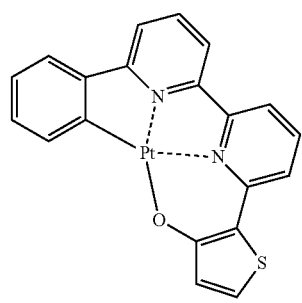
PD57 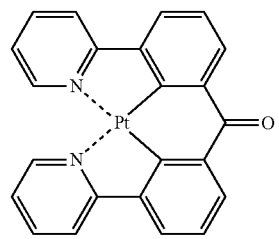
PD58 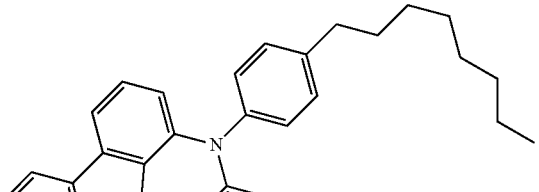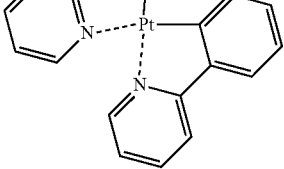
PD59 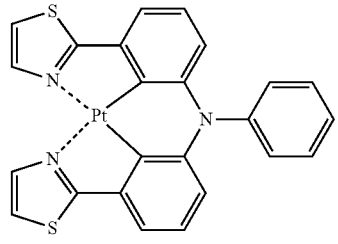

-continued
PD60
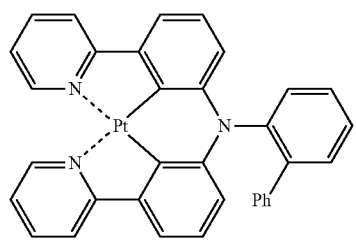
PD61
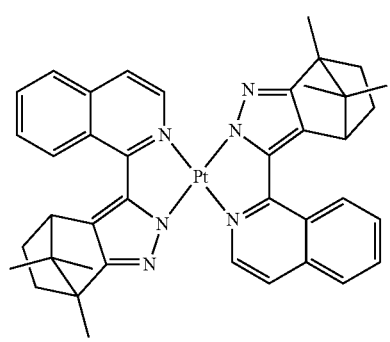
PD62
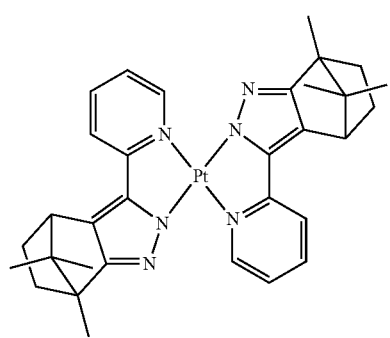
PD63
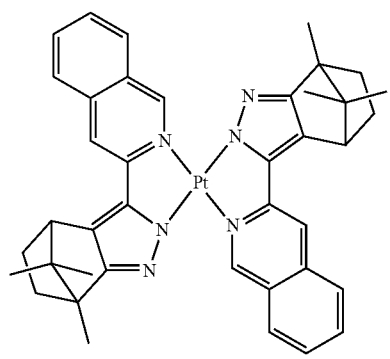
PD64
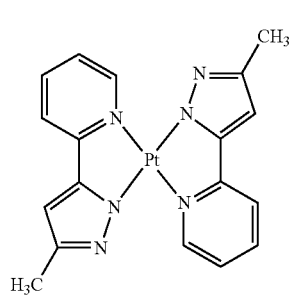
-continued
PD65
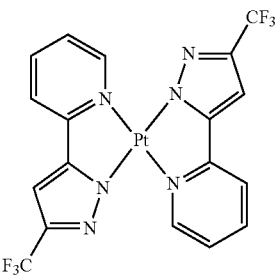
PD66
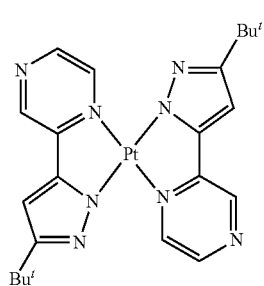
PD67
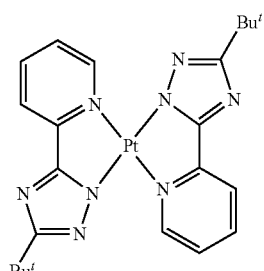
PD68
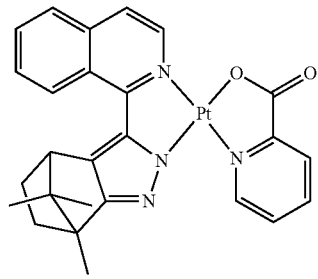
PD69
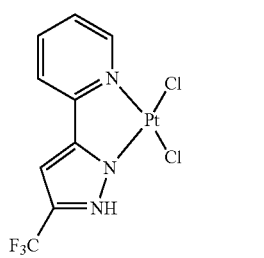

-continued
PD70
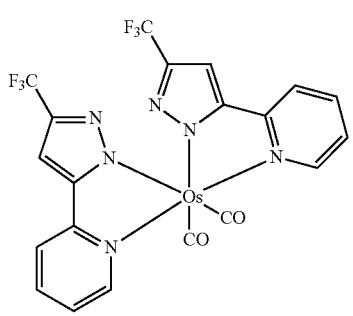
PD71
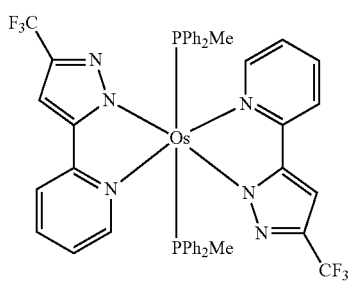
PD72
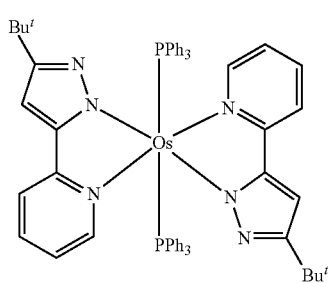
PD73
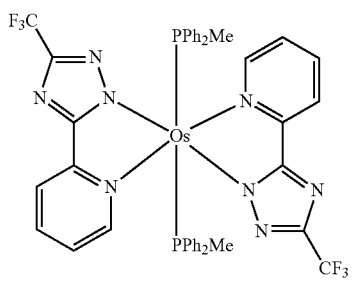
-continued
PD74
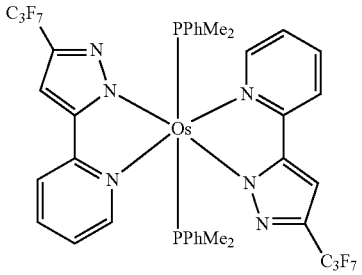
In various embodiments, the phosphorescent dopant may include PtOEP:
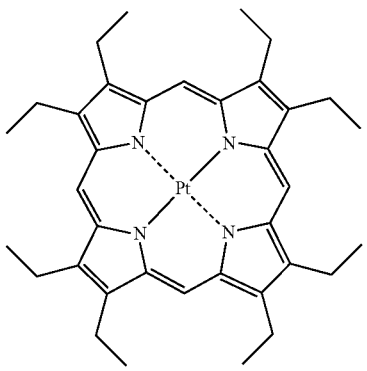
PtOEP
In some embodiments, the fluorescent dopant may include one selected from DPVBi, DPAVBi, TBPe, DCM, DCJTB, Coumarin 6, and C545T.
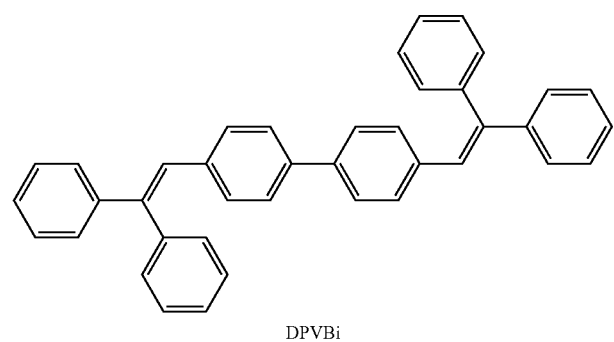
DPVBi -continued

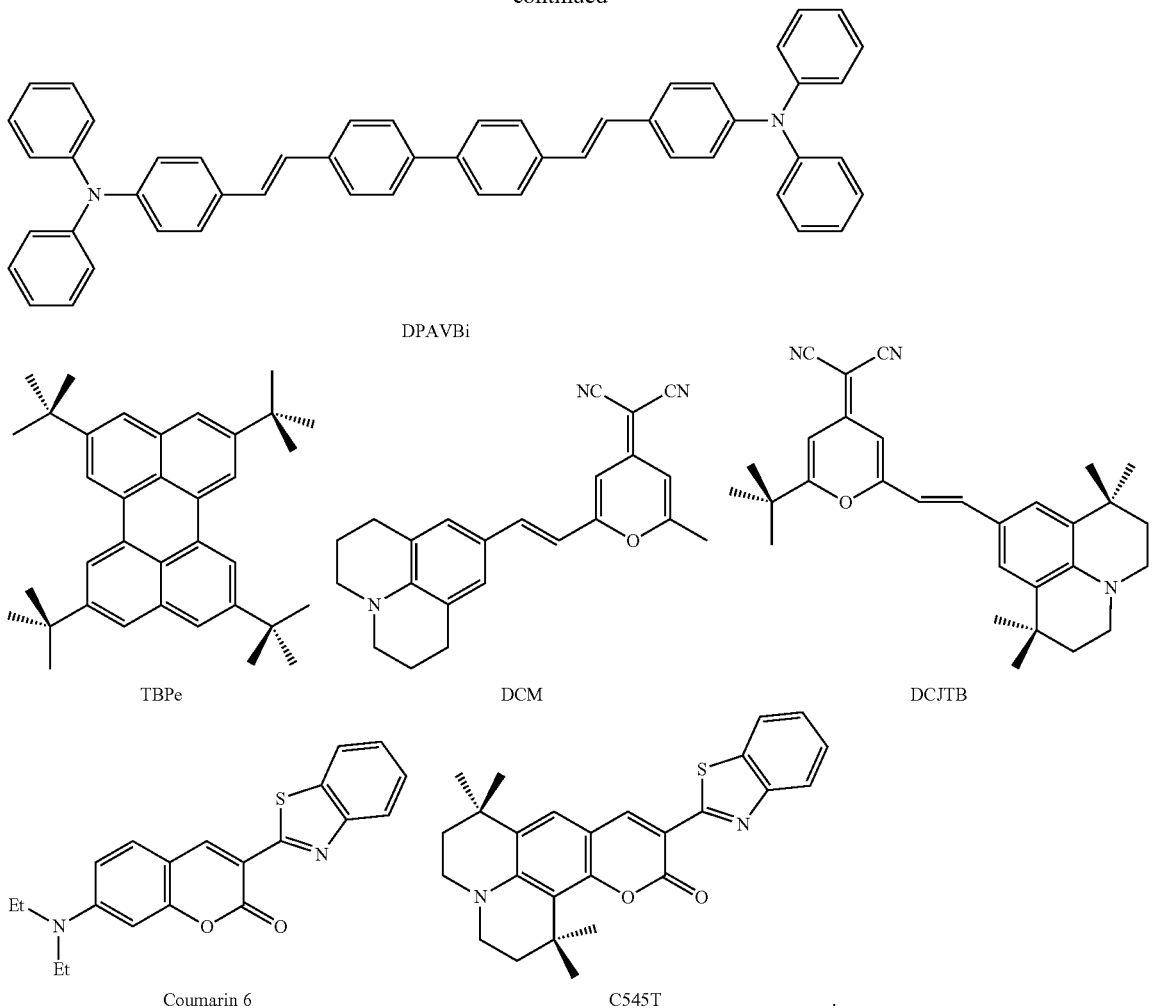

DPAVBi

TBPe

DCM

DCJTB

Coumarin 6

C545T

In various embodiments, the fluorescent dopant may include a compound represented by Formula 501 below:

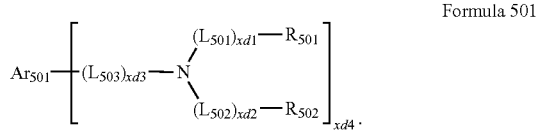

Formula 501

In Formula 501, $Ar_{501}$ may be selected from the group consisting of:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (where $Q_{501}$ to $Q_{503}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group).

Descriptions of $L_{501}$ to $L_{503}$ may be the same as the description provided herein in connection with $L_{301}$;

$R_{501}$ and $R_{502}$ may each independently be selected from the group consisting of:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 may each independently be selected from 0, 1, 2, and 3; and xd4 may be selected from 1, 2, 3, and 4.

The fluorescent dopant may include one of Compounds FD1 to FD8:

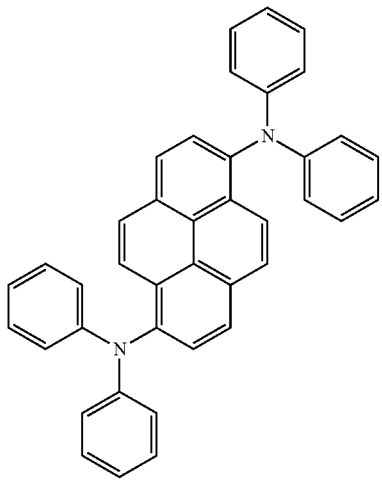

FD1

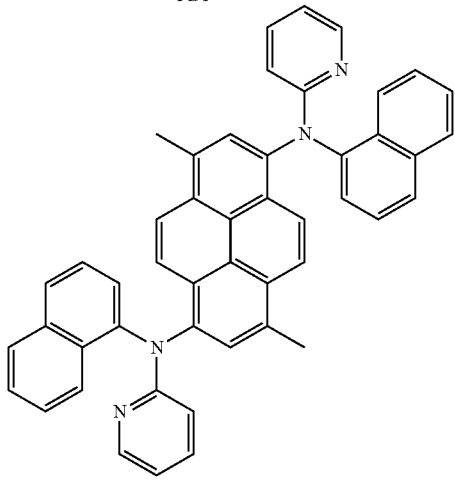

FD2

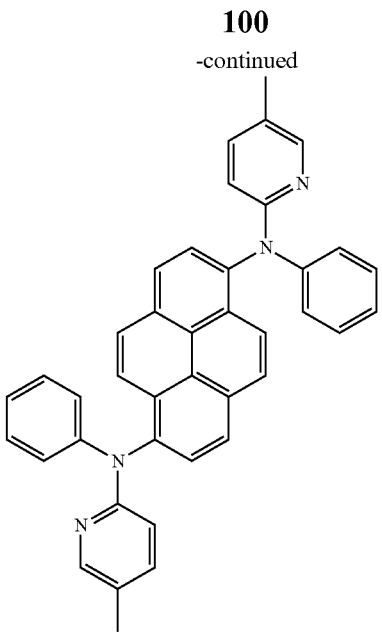

FD3

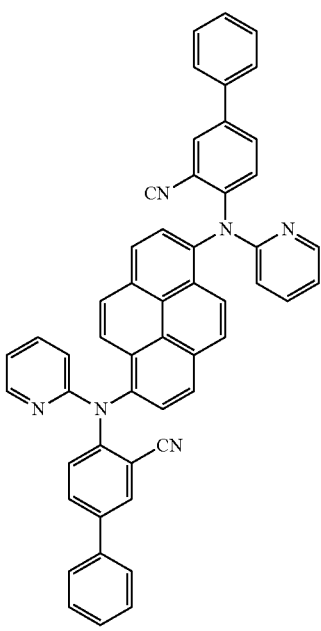

FD4

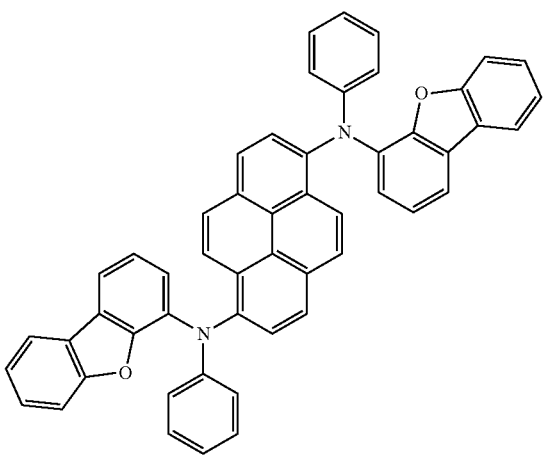

FD5

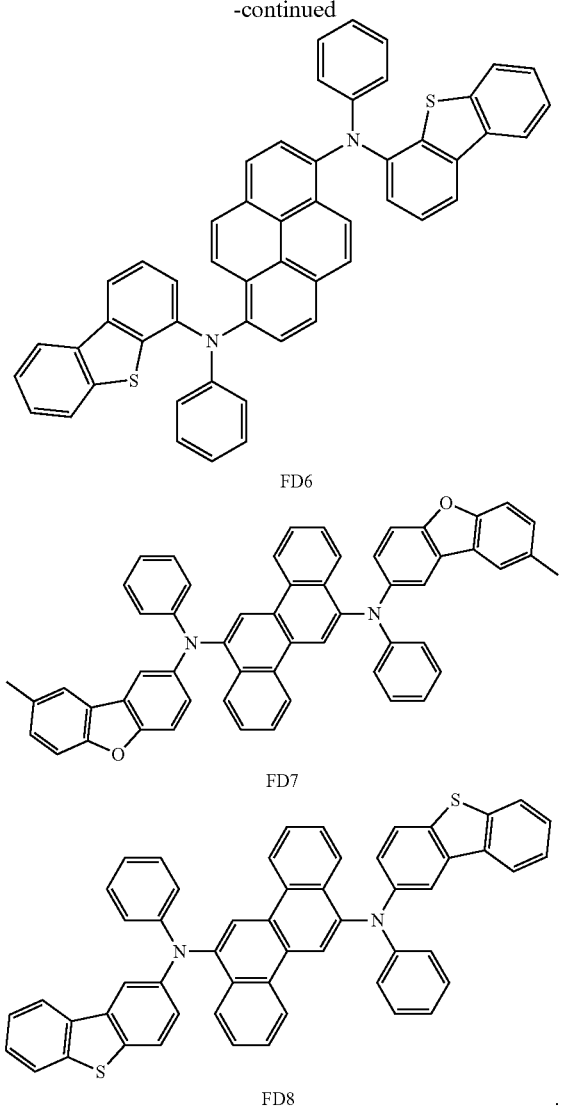

FD6

FD7

FD8

An amount of the dopant in the emission layer may be, for example, in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within any of these ranges, excellent (or suitable) light-emission characteristics may be obtained without a substantial increase in driving voltage.

An electron transport region may be disposed (e.g., positioned) on the emission layer.

The electron transport region may include at least one selected from a hole blocking layer, an electron transport layer (ETL), and an electron injection layer, but is not limited thereto.

When the electron transport region includes a hole blocking layer, the hole blocking layer may be formed on the emission layer by using one or more suitable methods such as vacuum deposition, spin coating, casting, a Langmuir-Blodgett (LB) method, ink-jet printing, laser-printing, and/or laser-induced thermal imaging. When the hole blocking layer is formed by vacuum deposition and/or spin coating, deposition and coating conditions for the hole blocking layer may be determined by referring to the deposition and coating conditions for the hole injection layer.

The hole blocking layer may include, for example, at least one selected from BCP and Bphen, but is not limited thereto.

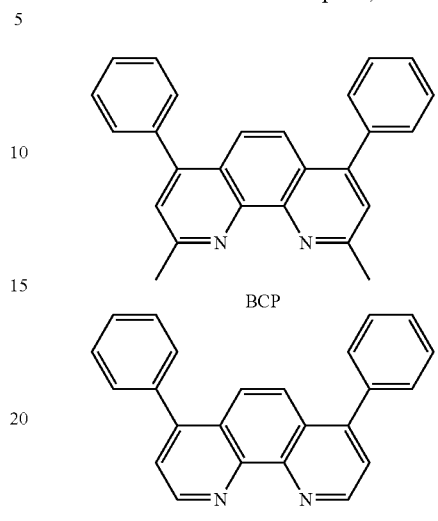

BCP

Bphen

A thickness of the hole blocking layer may be in a range of about 20 Å to about 1,000 Å, for example, about 30 Å to about 300 Å. When the thickness of the hole blocking layer is within any of these ranges, the hole blocking layer may have excellent (or suitable) hole blocking characteristics without a substantial increase in driving voltage.

For example, the electron transport region may have a structure of electron transport layer/electron injection layer or a structure of hole blocking layer/electron transport layer/electron injection layer, wherein the layers of each structure are sequentially stacked from the emission layer in the stated order, but the structure of the electron transport region is not limited thereto.

According to an embodiment of the present disclosure, the organic layer 150 of the organic light-emitting device includes an electron transport region disposed between the emission layer and the second electrode 190, and the electron transport region may include an electron transport layer. The electron transport layer may include a plurality of layers. For example, the electron transport layer may include a first electron transport layer and a second electron transport layer.

The electron transport layer may further include at least one selected from BCP, Bphen, Alq$_3$, Balq, TAZ, and NTAZ.

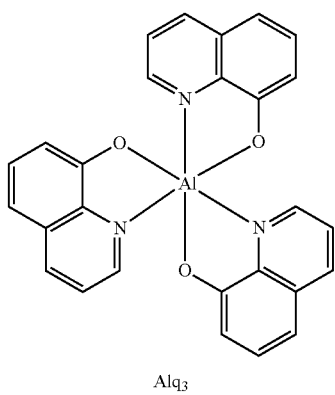

Alq$_3$

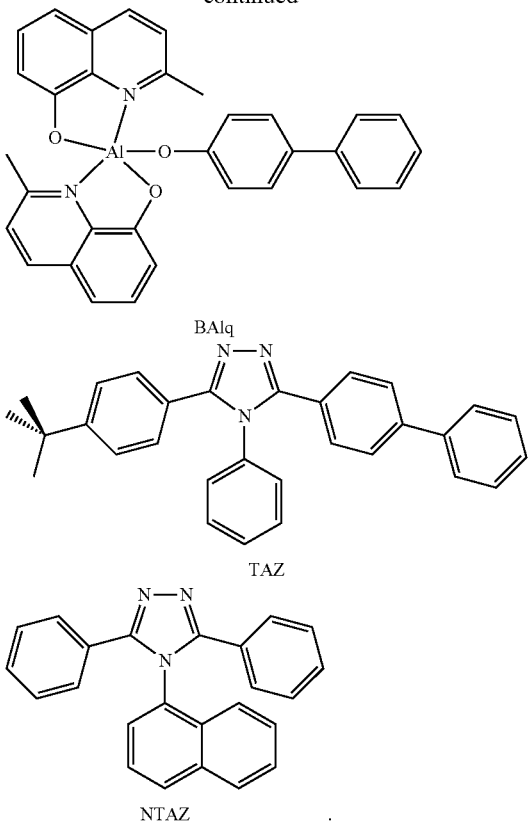

BAlq

TAZ

NTAZ

In various embodiments, the electron transport layer may include at least one compound selected from a compound represented by Formula 601 and a compound represented by Formula 602 illustrated below:

$$Ar_{601}\text{-}[(L_{601})_{xe1}\text{-}E_{601}]_{xe2}.$$  Formula 601

In Formula 601, $Ar_{601}$ may be selected from the group consisting of:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, monovalent non-aromatic condensed heteropolycyclic group, and —Si($Q_{301}$)($Q_{302}$)($Q_{303}$) (where $Q_{301}$ to $Q_{303}$ may each independently be selected from hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

a description of $L_{601}$ may be understood by referring to the description provided in connection with $L_{301}$;

$E_{601}$ may be selected from the group consisting of:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and xe2 may be selected from 1, 2, 3, and 4.

Formula 602

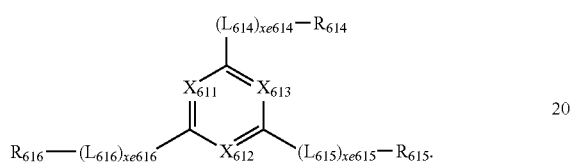

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, and at least one selected from $X_{611}$ to $X_{613}$ may be N;

descriptions of $L_{611}$ to $L_{616}$ may be each independently understood by referring to the description provided herein in connection with $L_{301}$;

$R_{611}$ to $R_{616}$ may each independently be selected from the group consisting of:

a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may each independently be selected from 0, 1, 2, and 3.

The compound represented by Formula 601 and the compound represented by Formula 602 may each independently be selected from Compounds ET1 to ET15 illustrated below.

ET1

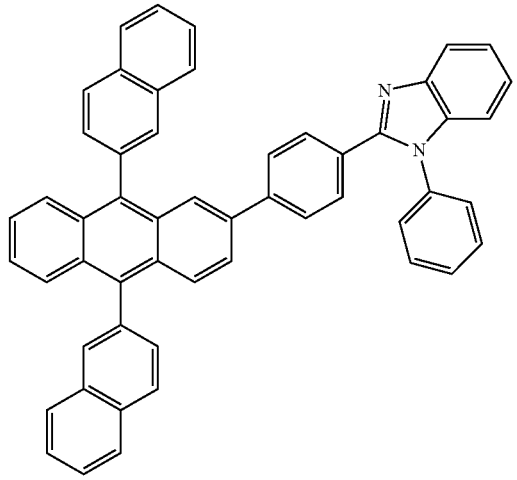

ET2

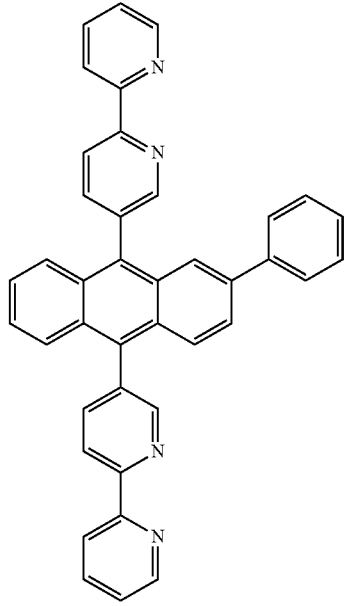

ET3

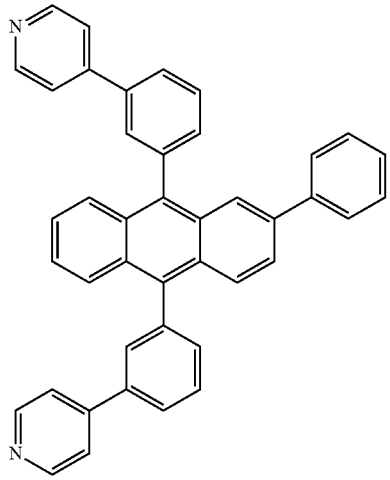

ET4
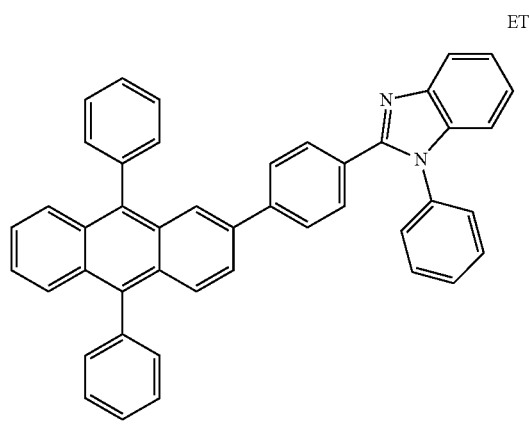
ET7
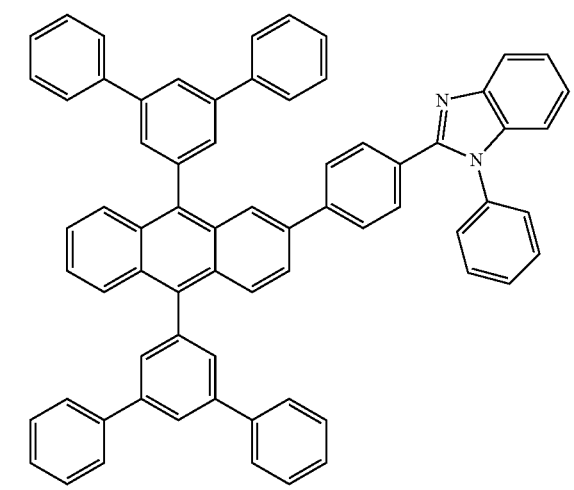
ET5
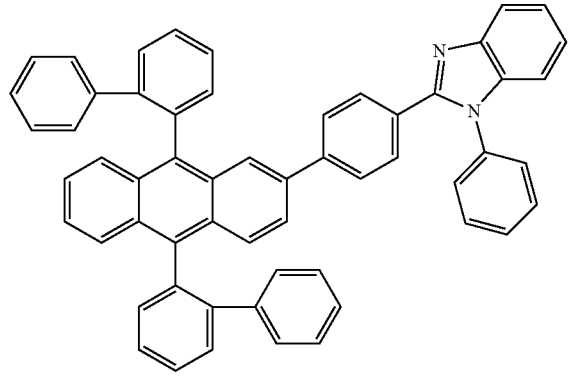
ET8
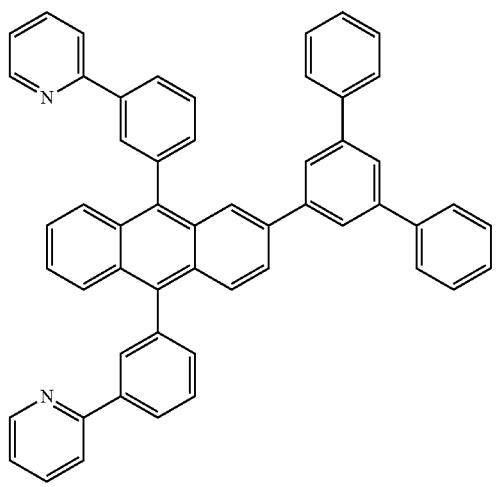
ET6
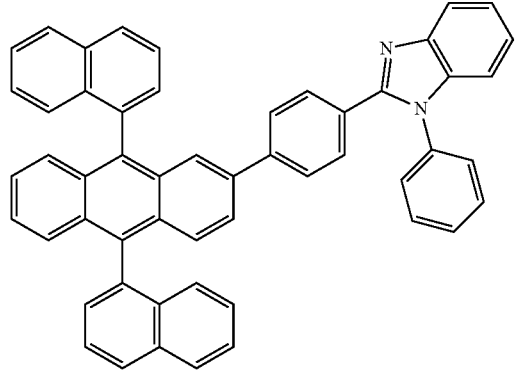
ET9
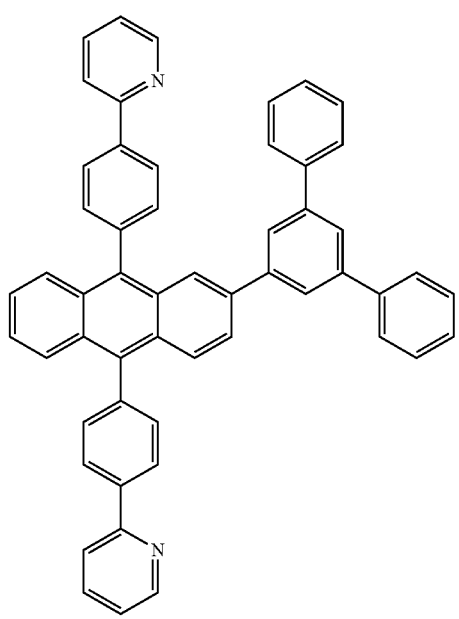

ET10

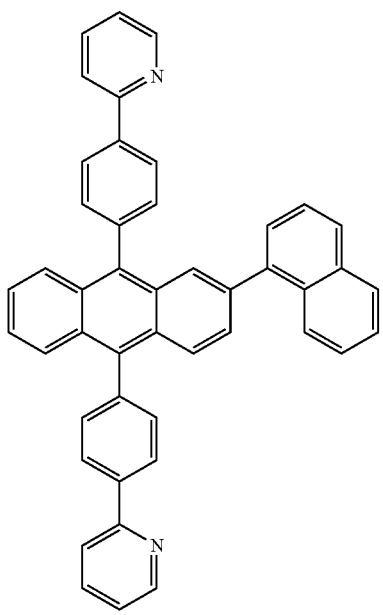

ET11

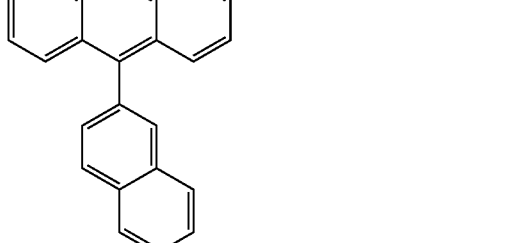

ET12

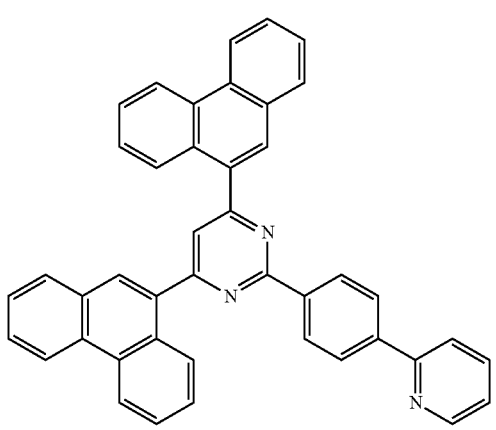

ET13

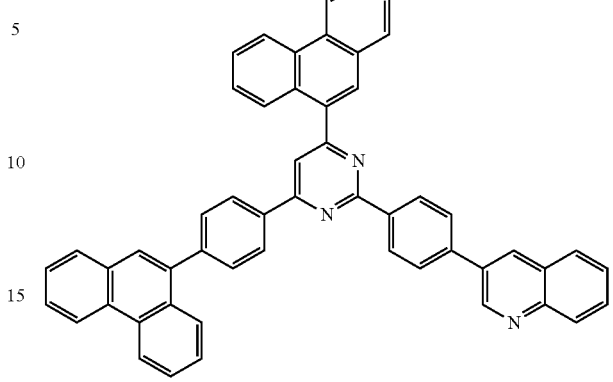

ET14

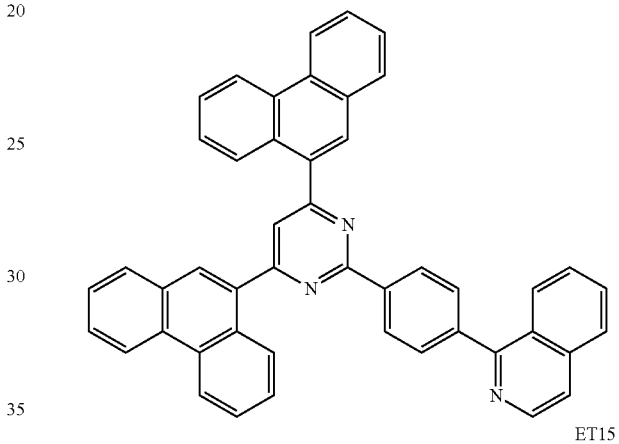

ET15

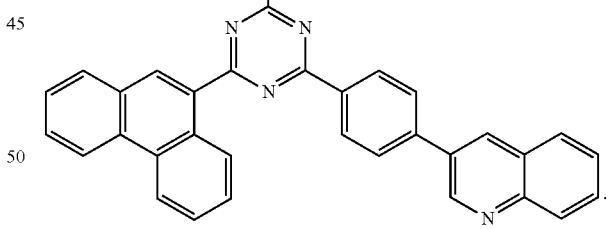

A thickness of the electron transport layer may be in a range of about 100 Å to about 1,000 Å, for example, about 150 Å to about 500 Å. When the thickness of the electron transport layer is within any of the ranges described above, the electron transport layer may have satisfactory (or suitable) electron transport characteristics without a substantial increase in driving voltage.

In some embodiments, the electron transport layer may further include, in addition to the materials described above, a metal-containing material.

The metal-containing material may include a Li complex. The Li complex may include, for example, Compound ET-D1 (lithium quinolate, LiQ) and/or Compound ET-D2.

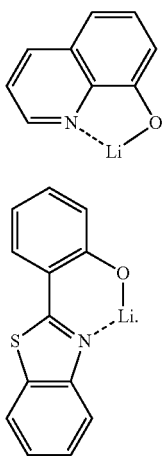

ET-D1

ET-D2

The electron transport region may include an electron injection layer that may function to facilitate the injection of electrons from the second electrode 190.

The electron injection layer may be formed on the electron transport layer by using one or more suitable methods such as vacuum deposition, spin coating, casting, a LB method, ink-jet printing, laser-printing, and/or laser-induced thermal imaging. When an electron injection layer is formed by vacuum deposition and/or spin coating, deposition and coating conditions for the electron injection layer may be the same as (or substantially similar to) those for the hole injection layer.

The electron injection layer may include at least one selected from LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within any of the ranges described above, the electron injection layer may have satisfactory (or suitable) electron injection characteristics without a substantial increase in driving voltage.

The second electrode 190 may be disposed on the organic layer 150 having the structure according to embodiments of the present disclosure. The second electrode 190 may be a cathode, which is an electron injection electrode, and in this regard, a material for forming the second electrode 190 may be selected from a metal, an alloy, an electrically conductive compound, and a mixture thereof, which have a relatively low work function. Non-limiting examples of the material for forming the second electrode 190 include lithium (Li), magnesium (Mg), aluminum (Al), aluminum-lithium (Al—Li), calcium (Ca), magnesium-indium (Mg—In), and magnesium-silver (Mg—Ag). In various embodiments, the material for forming the second electrode 190 may be ITO and/or IZO. The second electrode 190 may be a reflective electrode, a semi-transmissive electrode, or a transmissive electrode.

An organic layer according to an embodiment may be formed by depositing the compound according to an embodiment of the present disclosure, or may be formed by using a wet method in which the compound according to an embodiment of the present disclosure is prepared in the form of solution and then the solution of the compound is used for coating.

An organic light-emitting device according to an embodiment may be used in various display apparatuses, such as a passive matrix organic light-emitting display apparatus and/or an active matrix organic light-emitting display apparatus. For example, when the organic light-emitting device is included in an active matrix organic light-emitting display apparatus, a first electrode disposed on a substrate may function as a pixel electrode and may be electrically connected (e.g., coupled) to a source electrode or a drain electrode of a thin film transistor. In addition, the organic light-emitting device may be included in a display apparatus that emits light in opposite directions (e.g., that can emit light from both sides of the display panel).

Hereinbefore, the organic light-emitting device has been described with reference to the drawing, but embodiments of the present disclosure are not limited thereto.

Hereinafter, definitions of substituents of compounds used herein will be presented. However, the number of carbon atoms used to restrict a substituent is not limited, and does not limit properties of the substituent. Unless defined otherwise, the definition of the substituent is consistent with a general definition thereof.

A $C_1$-$C_{60}$ alkyl group used herein may refer to a linear or branched aliphatic hydrocarbon monovalent group having 1 to 60 carbon atoms, and non-limiting examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group used herein may refer to a divalent group having the same structure as the $C_1$-$C_{60}$ alkyl group.

A $C_1$-$C_{60}$ alkoxy group used herein may refer to a monovalent group represented by —$OA_{101}$ (wherein $A_{101}$ is the $C_1$-$C_{60}$ alkyl group), and non-limiting examples thereof are a methoxy group, an ethoxy group, and an isopropoxy group.

A $C_2$-$C_{60}$ alkenyl group used herein may refer to a hydrocarbon group having at least one carbon double bond at one or more positions along the hydrocarbon chain of the $C_2$-$C_{60}$ alkyl group (e.g., in the middle or at either terminal end of the $C_2$-$C_{60}$ alkyl group), and non-limiting examples thereof are an ethenyl group, a propenyl group, and a butenyl group. A $C_2$-$C_{60}$ alkenylene group used herein may refer to a divalent group having the same structure as the $C_2$-$C_{60}$ alkenyl group.

A $C_2$-$C_{60}$ alkynyl group used herein may refer to a hydrocarbon group having at least one carbon triple bond at one or more positions along the hydrocarbon chain of the $C_2$-$C_{60}$ alkyl group (e.g., in the middle or at either terminal end of the $C_2$-$C_{60}$ alkyl group), and non-limiting examples thereof are an ethynyl group and a propynyl group. A $C_2$-$C_{60}$ alkynylene group used herein may refer to a divalent group having the same structure as the $C_2$-$C_{60}$ alkynyl group.

A $C_3$-$C_{10}$ cycloalkyl group used herein may refer to a monovalent hydrocarbon monocyclic group having 3 to 10 carbon atoms, and non-limiting examples thereof are a cyclopropyl group, a cyclobutyl group, a cyclopentyl group, a cyclohexyl group, and a cycloheptyl group. A $C_3$-$C_{10}$ cycloalkylene group used herein may refer to a divalent group having the same structure as the $C_3$-$C_{10}$ cycloalkyl group.

A $C_2$-$C_{10}$ heterocycloalkyl group used herein may refer to a monovalent monocyclic group having at least one heteroatom selected from N, O, P, and S as a ring-forming atom and 2 to 10 carbon atoms, and non-limiting examples thereof are a tetrahydrofuranyl group, and a tetrahydrothiophenyl group. A $C_2$-$C_{10}$ heterocycloalkylene group used herein may refer to a divalent group having the same structure as the $C_2$-$C_{10}$ heterocycloalkyl group.

A $C_3$-$C_{10}$ cycloalkenyl group used herein may refer to a monovalent monocyclic group that has 3 to 10 carbon atoms and at least one double bond in the ring thereof, and does not have aromaticity, and non-limiting examples thereof are a cyclopentenyl group, a cyclohexenyl group, and a cycloheptenyl group. A $C_3$-$C_{10}$ cycloalkenylene group used herein may refer to a divalent group having the same structure as the $C_3$-$C_{10}$ cycloalkenyl group.

A $C_2$-$C_{10}$ heterocycloalkenyl group used herein may refer to a monovalent monocyclic group that has at least one heteroatom selected from N, O, P, and S as a ring-forming atom, 2 to 10 carbon atoms, and at least one double bond in its ring. Non-limiting examples of the $C_2$-$C_{10}$ heterocycloalkenyl group are a 2,3-hydrofuranyl group and a 2,3-hydrothiophenyl group. A $C_2$-$C_{10}$ heterocycloalkenylene group used herein may refer to a divalent group having the same structure as the $C_2$-$C_{10}$ heterocycloalkenyl group.

A $C_6$-$C_{60}$ aryl group used herein may refer to a monovalent group having a carbocyclic aromatic system having 6 to 60 carbon atoms, and a $C_6$-$C_{60}$ arylene group used herein may refer to a divalent group having a carbocyclic aromatic system having 6 to 60 carbon atoms. Non-limiting examples of the $C_6$-$C_{60}$ aryl group are a phenyl group, a biphenyl group, a terphenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each independently include two or more rings, the respective rings may be fused to each other.

A $C_1$-$C_{60}$ heteroaryl group used herein may refer to a monovalent group having a carbocyclic aromatic system that has at least one heteroatom selected from N, O, P, and S as a ring-forming atom, and 1 to 60 carbon atoms. A $C_1$-$C_{60}$ heteroarylene group used herein may refer to a divalent group having a carbocyclic aromatic system that has at least one heteroatom selected from N, O, P, and S as a ring-forming atom, and 1 to 60 carbon atoms. Non-limiting examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each independently include two or more rings, the respective rings may be fused to each other.

A $C_6$-$C_{60}$ aryloxy group used herein may refer to a monovalent group represented by $-OA_{102}$ (wherein $A_{102}$ is the $C_6$-$C_{60}$ aryl group), and a $C_6$-$C_{60}$ arylthio group may refer to a monovalent group represented by $-SA_{103}$ (wherein $A_{103}$ is the $C_6$-$C_{60}$ aryl group).

A monovalent non-aromatic condensed polycyclic group used herein may refer to a monovalent group that has two or more rings condensed (e.g., fused) to each other, only carbon atoms as ring forming atoms (e.g., 8 to 60 carbon atoms), and non-aromaticity in the entire molecular structure (e.g., not having overall aromaticity). A non-limiting example of the monovalent non-aromatic condensed polycyclic group is a fluorenyl group. A divalent non-aromatic condensed polycyclic group used herein may refer to a divalent group having the same structure as the monovalent non-aromatic condensed polycyclic group.

A monovalent non-aromatic condensed heteropolycyclic group used herein may refer to a monovalent group that has two or more rings condensed (e.g., fused) to each other, has at least one heteroatom selected from N, O, P, and S, other than carbon atoms (e.g., 2 to 60 carbon atoms), as ring forming atoms, and has non-aromaticity in the entire molecular structure (e.g., does not have overall aromaticity). A divalent non-aromatic condensed heteropolycyclic group used herein may refer to a divalent group having the same structure as the monovalent non-aromatic condensed heteropolycyclic group.

As used herein, at least one substitutent of the substituted $C_3$-$C_{10}$ cycloalkylene group, substituted $C_2$-$C_{10}$ heterocycloalkylene group, substituted $C_3$-$C_1$ cycloalkenylene group, substituted $C_2$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from the group consisting of:

deuterium, $-F$, $-Cl$, $-Br$, $-I$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, $-F$, $-Cl$, $-Br$, $-I$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-N(Q_{11})(Q_{12})$, $-Si(Q_{13})(Q_{14})(Q_{15})$, and $-B(Q_{16})(Q_{17})$, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, $-F$, $-Cl$, $-Br$, $-I$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), and —N($Q_{31}$)($Q_{32}$), —Si($Q_{33}$)($Q_{34}$)($Q_{35}$) and —B($Q_{36}$)($Q_{37}$), wherein $Q_{11}$ to $Q_{17}$, $Q_{21}$ to $Q_{27}$ and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_1$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from the group consisting of:

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$), a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{26}$), and —B($Q_{26}$)($Q_{27}$), and —N($Q_{31}$)($Q_{32}$), —Si($Q_{33}$)($Q_{34}$)($Q_{35}$) and —B($Q_{36}$)($Q_{37}$), wherein $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

The expression "Ph" used herein may refer to a phenyl group, the expression "Me" used herein may refer to a methyl group, the expression "Et" used herein may refer to an ethyl group, the expression "ter-Bu" or "Bu$^t$" used herein may refer to a tert-butyl group, and "D" may refer to deuterium.

Hereinafter, an organic light-emitting device according to one or more embodiments of the present disclosure will be described in more detail with reference to Synthesis Examples and Examples.

Synthesis Examples

Synthesis Example: Synthesis of Intermediate

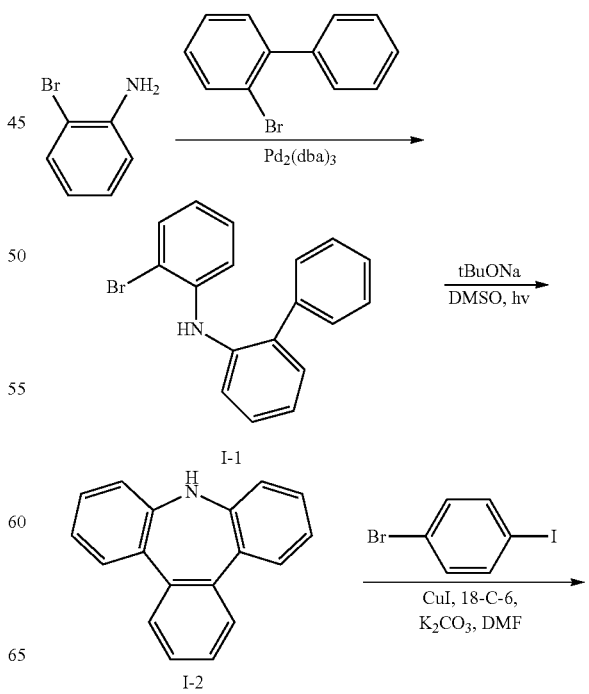

-continued

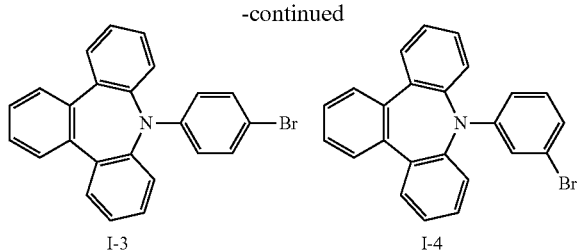

I-3    I-4

Synthesis of Intermediate I-1

3.44 g (20 mmol) of 2-bromoaniline, 7.0 g (30.0 mmol) of 2-bromobiphenyl, 0.92 g (1.0 mmol) of $Pd_2(dba)_3$, 0.2 g (1.0 mmol) of $P(tBu)_3$, and 2.88 g (30.0 mol) of NaOtBu were dissolved in 60 mL of toluene, and then the resulting mixture was stirred at a temperature of about 80° C. for 5 hours. The obtained reaction solution was allowed to come to ambient temperature. Then, an extraction process was performed thereon three times by using each of 40 mL of water and 40 mL of diethyl ether. The obtained organic layer was dried by using magnesium sulfate ($MgSO_4$). A solvent was next removed therefrom by evaporation. The obtained residue was separated and purified through silica gel column chromatography to obtain 5.12 g of Intermediate I-1 (yield: 79%). The obtained compound was identified by liquid chromatography-mass spectrometry (LC-MS).

$C_{18}H_{14}BrN$: M+1 324.0

Synthesis of Intermediate I-2

3.37 g (30.0 mmol) of tBuONa was added to 100 mL of dried dimethyl sulfoxide (DMSO), in which oxygen was removed. 5 minutes after the addition, 4.86 g (15.0 mmol) of Intermediate I-1 was added thereto, and then the resulting mixture was subject to a reaction with a 400 W lamp (350 nm) for about 60 minutes. Once the reaction was complete, the result was neutralized using water and a large amount of ammonium nitrate, and then an extraction process was performed thereon three times using 100 mL of dichloromethane. The obtained organic layer was dried by using $MgSO_4$. A solvent was next removed therefrom by evaporation. The obtained residue was separated and purified through silica gel column chromatography to obtain 1.82 g of Intermediate I-2 (yield: 50%). The obtained compound was identified by LC-MS.

$C_{18}H_{13}N$: M+1 244.1

Synthesis of Intermediate I-3

1.82 g (7.5 mmol) of Intermediate I-2, 2.54 g (9.0 mmol) of 1-bromo-4-iodobenzene, 0.13 g (0.7 mmol) of CuI, 0.17 g (0.7 mmol) of 18-Crown-6, and 2.90 g (21.0 mmol) of $K_2CO_2$ were dissolved in 30 mL of dimethylformamide (DMF), and then the resulting mixture was stirred at a temperature of about 140° C. for about 12 hours. The obtained reaction solution was allowed to come to ambient temperature. Then, an extraction process was performed thereon three times by using each of 30 mL of water and 30 mL of ethyl ether. The obtained organic layer was dried by using $MgSO_4$. A solvent was next removed therefrom by evaporation. The obtained residue was separated and purified through silica gel column chromatography to obtain 2.69 g of Intermediate I-3 (yield: 90%). The obtained compound was identified by LC-MS.

$C_{24}H_{16}BrN$: M+1 398.0

Synthesis of Intermediate I-4

Intermediate I-4 (yield: 89%) was synthesized in the same (or substantially the same) manner as in Synthesis of Intermediate I-3, except that 1-bromo-3-iodobenzene was used instead of 1-bromo-4-iodobenzene. The obtained compound was identified by LC-MS.

$C_{24}H_{16}BrN$: M+1 398.0

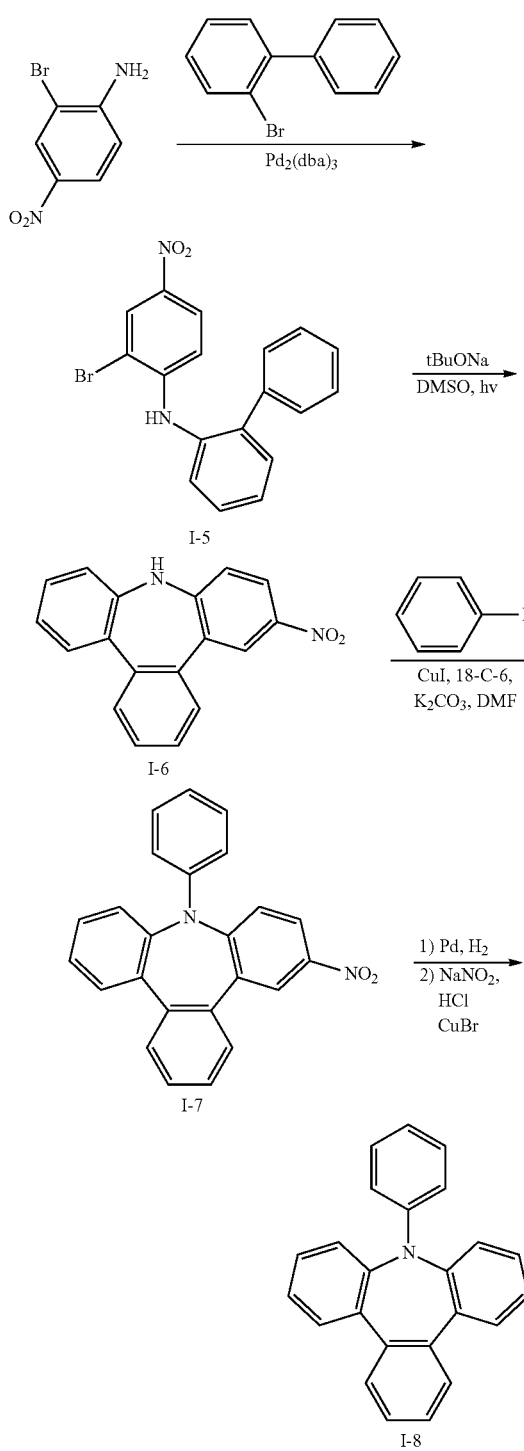

Synthesis of Intermediate I-5

Intermediate I-5 (yield: 73%) was synthesized in the same (or substantially the same) manner as in Synthesis of Intermediate I-1, except that 2-bromo-4-nitroaniline was used instead of 2-bromoaniline. The obtained compound was identified by LC-MS.

$C_{18}H_{13}BrN_2O_2$: M+1 369.0

Synthesis of Intermediate I-6

Intermediate I-6 (yield: 42%) was synthesized in the same (or substantially the same) manner as in Synthesis of Intermediate I-2, except that Intermediate I-5 was used instead of Intermediate I-1. The obtained compound was identified by LC-MS.

$C_{18}H_{12}N_2O_2$: M+1 289.1

Synthesis of Intermediate I-7

Intermediate I-7 (yield: 92%) was synthesized in the same (or substantially the same) manner as in Synthesis of Intermediate I-3, except that Intermediate I-6 was used instead of Intermediate I-2 and iodobenzene was used instead of 1-bromo-4-iodobenzene. The obtained compound was identified by LC-MS.

$C_{24}H_{16}N_2O_2$: M+1 365.1

Synthesis of Intermediate I-8

3.64 g (10.0 mmol) of Intermediate I-7 and 100 mg of Pd on Carbon (10%) were dissolved in 40 mL of methanol, and then the resulting mixture was stirred in a $H_2$ atmosphere for about 4 hours. The obtained reaction mixture was subject to filtration and then dried using $MgSO_4$. Then, a solvent was removed therefrom by evaporation. 20 mL of distilled water was added to the residual, and 5 mL of 10% HCl aqueous solution was added thereto. The result was cooled to a temperature of about 0° C., and a solution, in which 1.0 g (14.4 mmol) of $NaNO_2$ was dissolved in 10 mL of distilled water, was added thereto. The resulting mixture was stirred at a temperature ranging from 0° C. to 5° C. for about 1 hour. 2.87 g (20.0 mmol) of CuBr was added to the solution, and then the resulting solution was stirred at the same temperature for about 2 hours. Then, the resulting solution was heated up to 100° C. and stirred for about 3 hours. The obtained reaction solution was allowed to come to ambient temperature. Then, an extraction process was performed thereon three times by using 30 mL of ethyl ether. The obtained organic layer was dried by using $MgSO_4$. A solvent was next removed therefrom by evaporation. The obtained residue was separated and purified through silica gel column chromatography to obtain 2.98 g of Intermediate I-8 (yield: 75%). The obtained compound was identified by LC-MS.

$C_{24}H_{16}BrN$: M+1 398.0

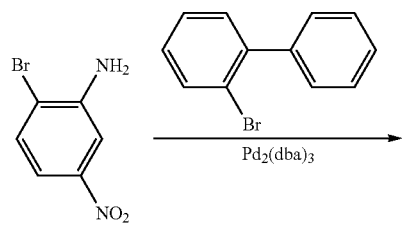

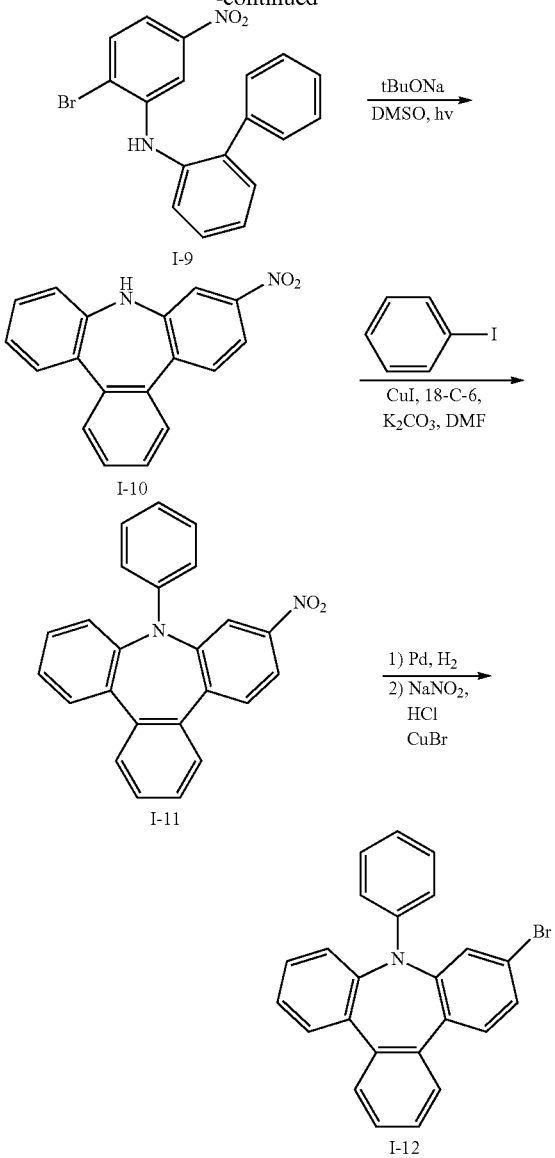

Synthesis of Intermediate I-9

Intermediate I-9 (yield: 78%) was synthesized in the same (or substantially the same) manner as in Synthesis of Intermediate I-5, except that 2-bromo-5-nitroaniline was used instead of 2-bromo-4-nitroaniline. The obtained compound was identified by LC-MS.

$C_{18}H_{13}BrN_2O_2$: M+1 369.0

Synthesis of Intermediate I-10

Intermediate I-10 (yield: 46%) was synthesized in the same (or substantially the same) manner as in Synthesis of Intermediate I-6, except that Intermediate I-9 was used instead of Intermediate I-5. The obtained compound was identified by LC-MS.

$C_{18}H_{12}N_2O_2$: M+1 289.1

Synthesis of Intermediate I-11

Intermediate I-11 (yield: 90%) was synthesized in the same (or substantially the same) manner as in Synthesis of Intermediate I-7, except that Intermediate I-10 was used instead of Intermediate I-6. The obtained compound was identified by LC-MS.

$C_{24}H_{16}N_2O_2$: M+1 365.1

Synthesis of Intermediate I-12

Intermediate I-12 (yield: 73%) was synthesized in the same (or substantially the same) manner as in Synthesis of Intermediate I-8, except that Intermediate I-11 was used instead of Intermediate I-7. The obtained compound was identified by LC-MS.

$C_{24}H_{16}BrN$: M+1 398.0

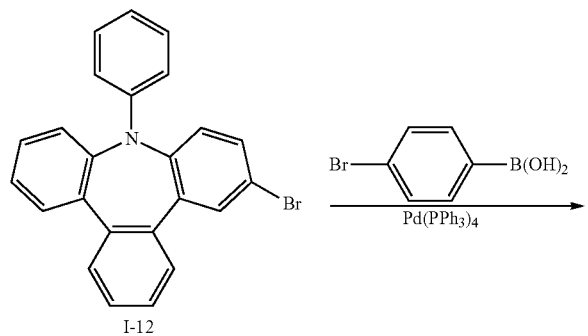

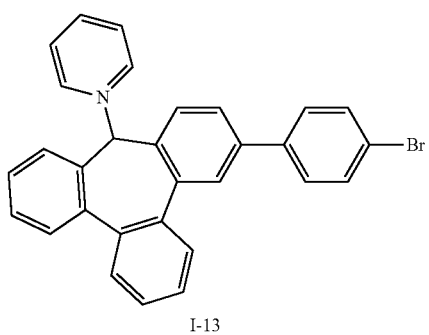

Synthesis of Intermediate I-13

4.38 g (11.0 mmol) of Intermediate I-12, 2.00 g (10.0 mmol) of (4-bromophenyl)boronic acid, 0.58 g (0.5 mmol) of Pd(PPh$_3$)$_4$, and 4.14 g (30.0 mmol) of K$_2$CO$_3$ were dissolved in 40 mL of a mixture solution of THF and H$_2$O (at a volume ratio of 1:1), and then stirred at a temperature of 60° C. for 4 hours. The resulting reaction solution was allowed to come to room temperature, and then 30 mL of water was added thereto. An extraction process was then performed three times therefrom using 30 mL of ethyl ether. The obtained organic layer was dried by using MgSO$_4$. A solvent was next removed therefrom by evaporation. The obtained residue was separated and purified through silica gel column chromatography to obtain 3.75 g of Intermediate I-13 (yield: 79%). The obtained compound was identified by LC-MS.

$C_{30}H_{20}BrN$: M+1 474.1

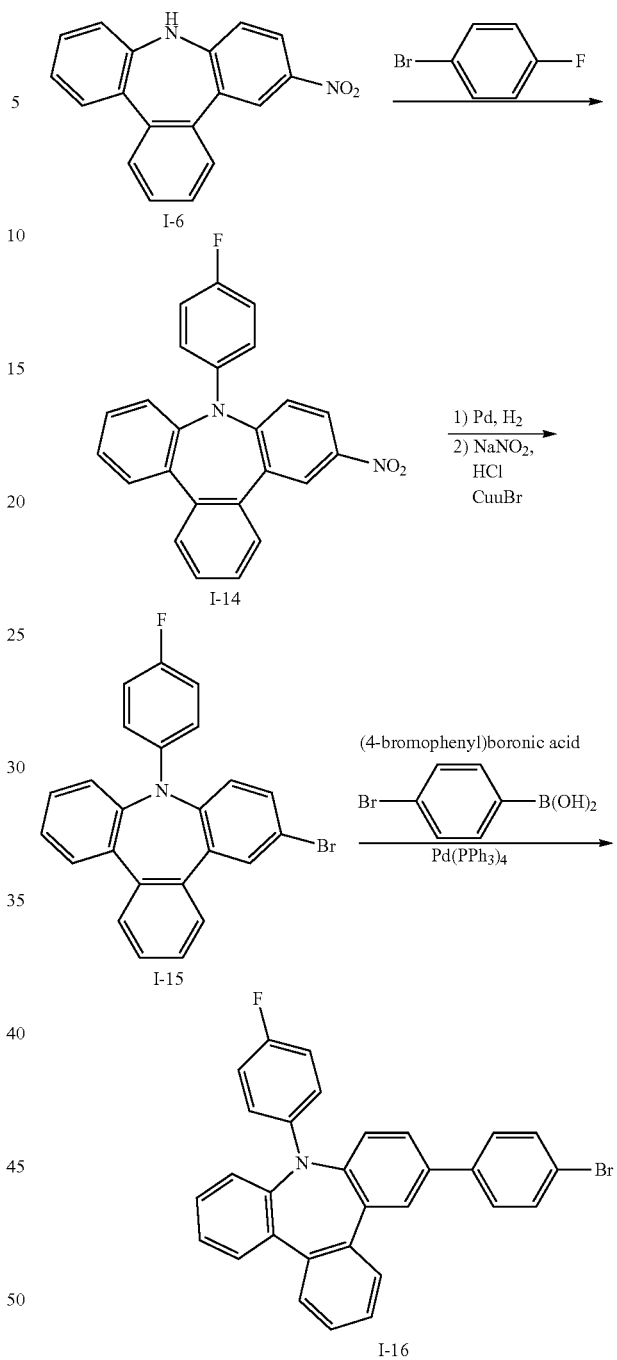

Synthesis of Intermediate I-14

Intermediate I-14 (yield: 84%) was synthesized in the same (or substantially the same) manner as in Synthesis of Intermediate I-7, except that 1-bromo-4-fluorobenzene was used instead of iodobenzene. The obtained compound was identified by LC-MS.

$C_{24}H_{15}FN_2O_2$: M+1 383.1

Synthesis of Intermediate I-15

Intermediate I-15 (yield: 72%) was synthesized in the same (or substantially the same) manner as in Synthesis of Intermediate I-8, except that Intermediate I-14 was used instead of Intermediate I-7. The obtained compound was identified by LC-MS.

C$_{24}$H$_{15}$FN: M+1 416.0

Synthesis of Intermediate I-16

Intermediate I-16 (yield: 76%) was synthesized in the same (or substantially the same) manner as in Synthesis of Intermediate I-13, except that Intermediate I-15 was used instead of Intermediate I-12. The obtained compound was identified by LC-MS.

C$_{30}$H$_{19}$BrFN: M+1 492.1

Synthesis of Intermediates 1-17 to 1-23

Synthesis methods of Intermediates 1-17 to 1-23 should be apparent to those skilled in the art based on the above-described Synthesis methods of Intermediates 1-13 and 1-16 and by using appropriate intermediates.

I-17

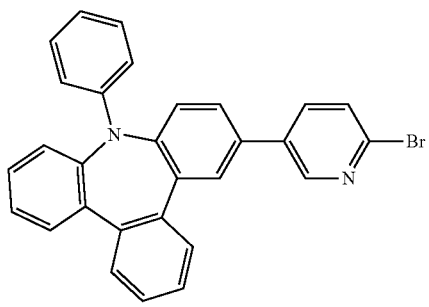

I-18

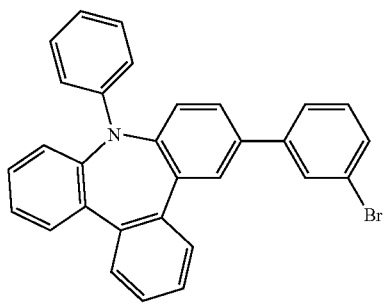

I-19

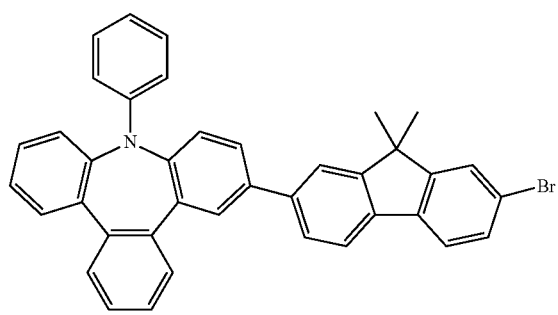

I-20

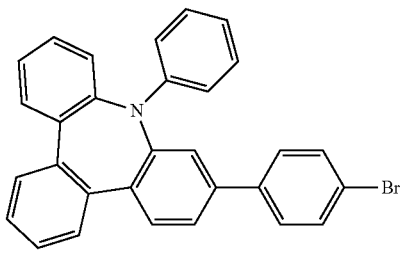

I-21

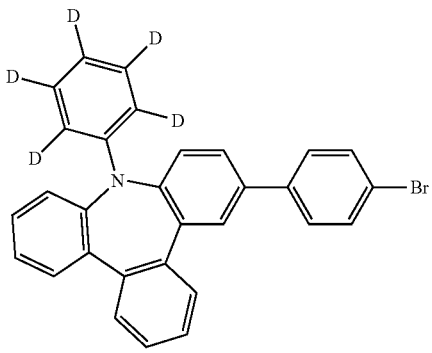

I-22

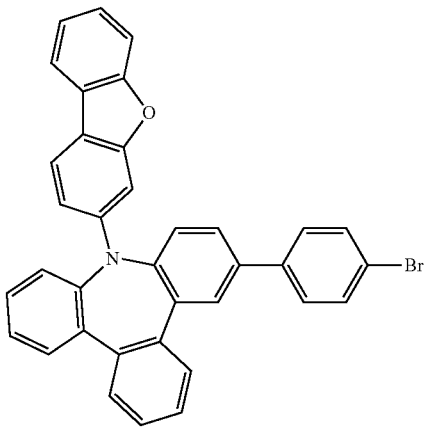

I-23

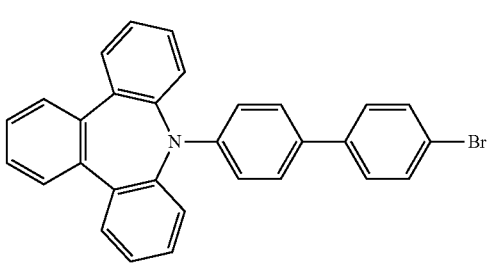

Synthesis of Amine Intermediates A-1 to A-18

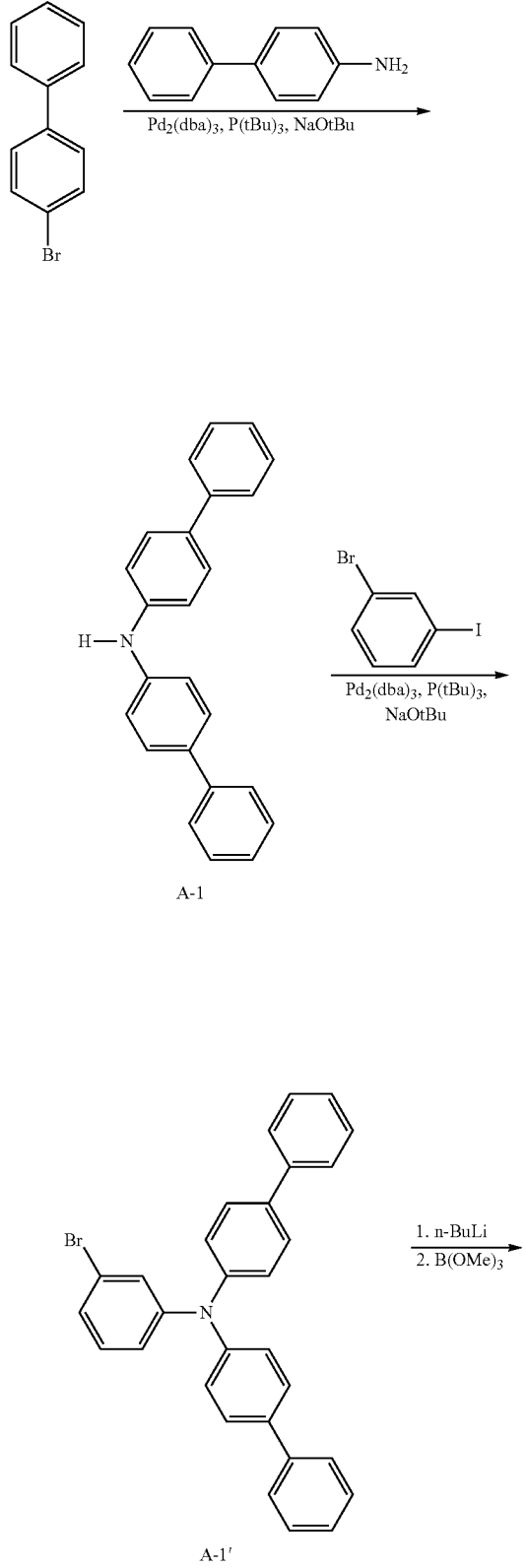

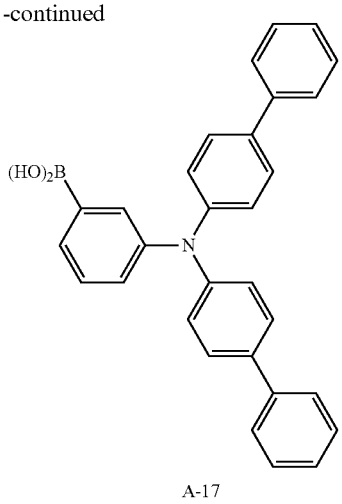

Synthesis of Intermediate A-1

2.33 g (10.0 mmol) of 4-bromo-1,1'-biphenyl, 2.03 g (12.0 mmol) of 4-amino-1,1'-biphenyl, 0.46 g (0.5 mmol) of $Pd_2(dba)_3$, 0.10 g (0.5 mmol) of $P(tBu)_3$, and 1.44 g (15.0 mol) of NaOtBu were dissolved in 30 mL of toluene, and then the resulting mixture was stirred at a temperature of about 80° C. for 5 hours. The obtained reaction solution was allowed to come to ambient temperature. Then, an extraction process was performed thereon three times by using each of 30 mL of water and 30 mL of diethyl ether. The obtained organic layer was dried by using $MgSO_4$. A solvent was next removed therefrom by evaporation. The obtained residue was separated and purified through silica gel column chromatography to obtain 2.76 g of Intermediate A-1 (yield: 86%). The obtained compound was identified by LC-MS.
$C_{24}H_{19}N$: M+1 322.2

Synthesis of Intermediate A-1'

2.57 g (8.0 mmol) of Intermediate A-1, 4.53 g (16.0 mmol) of 1-bromo-3-iodobenzene, 0.37 g (0.4 mmol) of $Pd_2(dba)_3$, 0.08 g (0.4 mmol) of $P(tBu)_3$, and 1.15 g (12.0 mol) of NaOtBu were dissolved in 30 mL of toluene, and then the mixture was stirred at a temperature of about 80° C. for 5 hours. The obtained reaction solution was allowed to come to ambient temperature. Then, an extraction process was performed thereon three times by using each of 30 mL of water and 30 mL of diethyl ether. The obtained organic layer was dried by using $MgSO_4$. A solvent was next removed therefrom by evaporation. The obtained residue was separated and purified through silica gel column chromatography to obtain 2.86 g of Intermediate A-1' (yield: 75%). The obtained compound was identified by LC-MS.
$C_{30}H_{22}BrN$: M+1 476.1

Synthesis of Intermediate A-17

2.86 g (6.0 mmol) of Intermediate A-1' was dissolved in 20 mL of THF. Then, 2.4 mL of n-BuLi (2.5 molar (M) in hexane) was slowly added dropwise thereto at a temperature of −78° C., and then the resulting mixture was stirred at the same temperature for about 1 hour. 1 mL (9.0 mmol) of trimethyl borate was added dropwise to the obtained solution at the same temperature, and then, the solution was allowed to come to ambient temperature and stirred for about 3 hours. 20 mL of water and 10 mL of saturated aqueous ammonium chloride solution were sequentially added to the obtained reaction solution and then stirred for about 1 hour. An extraction process was performed three times thereon using 30 mL of diethyl ether. The obtained organic layer was dried by using MgSO$_4$. A solvent was next removed therefrom by evaporation. The obtained residue was separated and purified through silica gel column chromatography to obtain 2.28 g of Intermediate A-17 (yield: 89%). The obtained compound was identified by LC-MS.

$C_{30}H_{24}BNO_2$: M+1 442.2

Synthesis methods of Intermediates A-2 to A-18 should be apparent to those of ordinary skill in the art based on the abose-described Synthesis methods of Intermediates A-1 and A-17 and by using appropriate intermediates.

A-1

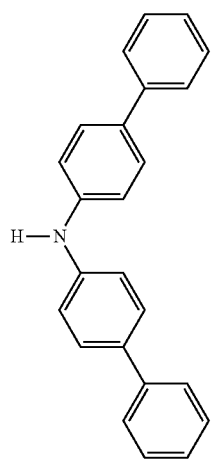

A-2

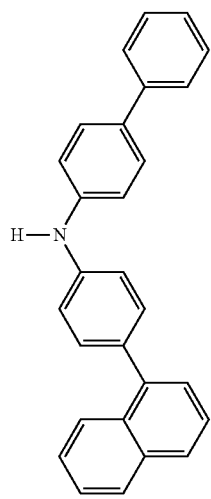

A-3

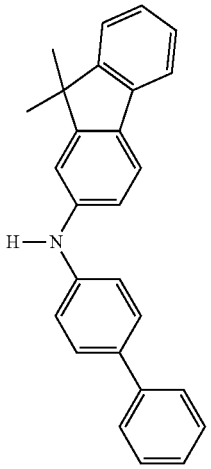

A-4

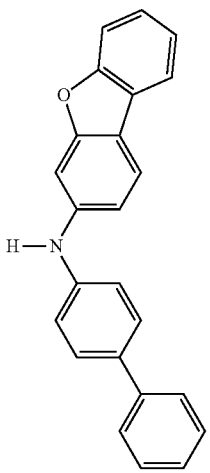

A-5

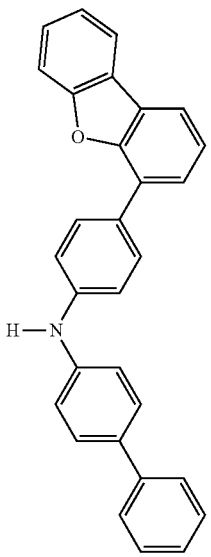

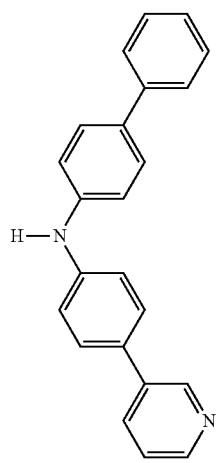
A-6
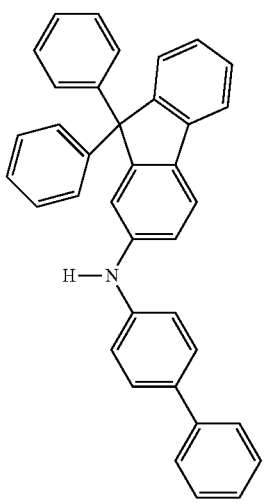
A-9
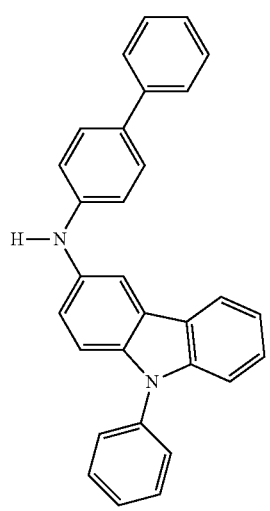
A-7
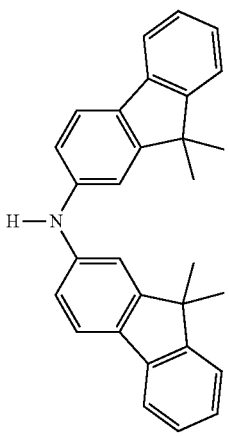
A-10
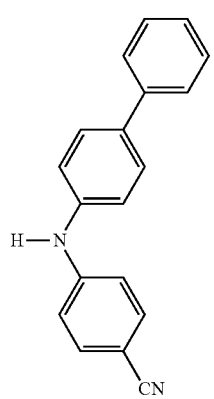
A-8
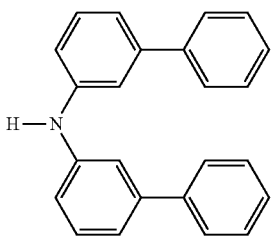
A-11

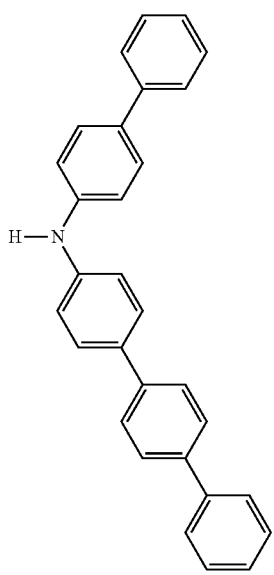
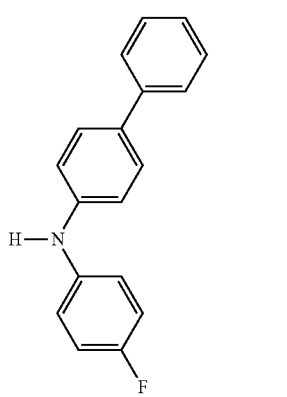
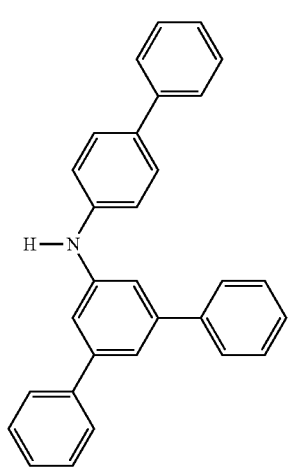
A-12
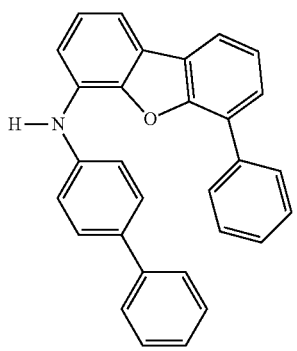
A-15
A-13
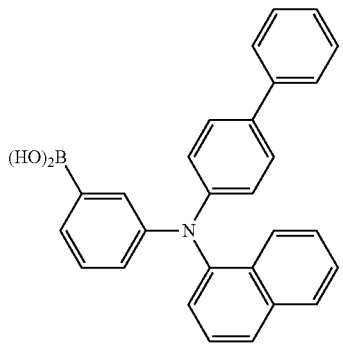
A-16
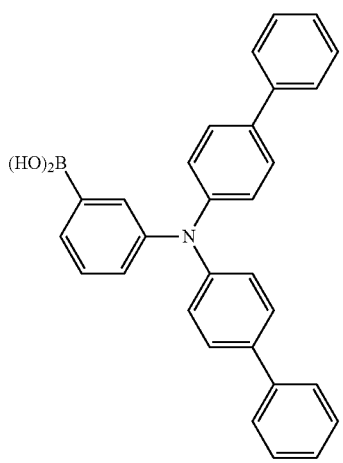
A-17
A-14
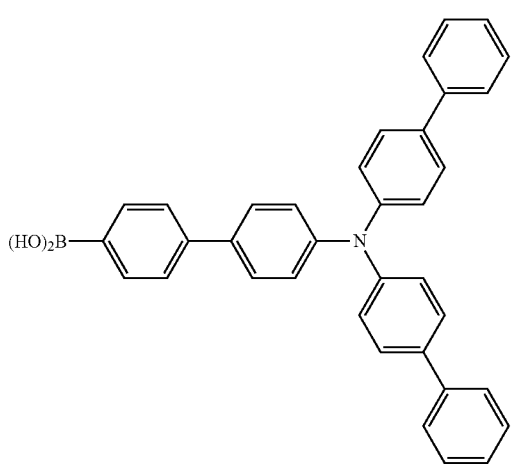
A-18

Synthesis Example: Synthesis of Compounds According to One or More Embodiments

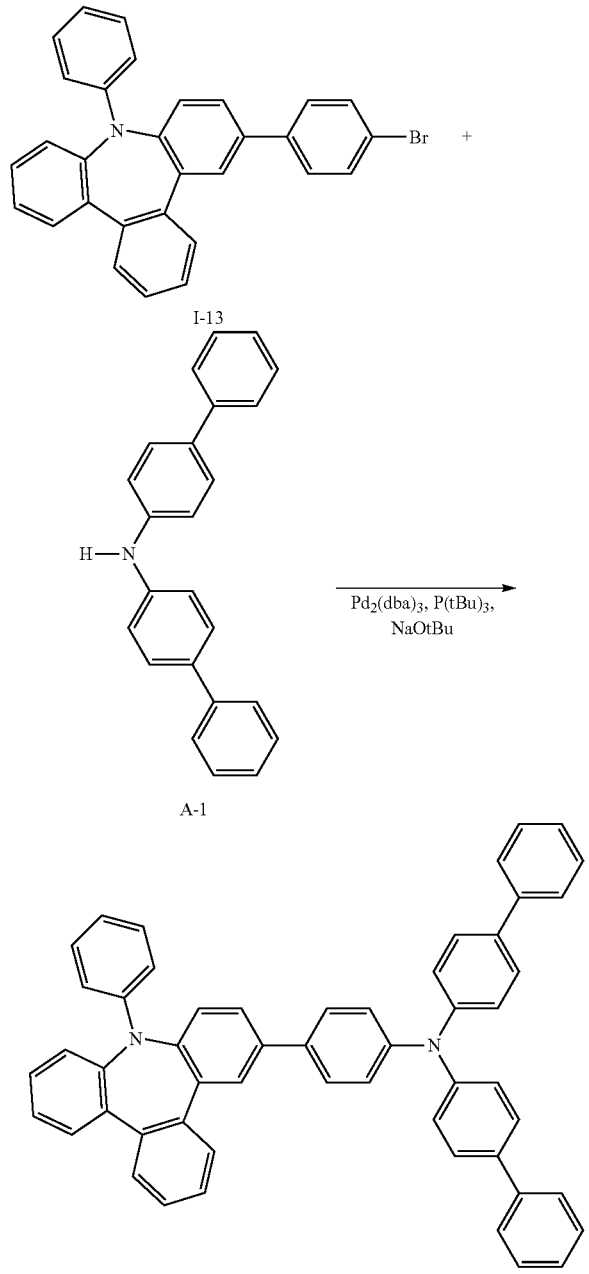

Synthesis of Compound 3

4.74 g (10.0 mmol) of Intermediate I-13, 3.21 g (10.0 mmol) of Intermediate A-1, 0.46 g (0.5 mmol) of Pd$_2$(dba)$_3$, 0.10 g (0.5 mmol) of P(tBu)$_3$, and 1.44 g (15.0 mol) of NaOtBu were dissolved in 30 mL of toluene, and then the resulting mixture was stirred at a temperature of about 80° C. for 5 hours. The obtained reaction solution was allowed to come to ambient temperature. Then, an extraction process was performed thereon three times by using each of 30 mL of water and 30 mL of diethyl ether. The obtained organic layer was dried by using MgSO$_4$. A solvent was next removed therefrom by evaporation. The obtained residue was separated and purified through silica gel column chromatography to obtain 6.65 g of Compound 3 (yield: 93%). The obtained compound was identified by LC-MS and $^1$H-nuclear magnetic resonance (NMR).

$C_{54}H_{35}N_2$: M+1 715.3
$^1$H NMR (CDCl$_3$, 300 MHz) δ ☐ 7.65-7.58 (m, 8H), 7.54-7.37 (m, 15H), 7.29 (dd, 1H), 7.18 (dd, 1H), 7.10-6.99 (m, 4H), 6.95-6.90 (m, 4H), 6.87-6.83 (m, 3H), 6.79-6.72 (m, 2H)

Synthesis of Compound 5

Compound 5 (yield: 91%) was obtained in the same (or substantially the same) manner as in Synthesis of Compound 3, except that Intermediate I-13 was reacted with Intermediate A-2 instead of Intermediate A-1. The obtained compound was identified by LC-MS and $^1$H-NMR.

$C_{58}H_{40}N_2$: M+1 765.3
$^1$H NMR (CDCl$_3$, 300 MHz) δ 7.83-7.80 (m, 2H), 7.66-7.58 (m, 7H), 7.53-7.36 (m, 14H), 7.31 (d, 1H), 7.23 (dt, 1H), 7.18 (dd, 1H), 7.13-7.02 (m, 7H), 6.99-6.94 (m, 2H), 6.89-6.83 (m, 3H), 6.78-6.72 (m, 2H)

Synthesis of Compound 7

Compound 7 (yield: 92%) was obtained in the same (or substantially the same) manner as in Synthesis of Compound 3, except that Intermediate I-13 was reacted with Intermediate A-3 instead of Intermediate A-1. The obtained compound was identified by LC-MS and $^1$H-NMR.

$C_{57}H_{42}N_2$: M+1 755.3
$^1$H NMR (CDCl$_3$, 300 MHz) δ 7.78 (d, 1H), 7.71-7.32 (m, 19H), 7.24-7.07 (m, 7H), 6.99-6.89 (m, 6H), 6.84 (d, 1H), 6.81-6.76 (m, 2H), 1.63 (s, 6H)

Synthesis of Compound 8

Compound 8 (yield: 90%) was obtained in the same (or substantially the same) manner as in Synthesis of Compound 3, except that Intermediate I-13 was reacted with Intermediate A-4 instead of Intermediate A-1. The obtained compound was identified by LC-MS and $^1$H-NMR.

$C_{54}H_{36}N_2O$: M+1 729.3
$^1$H NMR (CDCl$_3$, 300 MHz) δ 7.78-7.72 (m, 2H), 7.69-7.59 (m, 7H), 7.55-7.36 (m, 12H), 7.32 (d, 1H), 7.23 (dd, 1H), 2.18-7.06 (m, 6H), 6.98-6.90 (m, 4H), 6.86 (dt, 1H), 6.83-6.78 (m, 2H)

Synthesis of Compound 10

Compound 10 (yield: 92%) was obtained in the same (or substantially the same) manner as in Synthesis of Compound 3, except that Intermediate I-13 was reacted with Intermediate A-5 instead of Intermediate A-1. The obtained compound was identified by LC-MS and $^1$H-NMR.

$C_{60}H_{40}N_2O$: M+1 805.3
$^1$H NMR (CDCl$_3$, 300 MHz) δ 7.95-7.90 (m, 2H), 7.81 (d, 1H), 7.73-7.62 (m, 7H), 7.58-7.34 (m, 16H), 7.21 (d, 1H), 7.15-7.04 (m, 4H), 7.01-6.96 (m, 2H), 6.92-6.87 (m, 2H), 6.82-6.77 (m, 3H), 6.72-6.69 (m, 2H) Synthesis of Compound 13

Compound 13 (yield: 83%) was obtained in the same (or substantially the same) manner as in Synthesis of Compound 3, except that Intermediate I-13 was reacted with Intermediate A-6 instead of Intermediate A-1. The obtained compound was identified by LC-MS and $^1$H-NMR.

$C_{53}H_{37}N_3$: M+1 716.3

$^1$H NMR (CDCl$_3$, 300 MHz) δ 8.83 (s, 1H), 8.60 (d, 1H), 7.94-7.91 (m, 1H), 7.81-7.65 (m, 6H), 7.60-7.41 (m, 11H), 7.35-7.29 (m, 3H), 7.21 (d, 1H), 7.17-7.08 (m, 4H), 7.03-6.99 (m, 2H), 6.93-6.86 (m, 5H), 6.82-6.78 (m, 2H)

Synthesis of Compound 15

Compound 15 (yield: 79%) was obtained in the same (or substantially the same) manner as in Synthesis of Compound 3, except that Intermediate I-17, instead of Intermediate I-13, was reacted with Intermediate A-1. The obtained compound was identified by LC-MS and $^1$H-NMR.

$C_{53}H_{37}N_3$: M+1 716.3

$^1$H NMR (CDCl$_3$, 300 MHz) δ 8.42 (s, 1), 7.71-7.52 (m, 18H), 7.46-7.39 (m, 3H), 7.34-7.25 (m, 3H), 7.18-7.10 (m, 4H), 7.04-6.96 (m, 6H), 6.84-6.79 (m, 2H)

Synthesis of Compound 22

Compound 22 (yield: 89%) was obtained in the same (or substantially the same) manner as in Synthesis of Compound 3, except that Intermediate I-13 was reacted with Intermediate A-7 instead of Intermediate A-1. The obtained compound was identified by LC-MS and $^1$H-NMR.

$C_{60}H_{41}N_3$: M+1 804.3

$^1$H NMR (CDCl$_3$, 300 MHz) δ 8.23 (d, 1H), 7.69-7.31 (m, 27H), 7.21-7.06 (m, 5H), 6.99-6.90 (m, 6H), 6.84-6.79 (m, 2H)

Synthesis of Compound 28

Compound 28 (yield: 90%) was obtained in the same (or substantially the same) manner as in Synthesis of Compound 3, except that Intermediate I-13 was reacted with Intermediate A-8 instead of Intermediate A-1. The obtained compound was identified by LC-MS and $^1$H-NMR.

$C_{49}H_{33}N_3$: M+1 664.3

$^1$H NMR (CDCl$_3$, 300 MHz) δ 7.71-7.62 (m, 6H), 7.58-7.40 (m, 12H), 7.36 (d, 1H), 7.25-7.10 (m, 5H), 7.03-6.97 (m, 4H), 6.91-6.86 (m, 3H), 6.82-6.76 (m, 2H)

Synthesis of Compound 30

Compound 30 (yield: 92%) was obtained in the same (or substantially the same) manner as in Synthesis of Compound 3, except that Intermediate I-16, instead of Intermediate I-13, was reacted with Intermediate A-1. The obtained compound was identified by LC-MS and $^1$H-NMR.

$C_{54}H_{37}FN_2$: M+1 733.3

1H NMR (CDCl3, 300 MHz) δ 7.69-7.59 (m, 8H), 7.56-7.39 (m, 15H), 7.35 (d, 1H), 7.22-7.02 (m, 9H), 6.94-6.89 (m, 2H), 6.82-6.76 (m, 2H)

Synthesis of Compound 31

Compound 31 (yield: 88%) was obtained in the same (or substantially the same) manner as in Synthesis of Compound 3, except that Intermediate I-21, instead of Intermediate I-13, was reacted with Intermediate A-1. The obtained compound was identified by LC-MS and $^1$H-NMR.

$C_{54}H_{33}D_5N_2$: M+1 720.3

$^1$H NMR (CDCl$_3$, 300 MHz) δ 7.65-7.58 (m, 8H), 7.54-7.37 (m, 15H), 7.31 (d, 1H), 7.21 (d, 1H), 7.13-7.05 (m, 2H), 6.97-6.92 (m, 4H), 6.84-6.79 (m, 2H)

Synthesis of Compound 38

Compound 38 (yield: 93%) was obtained in the same (or substantially the same) manner as in Synthesis of Compound 3, except that Intermediate I-13 was reacted with Intermediate A-9 instead of Intermediate A-1. The obtained compound was identified by LC-MS and $^1$H-NMR.

$C_{67}H_{46}N_2$: M+1 879.4

$^1$H NMR (CDCl$_3$, 300 MHz) δ 7.86 (d, 1H), 7.73-7.42 (m, 18H), 7.34 (d, 1H), 7.27-7.03 (m, 16H), 6.97 (d, 1H), 6.93 (d, 1H), 6.89-6.80 (m, 5H), 6.77 (s, 1H), 6.74-6.69 (m, 2H)

Synthesis of Compound 43

Compound 43 (yield: 91%) was obtained in the same (or substantially the same) manner as in Synthesis of Compound 3, except that Intermediate I-22, instead of Intermediate I-13, was reacted with Intermediate A-1. The obtained compound was identified by LC-MS and $^1$H-NMR.

$C_{60}H_{40}N_2O$: M+1 805.3

$^1$H NMR (CDCl$_3$, 300 MHz) δ 7.74 (d, 2H), 7.69-7.60 (9H), 7.55-7.39 (m, 17H), 7.31 (d, 1H), 7.21-7.02 (m, 5H), 6.97-6.92 (m, 4H), 6.83-6.78 (m, 2H)

Synthesis of Compound 58

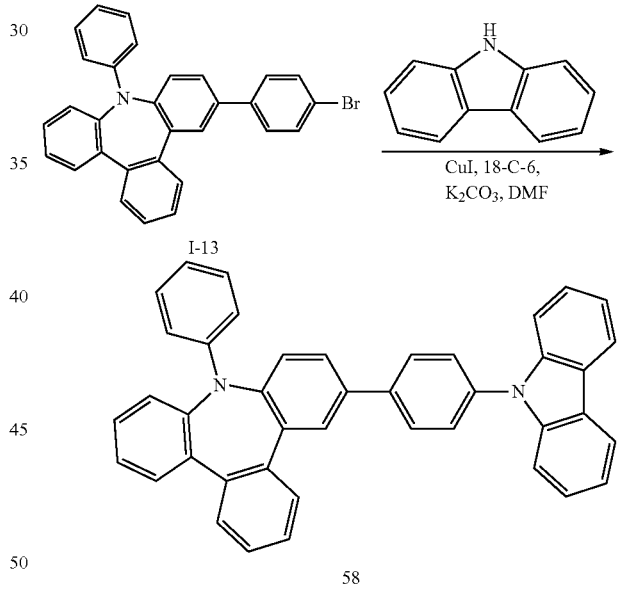

58

2.37 g (5.0 mmol) of Intermediate I-13, 0.92 g (5.0 mmol) of carbazole, 0.1 g (0.5 mmol) of CuI, 0.13 g (0.5 mmol) of 18-Crown-6, and 2.07 g (15.0 mmol) of K$_2$CO$_3$ were dissolved in 20 mL of DMF, and then stirred at a temperature of about 140° C. for about 12 hours. The resulting a reaction solution was allowed to come to ambient temperature. Then, an extraction process was performed thereon three times by using each of 20 mL of water and 20 mL of ethyl ether. The obtained organic layer was dried by using MgSO$_4$. A solvent was next removed therefrom by evaporation. The obtained residue was separated and purified through silica gel column chromatography to obtain 2.33 g of Compound 58 (yield: 83%). The obtained compound was identified by LC-MS and $^1$H-NMR.

$C_{42}H_{28}N_2$: M+1 561.2

$^1$H NMR (CDCl$_3$, 300 MHz) δ 8.12 (d, 2H), 7.74-7.63 (m, 4H), 7.52-7.25 (m, 14H), 7.19 (d, 1H), 7.09-7.01 (m, 4H), 6.96-6.91 (m, 1H), 6.84-6.79 (m, 2H)

Synthesis of Compound 61

Compound 61 (yield: 90%) was obtained in the same (or substantially the same) manner as in Synthesis of Compound 3, except that Intermediate I-18, instead of Intermediate I-13, was reacted with Intermediate A-1. The obtained compound was identified by LC-MS and $^1$H-NMR.

C$_{54}$H$_{38}$N$_2$: M+1 715.3

$^1$H NMR (CDCl$_3$, 300 MHz) δ 7.69-7.61 (m, 7H), 7.56-7.27 (m, 16H), 7.21-7.14 (m, 2H), 7.09-7.01 (m, 5H), 6.94-6.86 (m, 5H), 6.82-6.76 (m, 3H)

Synthesis of Compound 66

Compound 66 (yield: 91%) was obtained in the same (or substantially the same) manner as in Synthesis of Compound 3, except that Intermediate I-20 was used instead of Intermediate I-13, and Intermediate A-3 was used instead of Intermediate A-1. The obtained compound was identified by LC-MS and $^1$H-NMR.

C$_{57}$H$_{42}$N$_2$: M+1 755.3

$^1$H NMR (CDCl$_3$, 300 MHz) δ 7.78 (d, 1H), 7.71-7.29 (m, 19H), 7.21 (s, 1H), 7.17-7.02 (m, 6H), 6.97-6.91 (m, 6H), 6.86 (s, 1H), 6.82-6.76 (m, 2H), 1.61 (s, 6H)

Synthesis of Compound 68

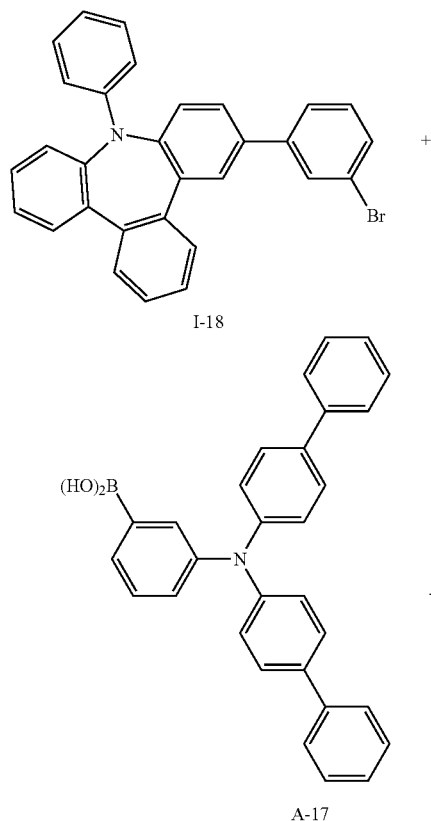

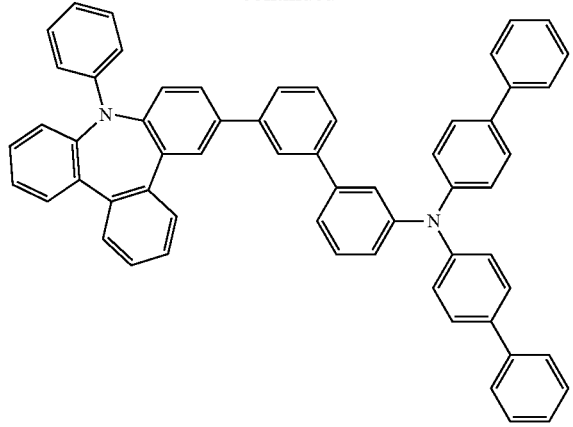

2.37 g (5.0 mmol) of Intermediate I-18, 2.21 g (5.0 mmol) of Intermediate A-17, 0.29 g (0.25 mmol) of Pd(PPh$_3$)$_4$, and 2.07 g (15.0 mmol) of K$_2$CO$_3$ were dissolved in 20 mL of a mixture solution of THF and H$_2$O (at a volume ratio of 1:1), and was stirred at 60° C. for 4 hours. The resulting reaction solution was allowed to come to room temperature, and then 20 mL of water was added thereto. An extraction process was then performed three times therefrom using 20 mL of ethyl ether. The obtained organic layer was dried by using MgSO$_4$. A solvent was next removed therefrom by evaporation. The obtained residue was separated and purified through silica gel column chromatography to obtain 3.36 g of Compound 68 (yield: 85%). The obtained compound was identified by LC-MS and $^1$H-NMR.

C$_{60}$H$_{42}$N$_2$: M+1 791.3

$^1$H NMR (CDCl$_3$, 300 MHz) δ 7.81 (s, 1H), 7.68-7.39 (m, 23H), 7.32-7.23 (m, 3H), 7.18-7.02 (m, 7H), 6.95-6.90 (m, 5H), 6.84-6.79 (m, 3H)

Synthesis of Compound 70

Compound 70 (yield: 87%) was obtained in the same (or substantially the same) manner as in Synthesis of Compound 3, except that Intermediate I-19 was used instead of Intermediate I-13, and N-phenylnaphthalen-1-amine was used instead of Intermediate A-1. The obtained compound was identified by LC-MS and $^1$H-NMR.

C$_{55}$H$_{40}$H$_2$: M+1 729.3

$^1$H NMR (CDCl$_3$, 300 MHz) δ 8.13 (d, 1H), 7.87 (d, 1H), 7.73-7.28 (m, 16H), 7.15-7.03 (m, 7H), 6.97-6.91 (m, 4H), 6.86-6.82 (m, 3H), 6.79-6.72 (m, 2H), 1.64 (s, 6H)

Synthesis of Compound 81

Compound 81 (yield: 81%) was obtained in the same (or substantially the same) manner as in Synthesis of Compound 3, except that Intermediate I-8 was used instead of Intermediate I-13, and Intermediate A-10 was used instead of Intermediate A-1. The obtained compound was identified by LC-MS and $^1$H-NMR.

C$_{54}$H$_{42}$N$_2$: M+1 719.3

$^1$H NMR (CDCl$_3$, 300 MHz) δ 7.76 (d, 2H), 7.71-7.60 (m, 4H), 7.49-7.32 (m, 7H), 7.24-7.07 (m, 8H), 7.01-6.94 (m, 4H), 6.89-6.82 (m, 3H), 6.77-6.71 (m, 2H), 1.63 (s, 12H)

Synthesis of Compound 85

Compound 85 (yield: 83%) was obtained in the same (or substantially the same) manner as in Synthesis of Compound 3, except that Intermediate I-8 was used instead of Intermediate I-13, and Intermediate A-11 was used instead of Intermediate A-1. The obtained compound was identified by LC-MS and $^1$H-NMR.

$C_{45}H_{34}N_2$: M+1 639.3

$^1$H NMR (CDCl$_3$, 300 MHz) δ 7.69-7.58 (m, 6H), 7.48-7.33 (m, 12H), 7.22-7.02 (m, 10H), 6.96-6.88 (m, 2H), 6.84-6.80 (m, 2H), 6.76-6.71 (m, 2H)

Synthesis of Compound 88

Compound 88 (yield: 85%) was obtained in the same (or substantially the same) manner as in Synthesis of Compound 3, except that Intermediate I-8 was used instead of Intermediate I-13, and Intermediate A-12 was used instead of Intermediate A-1. The obtained compound was identified by LC-MS and $^1$H-NMR.

$C_{54}H_{38}N_2$: M+1 715.3

$^1$H NMR (CDCl$_3$, 300 MHz) δ 7.71-7.29 (m, 24H), 7.17 (s, 1H), 7.12-7.02 (m, 4H), 6.97 (d, 1H), 6.93-6.84 (m, 6H), 6.78-6.72 (m, 2H)

Synthesis of Compound 92

Compound 92 (yield: 87%) was obtained in the same (or substantially the same) manner as in Synthesis of Compound 3, except that Intermediate I-3 was used instead of Intermediate I-13, and Intermediate A-13 was used instead of Intermediate A-1. The obtained compound was identified by LC-MS and $^1$H-NMR.

$C_{42}H_{29}FN_2$: M+1 581.2

$^1$H NMR (CDCl$_3$, 300 MHz) δ 7.69-7.59 (m, 4H), 7.56-7.35 (m, 9H), 7.18-7.07 (m, 6H), 7.02-6.92 (m, 4H), 6.84-6.72 (m, 6H)

Synthesis of Compound 95

Compound 95 (yield: 79%) was obtained in the same (or substantially the same) manner as in Synthesis of Compound 3, except that Intermediate I-3 was used instead of Intermediate I-13, and Intermediate A-14 was used instead of Intermediate A-1. The obtained compound was identified by LC-MS and $^1$H-NMR.

$C_{54}H_{38}N_2$: M+1 715.3

$^1$H NMR (CDCl$_3$, 300 MHz) δ 7.69-7.57 (m, 8H), 7.51-7.38 (m, 16H), 7.13-7.07 (m, 6H), 6.97 (d, 2H), 6.86-6.70 (m, 6H)

Synthesis of Compound 99

Compound 99 (yield: 81%) was obtained in the same (or substantially the same) manner as in Synthesis of Compound 3, except that Intermediate I-3 was used instead of Intermediate I-13, and Intermediate A-15 was used instead of Intermediate A-1. The obtained compound was identified by LC-MS and $^1$H-NMR.

$C_{54}H_{36}N_2O$: M+1 729.3

$^1$H NMR (CDCl$_3$, 300 MHz) δ 7.90 (dd, 1H), 7.78 (d, 1H), 7.72-7.57 (m, 7H), 7.54-7.33 (m, 12H), 7.24 (t, 1H), 7.16-7.09 (m, 7H), 7.03 (t, 1H), 6.93-6.89 (m, 2H), 6.82-6.74 (m, 4H)

Synthesis of Compound 105

Compound 105 (yield: 86%) was obtained in the same (or substantially the same) manner as in Synthesis of Compound 58, except that Intermediate I-23 was used instead of Intermediate I-13, and 3,6-diphenyl-9H-carbazole was used instead of carbazole. The obtained compound was identified by LC-MS and $^1$H-NMR.

$C_{54}H_{36}N_2$: M+1 713.3

$^1$H NMR (CDCl$_3$, 300 MHz) δ 8.16 (s, 2H), 7.75-7.69 (m, 6H), 7.63-7.37 (m, 20H), 7.15-7.07 (m, 6H), 6.86-6.80 (m, 2H)

Synthesis of Compound 106

Compound 106 (yield: 88%) was obtained in the same (or substantially the same) manner as in Synthesis of Compound 3, except that Intermediate I-23, instead of Intermediate I-13, was reacted with Intermediate A-1. The obtained compound was identified by LC-MS and $^1$H-NMR.

$C_{54}H_{38}N_2$: M+1 715.3

$^1$H NMR (CDCl$_3$, 300 MHz) δ 7.65-7.57 (m, 6H), 7.52-7.33 (m, 18H), 7.13-7.05 (m, 6H), 6.95-6.88 (m, 6H), 6.79-6.72 (m, 2H)

Synthesis of Compound 107

Compound 107 (yield: 81%) was obtained in the same (or substantially the same) manner as in Synthesis of Compound 68, except that Intermediate I-4 was used instead of Intermediate I-18, and Intermediate A-16 was used instead of Intermediate A-17. The obtained compound was identified by LC-MS and $^1$H-NMR.

$C_{52}H_{36}N_2$: M+1 689.3

$^1$H NMR (CDCl$_3$, 300 MHz) δ 8.13 (d, 1H), 7.87 (d, 1H), 7.68-7.38 (m, 16H), 7.29-7.18 (m, 5H), 7.09-6.98 (m, 6H), 6.93-6.81 (m, 5H), 6.74-6.70 (m, 2H)

Synthesis of Compound 112

Compound 112 (yield: 80%) was obtained in the same (or substantially the same) manner as in Synthesis of Compound 68, except that Intermediate I-3 was used instead of Intermediate I-18, and Intermediate A-18 was used instead of Intermediate A-17. The obtained compound was identified by LC-MS and $^1$H-NMR.

$C_{60}H_{42}N_2$: M+1 791.3

$^1$H NMR (CDCl$_3$, 300 MHz) δ 7.72-7.67 (m, 4H), 7.65-7.56 (m, 6H), 7.52-7.33 (m, 18H), 7.23-7.15 (m, 6H), 7.06-6.96 (m, 6H), 6.83-6.78 (m, 2H)

EXAMPLE

Example 1

A substrate, on which ITO, Ag, and ITO were deposited at a thickness of about 70 Å, 1000 Å, and 70 Å, respectively, was cut to a size of 50 millimeters (mm)×50 mm×0.5 mm, sonicated in isopropyl alcohol and pure water for 5 minutes in each solvent, and cleaned by exposure to ultraviolet rays with ozone, to use the resulting glass substrate as an anode. Then, the glass substrate was mounted on a vacuum-deposition device.

N-([1,1'-biphenyl]-4-yl)-9,9-dimethyl-N-(4-(9-phenyl-9H-carbazol-3-yl)phenyl)-9H-fluoren-2-amine (HT1) and F4-TCNQ were co-vacuum deposited on the ITO substrate at a weight ratio of about 98:2 to form a hole injection layer having a thickness of about 100 Å. Compound HT1 was vacuum-deposited on the hole injection layer to form a first hole transport layer having a thickness of about 1,200 Å. Compound 3 was vacuum-deposited on the first hole transport layer to form a second hole transport layer having a thickness of about 100 Å. Then, 9,10-di-naphthalene-2-yl-anthracene (ADN) (as a blue fluorescent host) and N,N,N',N'-tetraphenyl-pyrene-1,6-diamine (TPD) (as a blue florescent dopant) were co-deposited on the second hole transport layer at a weight ratio of about 98:2 to form an emission layer having a thickness of about 300 Å. Then, 2-(4-(9,10-di(naphthalen-2-yl)anthracen-2-yl)phenyl)-1-phenyl-1H-benzo[d]imidazole (L201) was deposited on the emission layer to form an electron transport layer having a thickness of about 300 Å. LiF, which is an alkali metal halide, was deposited on the electron transport layer to form an electron injection layer having a thickness of about 10 Å, and Mg:Ag was vacuum-deposited on the electron injection layer at a weight ratio of about 90:10 to form a cathode having a thickness of about 120 Å, thereby completing the manufacture of an organic light-emitting device.

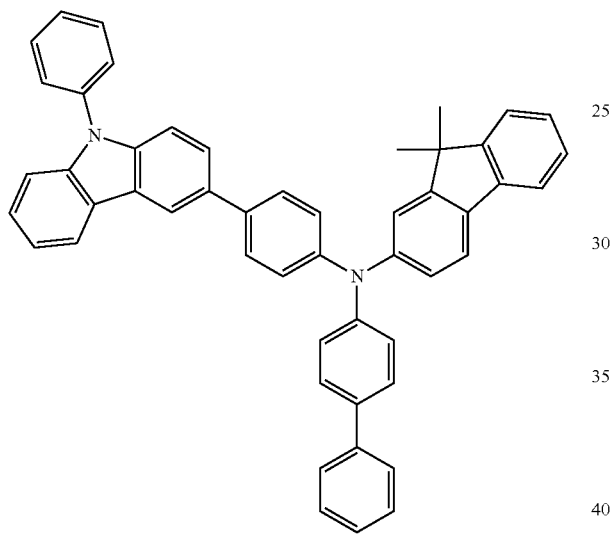

HT1

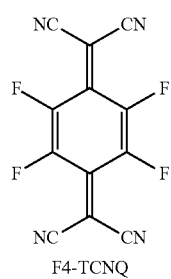

F4-TCNQ

-continued

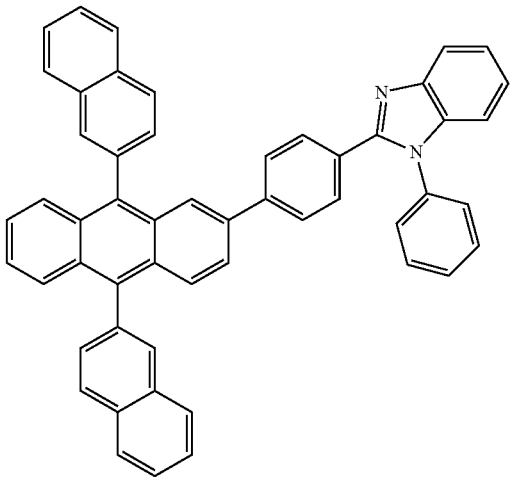

L201

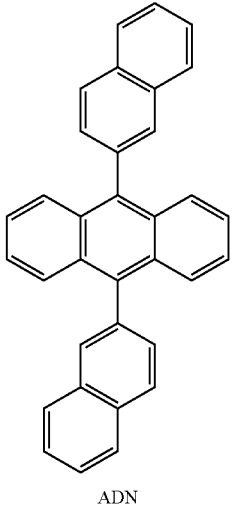

ADN

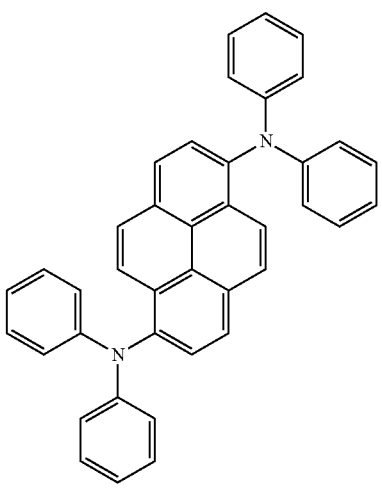

TPD

Examples 2 to 28

Organic light-emitting devices were manufactured in the same (or substantially the same) manner as in Example 1, except that Compounds 5 to 112 (as shown in Table 1) were used instead of Compound 3 to form a second hole transport layer.

Examples 29 to 38

Organic light-emitting devices were manufactured in the same (or substantially the same) manner as in Example 1, except that Compounds 7 to 105 (as shown in Table 1) were used instead of Compound HT1 to form a first hole transport layer.

Comparative Examples 1 to 4

Organic light-emitting device were manufactured in the same (or substantially the same) manner as in Example 1, except that Compounds A, D, F, and G were respectively used instead of Compound 3 to form a second hole transport layer.

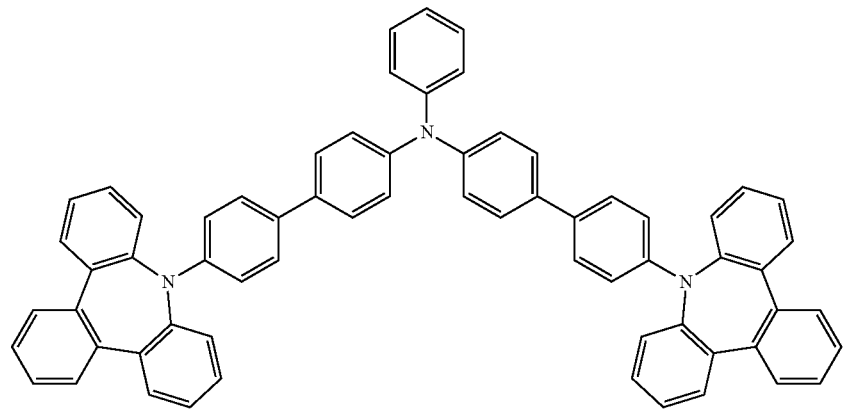

A

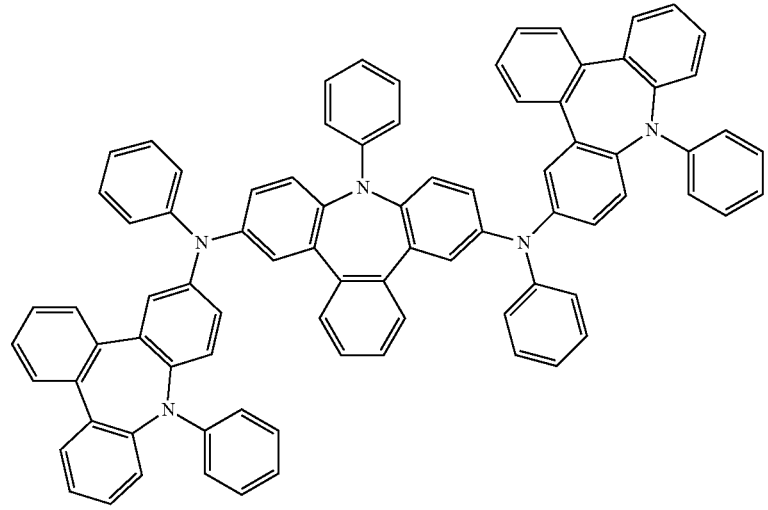

D

-continued

F

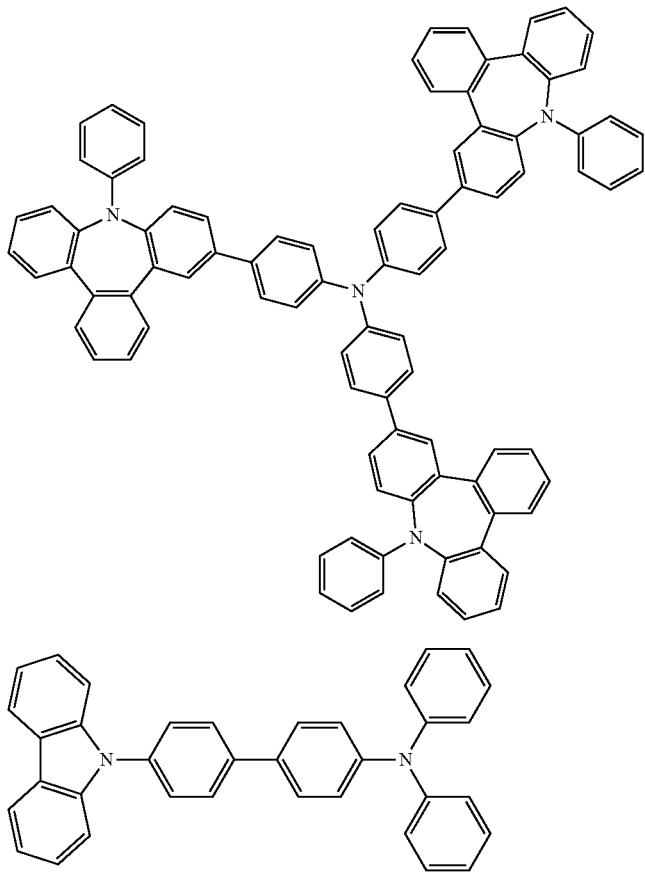

G

The device performance, i.e., driving voltage, luminance, efficiency, and color-coordinate, of the organic light-emitting devices manufactured in Examples 1 to 38 and Comparative Examples 1 to 4 were measured at a current density of about 10 mA/cm², and the time until the initial luminance was reduced by a half was measured at a current density of about 50 mA/cm². The results thereof are shown in Table 1.

Referring to the results shown in Table 1, when the compounds according to one or more embodiments of the present disclosure are used in a first hole transport layer and/or a second hole transport layer, the organic light-emitting device may exhibit improved or same driving voltage and improved efficiency, and luminance half-lifespan thereof may also improve, as compared to the organic light-emitting devices of Comparative Examples.

TABLE 1

|  | First hole transport layer | Second hole transport layer | Driving voltage (V) | Current density (mA/cm²) | Efficiency (cd/A) | Color-coordinate CIE(x, y) | Half lifespan (@1.0 mA/cm²) |
|---|---|---|---|---|---|---|---|
| Example 1 | HT1 | Compound 3 | 4.51 | 10 | 5.45 | 0.140, 0.051 | 214 |
| Example 2 | HT1 | Compound 5 | 4.52 | 10 | 5.43 | 0.141, 0.052 | 194 |
| Example 3 | HT1 | Compound 7 | 4.74 | 10 | 5.06 | 0.141, 0.050 | 164 |
| Example 4 | HT1 | Compound 8 | 4.72 | 10 | 5.13 | 0.140, 0.052 | 161 |
| Example 5 | HT1 | Compound 10 | 4.52 | 10 | 5.32 | 0.141, 0.052 | 211 |
| Example 6 | HT1 | Compound 13 | 4.64 | 10 | 5.21 | 0.141, 0.052 | 78 |
| Example 7 | HT1 | Compound 15 | 4.52 | 10 | 5.14 | 0.142, 0.051 | 107 |
| Example 8 | HT1 | Compound 22 | 4.75 | 10 | 4.92 | 0.140, 0.053 | 125 |
| Example 9 | HT1 | Compound 28 | 4.61 | 10 | 5.31 | 0.141, 0.052 | 131 |

TABLE 1-continued

|  | First hole transport layer | Second hole transport layer | Driving voltage (V) | Current density (mA/cm$^2$) | Efficiency (cd/A) | Color-coordinate CIE(x, y) | Half lifespan (@1.0 mA/cm$^2$) |
|---|---|---|---|---|---|---|---|
| Example 10 | HT1 | Compound 30 | 4.51 | 10 | 5.42 | 0.141, 0.052 | 194 |
| Example 11 | HT1 | Compound 31 | 4.53 | 10 | 5.41 | 0.141, 0.051 | 186 |
| Example 12 | HT1 | Compound 38 | 4.61 | 10 | 5.15 | 0.141, 0.053 | 142 |
| Example 13 | HT1 | Compound 43 | 4.52 | 10 | 5.32 | 0.140, 0.052 | 188 |
| Example 14 | HT1 | Compound 58 | 4.66 | 10 | 5.08 | 0.140, 0.053 | 129 |
| Example 15 | HT1 | Compound 61 | 4.50 | 10 | 5.45 | 0.141, 0.052 | 197 |
| Example 16 | HT1 | Compound 66 | 4.64 | 10 | 5.04 | 0.141, 0.052 | 156 |
| Example 17 | HT1 | Compound 68 | 4.50 | 10 | 5.24 | 0.141, 0.051 | 182 |
| Example 18 | HT1 | Compound 70 | 4.73 | 10 | 5.01 | 0.141, 0.051 | 148 |
| Example 19 | HT1 | Compound 81 | 4.57 | 10 | 5.41 | 0.141, 0.052 | 159 |
| Example 20 | HT1 | Compound 85 | 4.61 | 10 | 5.32 | 0.140, 0.053 | 176 |
| Example 21 | HT1 | Compound 88 | 4.61 | 10 | 5.31 | 0.140, 0.052 | 168 |
| Example 22 | HT1 | Compound 92 | 4.52 | 10 | 5.16 | 0.140, 0.052 | 135 |
| Example 23 | HT1 | Compound 95 | 4.52 | 10 | 5.38 | 0.140, 0.052 | 176 |
| Example 24 | HT1 | Compound 99 | 4.55 | 10 | 5.39 | 0.140, 0.053 | 169 |
| Example 25 | HT1 | Compound 105 | 4.67 | 10 | 4.99 | 0.141, 0.052 | 124 |
| Example 26 | HT1 | Compound 106 | 4.51 | 10 | 5.45 | 0.141, 0.052 | 207 |
| Example 27 | HT1 | Compound 107 | 4.50 | 10 | 5.44 | 0.140, 0.052 | 204 |
| Example 28 | HT1 | Compound 112 | 4.52 | 10 | 5.43 | 0.140, 0.053 | 199 |
| Example 29 | Compound 7 | Compound 3 | 4.51 | 10 | 5.49 | 0.141, 0.052 | 201 |
| Example 30 | Compound 8 | Compound 3 | 4.52 | 10 | 5.43 | 0.141, 0.052 | 214 |
| Example 31 | Compound 13 | Compound 3 | 4.54 | 10 | 5.46 | 0.140, 0.052 | 141 |
| Example 32 | Compound 22 | Compound 3 | 4.50 | 10 | 5.48 | 0.140, 0.053 | 198 |
| Example 33 | Compound 58 | Compound 3 | 4.63 | 10 | 5.10 | 0.141, 0.052 | 127 |
| Example 34 | Compound 70 | Compound 3 | 4.52 | 10 | 5.43 | 0.141, 0.052 | 203 |
| Example 35 | Compound 85 | Compound 3 | 4.58 | 10 | 5.38 | 0.140, 0.052 | 189 |
| Example 36 | Compound 88 | Compound 3 | 4.59 | 10 | 5.44 | 0.140, 0.053 | 198 |
| Example 37 | Compound 99 | Compound 3 | 4.56 | 10 | 5.46 | 0.141, 0.052 | 168 |
| Example 38 | Compound 105 | Compound 3 | 4.67 | 10 | 4.98 | 0.141, 0.052 | 151 |
| Comparative Example 1 | HT1 | A | 5.31 | 10 | 4.38 | 0.140, 0.053 | 64 |
| Comparative Example 2 | HT1 | D | 4.91 | 10 | 4.42 | 0.141, 0.052 | 50 |
| Comparative Example 3 | HT1 | F | 4.82 | 10 | 4.44 | 0.141, 0.052 | 66 |
| Comparative Example 4 | HT1 | G | 4.75 | 10 | 4.53 | 0.141, 0.051 | 75 |

According to one or more embodiments of the present disclosure, due to the inclusion of the compound of Formula 1 according to an embodiment, characteristics of an organic light-emitting device may be improved.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the drawing, it will be understood by those of ordinary skill in the art that various changes in form and details may be made therein without departing from the spirit and scope of the present disclosure as defined by the following claims and equivalents thereof.

What is claimed is:
1. A compound represented by Formula 1:

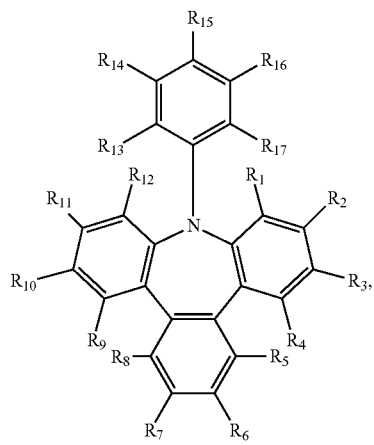

Formula 1 wherein, in Formula 1,
$R_1$, $R_{12}$, $R_{13}$, and $R_{17}$ are each independently hydrogen or deuterium;

$R_2$ to $R_{11}$ and $R_{14}$ to $R_{16}$ are each independently selected from hydrogen, deuterium, halogen, an amino group, a nitro group, a nitrile group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, provided that $R_{14}$ and $R_{16}$ are not both a substituted or unsubstituted $C_1$-$C_{60}$ heteroaryl group at the same time;

wherein only one selected from $R_5$ to $R_8$ comprises a group represented by Formula 1-1:

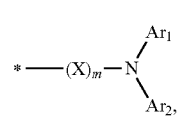

Formula 1-1 wherein, in Formula 1-1, $Ar_1$ and $Ar_2$ are each independently selected from a group represented by one of Formulae 3a, 3b, and 3d to 3g, and $Ar_1$ and $Ar_2$ are not linked to each other to form a ring:

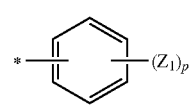

3a

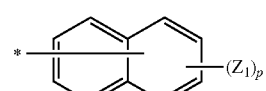

3b

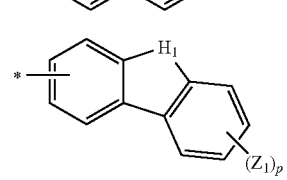

3c

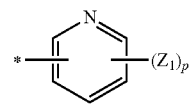

3d

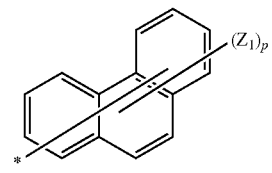

3e

-continued

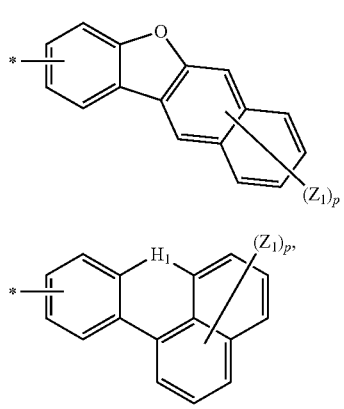

3f

3g wherein, in Formulae 3a, 3b, and 3d to 3g,
$H_1$ in Formula 3g is selected from O, S, $NR_{21}$, and $CR_{22}R_{23}$;
$R_{21}$ to $R_{23}$, and $Z_1$ are each independently selected from hydrogen, deuterium, halogen, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and $Si(Q_{13})(Q_{14})(Q_{15})$;
p in Formula 3a is an integer selected from 1 to 5, p in Formula 3b is an integer selected from 1 to 7, p in Formula 3d is an integer selected from 1 to 4 and p in Formulae 3e to 3g is an integer selected from 1 to 6,
wherein when p is 2 or more, 2 or more $Z_1$(s) are identical to or different from each other; and
*indicates a binding site,
provided that when $Ar_1$ and $Ar_2$ are both represented by Formula 3a at the same time, at least one $Z_1$ is selected from deuterium, halogen, a substituted or unsubstituted $C_1$-$C_{20}$ alkyl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, and $Si(Q_{13})(Q_{14})(Q_{15})$;
X is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group; and
m is an integer selected from 0 to 5, and when m is 2 or more, 2 or more X(s) are identical to or different from each other;
wherein at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, substituted monovalent non-aromatic condensed heteropolycyclic group, substituted $C_6$-$C_{60}$ arylene group, substituted $C_1$-$C_{60}$ heteroarylene group, substituted divalent non-aromatic condensed polycyclic group, and substituted divalent non-aromatic condensed heteropolycyclic group is selected from the group consisting of:
deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group,
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$,
a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group,
a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q22)$, —$Si(Q_{23})(Q_{24})(Q_{25})$, and —$B(Q_{26})(Q_{27})$, and
$Si(Q_{13})(Q_{14})(Q_{15})$,
wherein $Q_{11}$ to $Q_{17}$ and $Q_{21}$ to $Q_{27}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group, wherein the compound represented by Formula 1 includes only one azepine moiety.

2. The compound of claim 1, wherein two or more adjacent substituents selected from $R_{14}$ to $R_{16}$ in Formula 1 are linked to each other to form a ring.

3. The compound of claim 1, wherein m in Formula 1-1 is an integer selected from 0 to 3.

4. The compound of claim 1, wherein $R_4$ and the remainder of $R_5$ to $R_9$ in Formula 1 are each independently hydrogen or deuterium.

5. The compound of claim 1, wherein X in Formula 1-1 is a group represented by one of Formulae 2a to 2f:

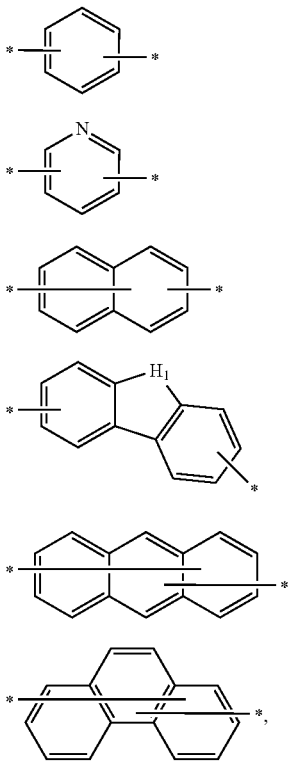

wherein, in Formulae 2a to 2f, $H_1$ is selected from O, S, $NR_{21}$, and $CR_{22}R_{23}$, $R_{21}$ to $R_{23}$ are each independently selected from hydrogen, deuterium, halogen, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group; and

* indicates a binding site.

6. An organic light-emitting device comprising:
a first electrode;
a second electrode facing the first electrode; and
an organic layer between the first electrode and the second electrode, the organic layer comprising an emission layer, wherein the organic layer comprises the compound represented by Formula 1 of claim 1.

7. The organic light-emitting device of claim 6, wherein the first electrode is an anode,
the second electrode is a cathode, and
the organic layer further comprises:
i) a hole transport region between the first electrode and the emission layer, the hole transport region comprising a hole transport layer and at least one layer selected from a hole injection layer and an electron blocking layer, and
ii) an electron transport region between the emission layer and the second electrode, the electron transport region comprising at least one layer selected from an electron transport layer, a hole blocking layer, and an electron injection layer.

8. The organic light-emitting device of claim 7, wherein the hole transport layer comprises a first hole transport layer and a second hole transport layer.

9. The organic light-emitting device of claim 8, wherein the second hole transport layer comprises the compound represented by Formula 1.

10. The organic light-emitting device of claim 8, wherein the first hole transport layer comprises a compound represented by Formula 201A:

Formula 201A

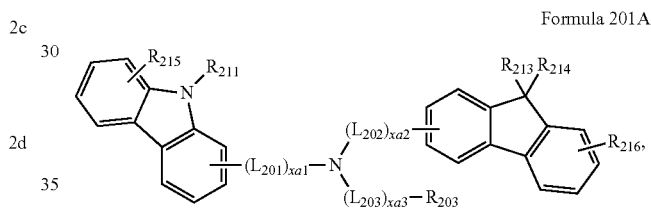

wherein, in Formula 201A,
$L_{201}$ to $L_{203}$ are each independently selected from the group consisting of: a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyrdinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 are each independently 0 or 1;

$R_{203}$ and $R_{211}$ are each independently selected from the group consisting of:

a phenyl group, a biphenyl group, a terphenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ are each independently selected from the group consisting of:

a $C_1$-$C_{20}$ alkyl group and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ are each independently selected from the group consisting of:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

11. The organic light-emitting device of claim 10, wherein the compound represented by Formula 201A is represented by one of Compounds HT1 to HT33:

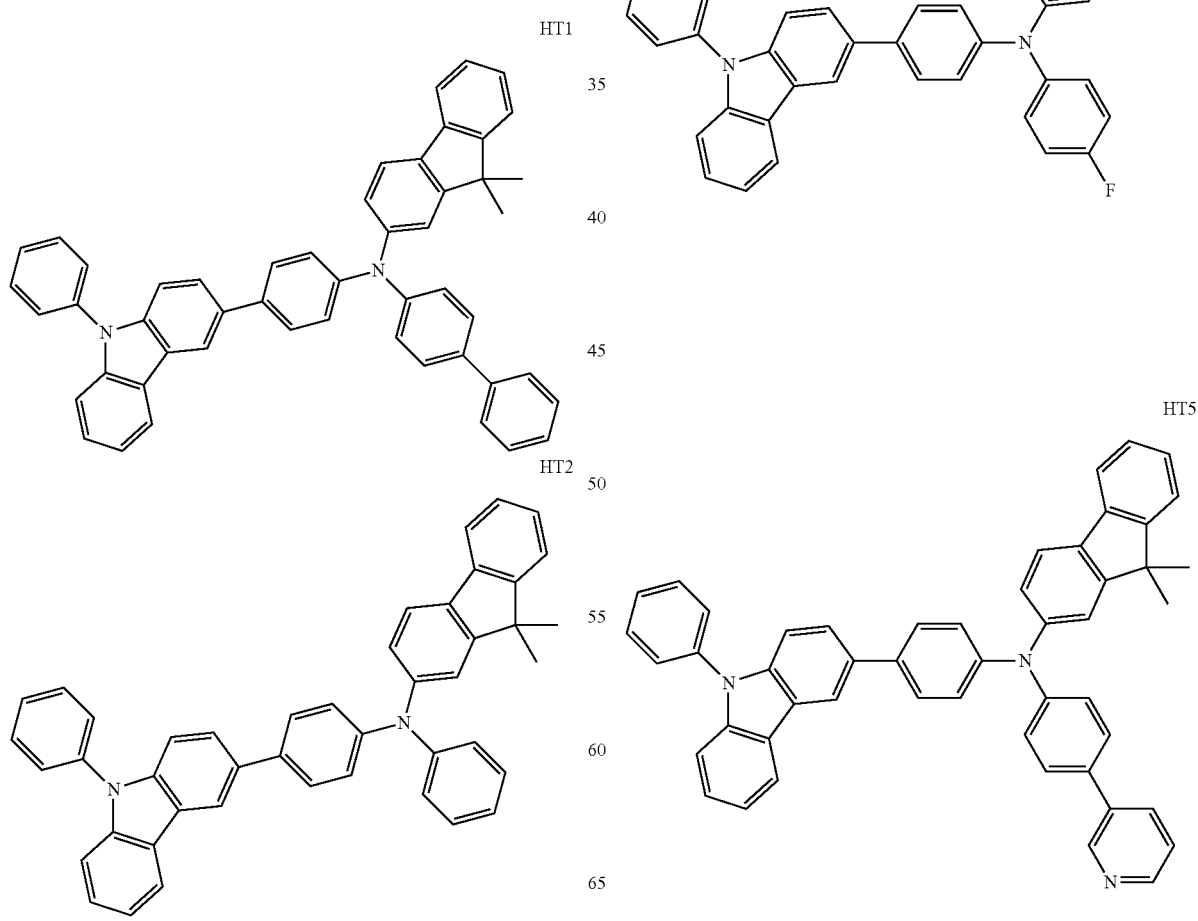
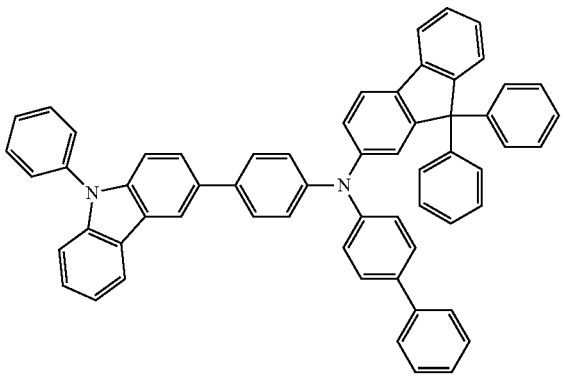
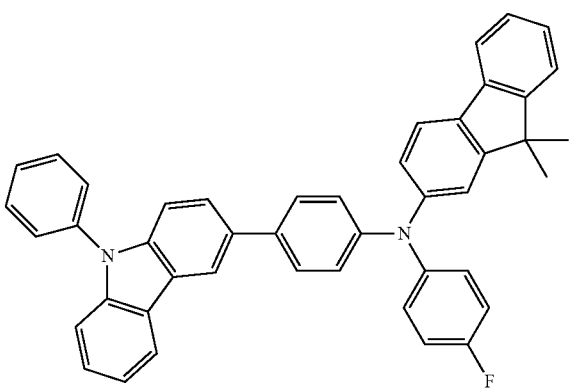

HT6
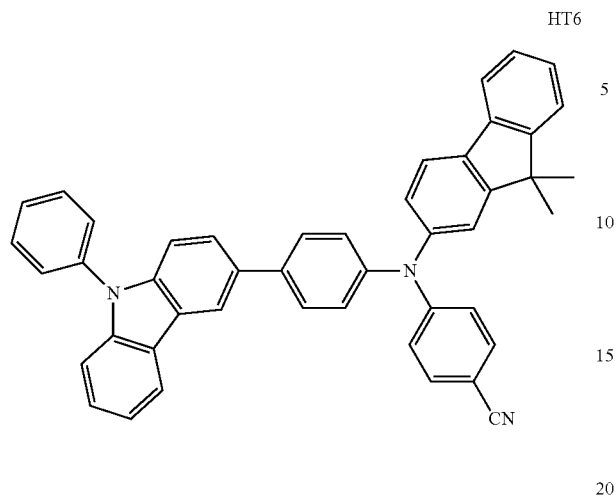
HT9
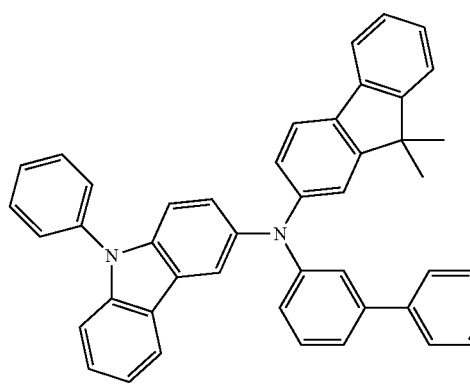
HT7
HT10
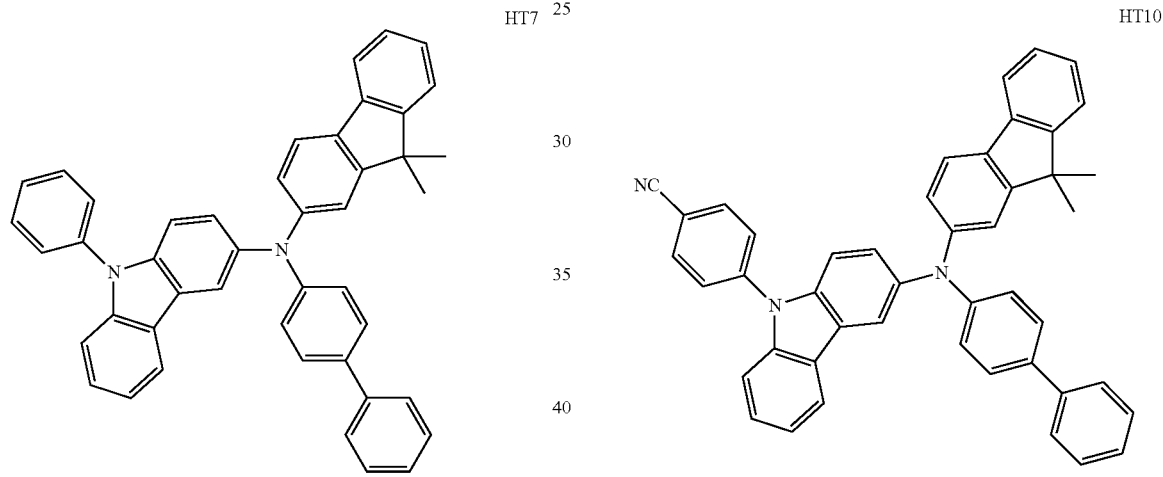
HT8
HT11
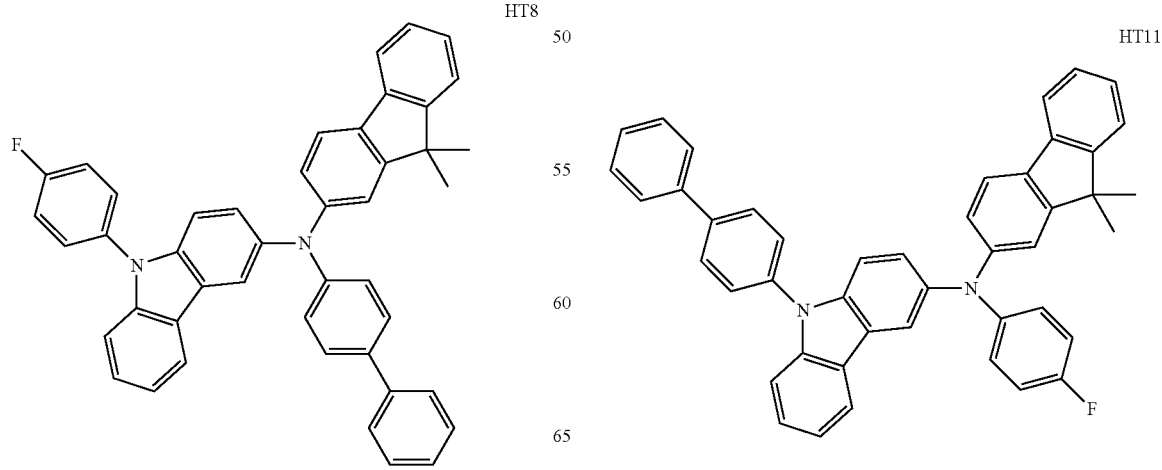

HT12
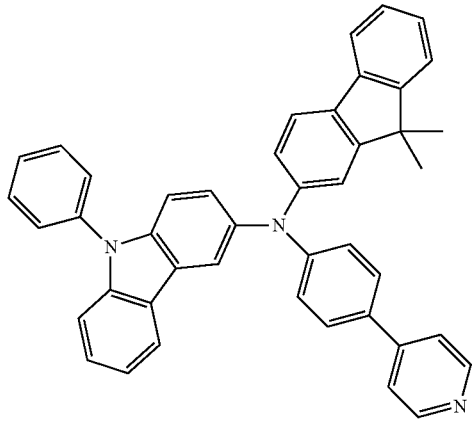
HT13
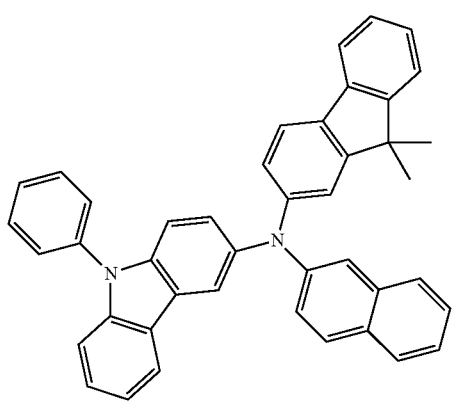
HT14
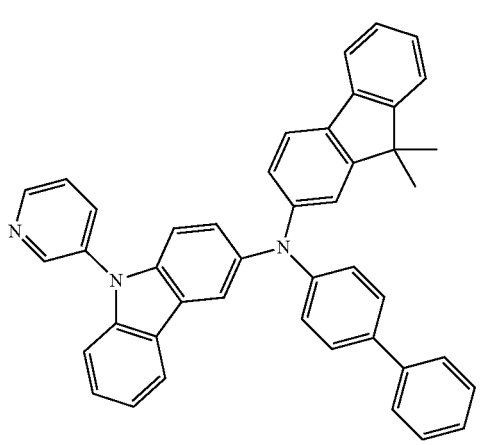
HT15
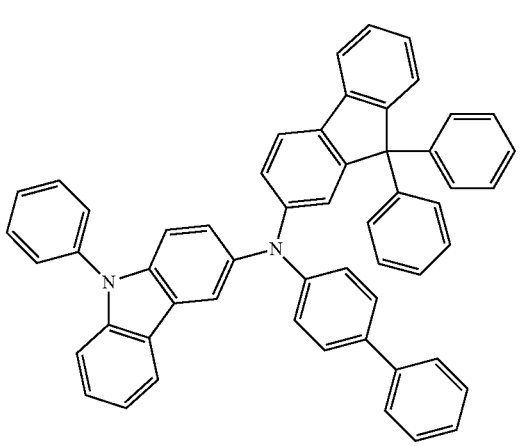
HT16
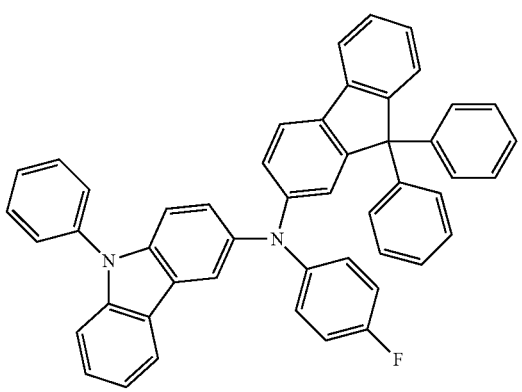
HT17

HT18
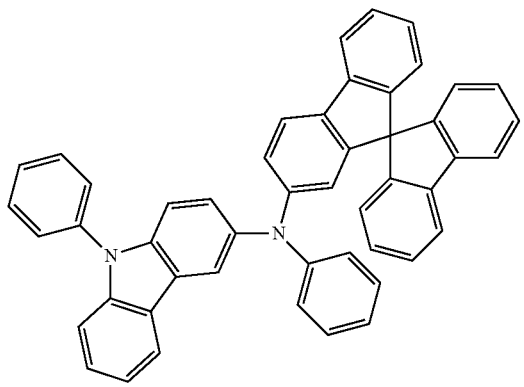
HT19
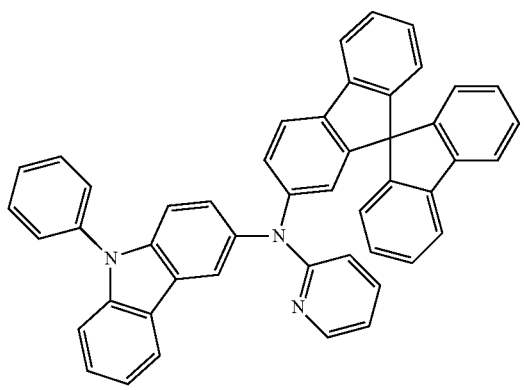
HT20
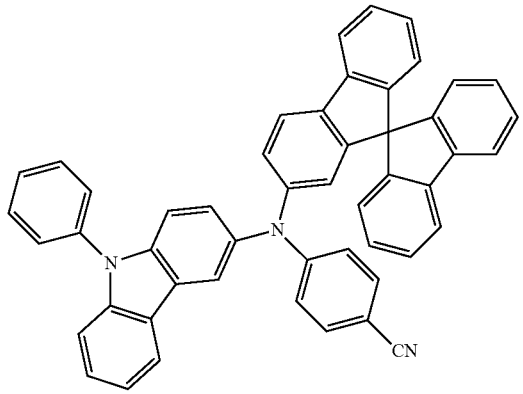
HT21
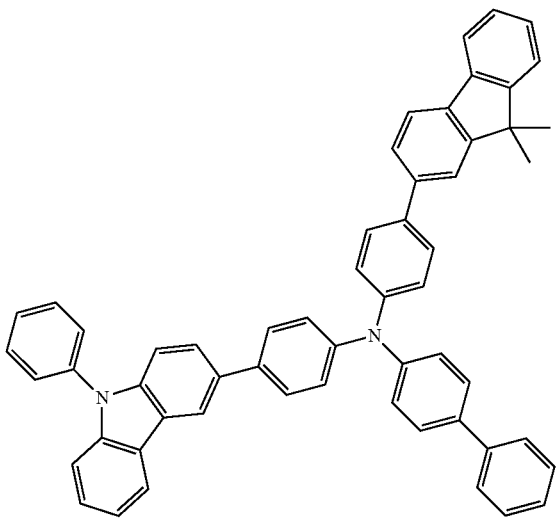
HT22
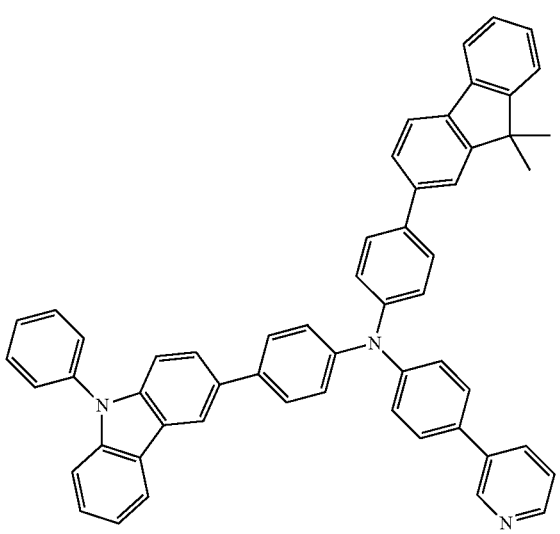
HT23
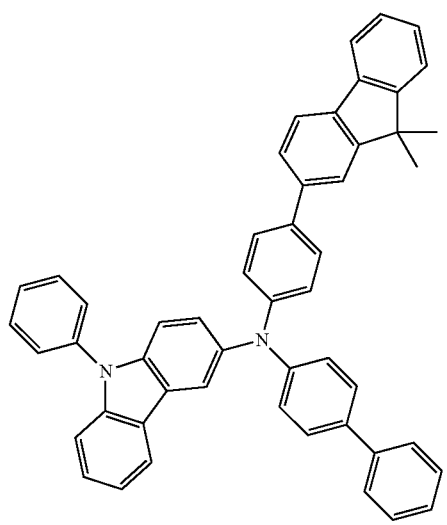

HT24
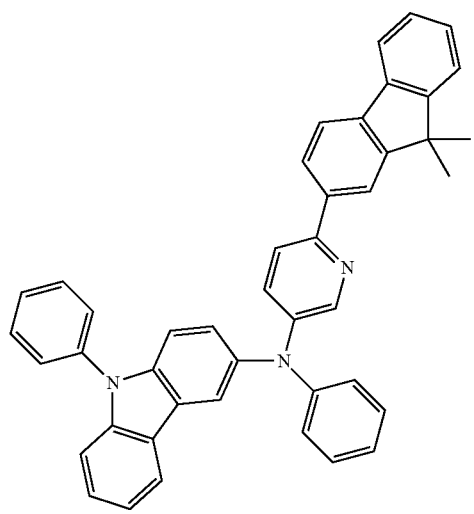
HT25
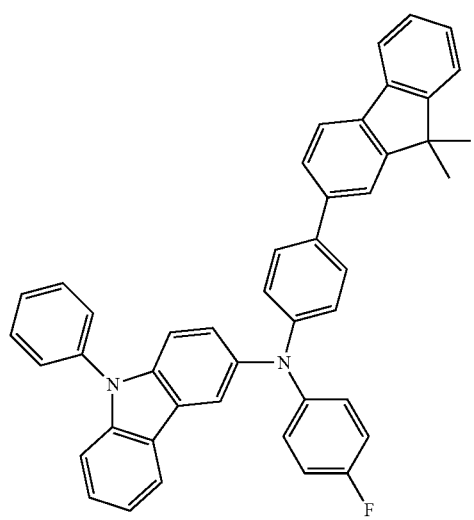
HT26
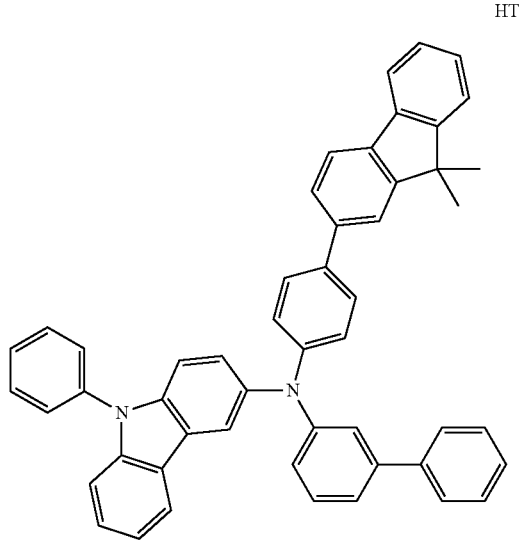
HT27
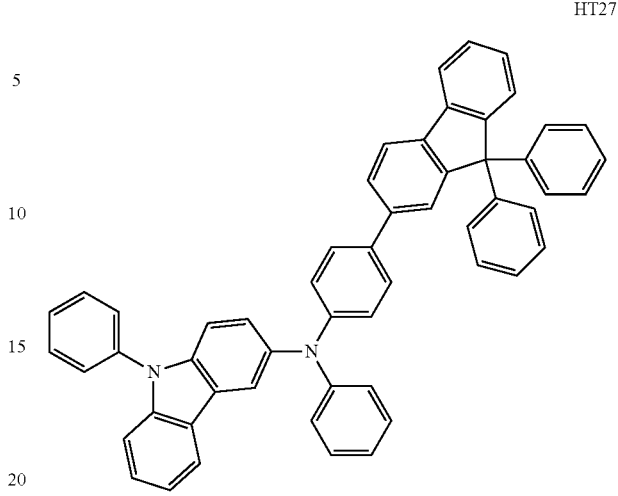
HT28
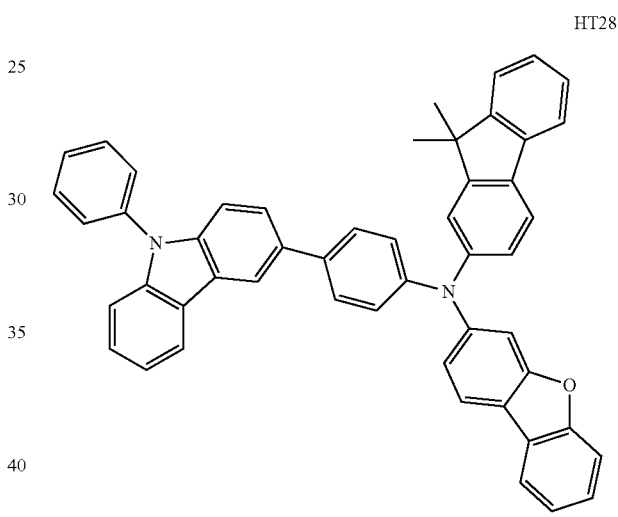
HT29
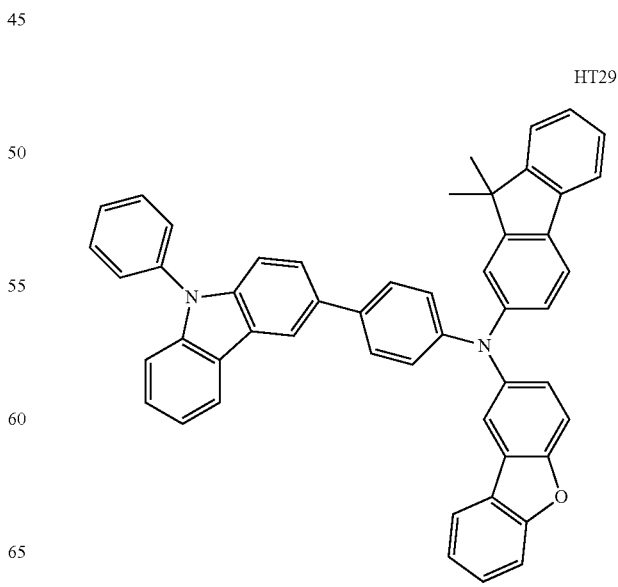

HT30
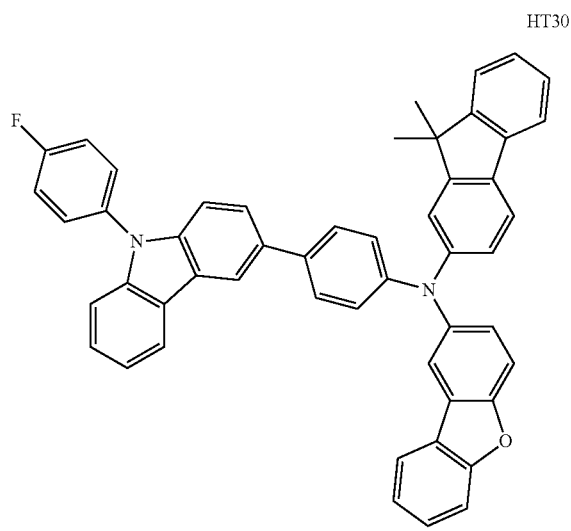
HT31
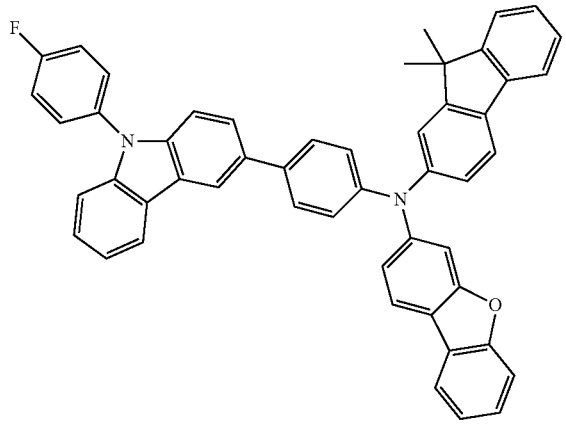
HT32
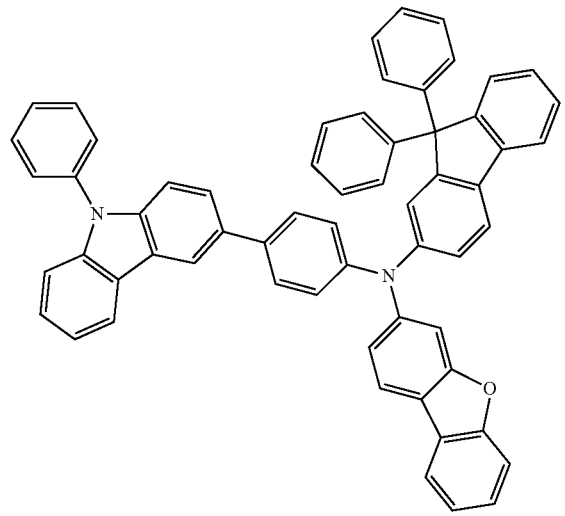
HT33
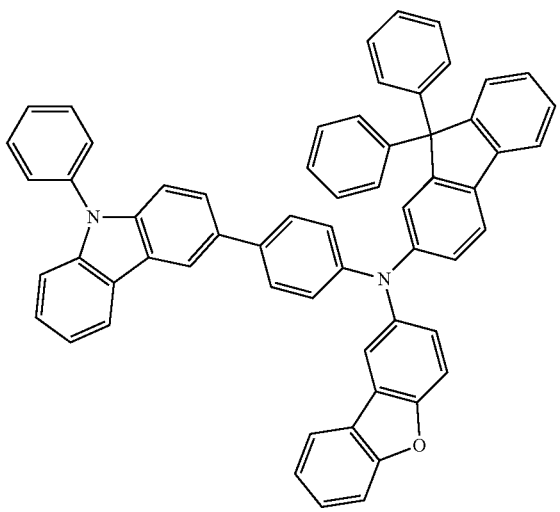
12. A display apparatus comprising the organic light-emitting device of claim 6, wherein the first electrode of the organic light-emitting device is electrically coupled to a source electrode or a drain electrode of a thin film transistor.
13. A compound represented by one of Compounds, 70, 71, and 72:
70
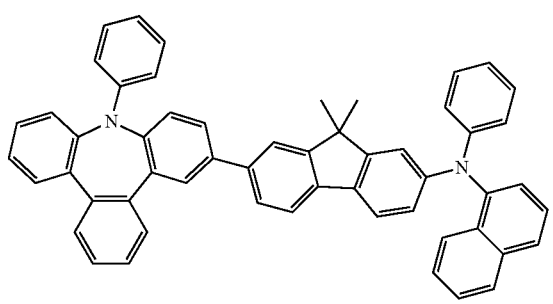

171 172
-continued
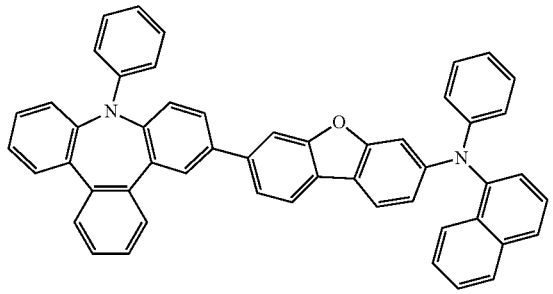 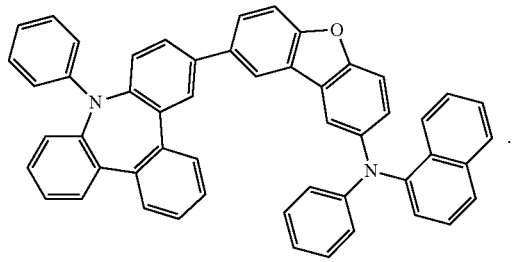
\* \* \* \* \*